United States Patent
Grillo et al.

(10) Patent No.: US 8,183,293 B2
(45) Date of Patent: May 22, 2012

(54) PHENYL ACETIC ACID DERIVATIVES

(75) Inventors: Mark Grillo, San Francisco, CA (US);
An-Rong Li, San Mateo, CA (US);
Jiwen Liu, Foster City, CA (US); Julio C. Medina, San Carlos, CA (US);
Yongli Su, Foster City, CA (US);
Yingcai Wang, Millbrae, CA (US);
Janan Jona, Simi Valley, CA (US); Alan Allgeier, Oak Park, CA (US);
Jacqueline Milne, Simi Valley, CA (US); Jerry Murry, Newbury Park, CA (US); Joseph F. Payack, Somerset, NJ (US); Thomas Storz, Warwick, NY (US)

(73) Assignee: Amgen Inc., Thousand Oaks, CA (US)

( * ) Notice: Subject to any disclaimer, the term of this patent is extended or adjusted under 35 U.S.C. 154(b) by 554 days.

(21) Appl. No.: 12/317,066

(22) Filed: Dec. 18, 2008

(65) Prior Publication Data
US 2009/0275659 A1    Nov. 5, 2009

Related U.S. Application Data

(60) Provisional application No. 61/008,433, filed on Dec. 19, 2007.

(51) Int. Cl.
*A61K 31/18*    (2006.01)
*C07C 311/08*    (2006.01)

(52) U.S. Cl. ........ 514/602; 514/562; 514/604; 514/605; 564/92; 564/97; 562/430

(58) Field of Classification Search .................. None
See application file for complete search history.

(56) References Cited

U.S. PATENT DOCUMENTS

| | | | |
|---|---|---|---|
| 5,545,669 | A | 8/1996 | Adams et al. |
| 5,849,780 | A | 12/1998 | Di Malta et al. |
| 5,929,250 | A | 7/1999 | Widdowson et al. |
| 5,962,682 | A | 10/1999 | Breu et al. |
| 6,008,234 | A | 12/1999 | Kochanny et al. |
| 6,133,442 | A | 10/2000 | Breu et al. |
| 6,531,291 | B1 | 3/2003 | Kabbash et al. |
| 7,321,001 | B2 | 1/2008 | Fu et al. |
| 7,541,383 | B2 | 6/2009 | Fu et al. |
| 2002/0022218 | A1 | 2/2002 | Li et al. |

(Continued)

FOREIGN PATENT DOCUMENTS
EP    0284202    9/1988

(Continued)

OTHER PUBLICATIONS

Burlingham, B. T., et al., An intuitive look at the relationship of Ki and IC50: a more genral use for the dixon plot, 2003, Journal of Chemical Education, vol. 80, issue 2, 1 page abstract.*

(Continued)

*Primary Examiner* — Yate K Cutliff
(74) *Attorney, Agent, or Firm* — Bernard P. Friedrichsen

(57) ABSTRACT

Compounds, pharmaceutical compositions and methods are provided that are useful in the treatment of inflammatory and immune-related diseases and conditions. In particular, the invention provides compounds which modulate the function and/or expression of proteins involved in atopic diseases, inflammatory conditions and cancer. The subject compounds are carboxylic acid derivatives.

20 Claims, 18 Drawing Sheets

AMG 009 Inhibits Antigen-Induced Late Airway Response (LAR) When Dosed At 7.5 mg/kg Single Dose

U.S. PATENT DOCUMENTS

2008/0312270 A1     12/2008    Brown et al.

FOREIGN PATENT DOCUMENTS

| | | |
|---|---|---|
| EP | 0930528 | 7/1999 |
| EP | 0947500 | 10/1999 |
| EP | 1170594 | 1/2002 |
| GB | 2388540 | 11/2003 |
| WO | WO 95/01326 | 1/1995 |
| WO | WO 95/33461 | 12/1995 |
| WO | WO 96/19455 | 6/1996 |
| WO | WO 98/11094 | 3/1998 |
| WO | WO 99/55663 | 11/1999 |
| WO | WO 00/17204 | 3/2000 |
| WO | WO 00/40561 | 7/2000 |
| WO | WO 00/51971 A1 | 9/2000 |
| WO | WO 00/53573 | 9/2000 |
| WO | WO 01/14882 | 3/2001 |
| WO | WO 01/57020 A1 | 8/2001 |
| WO | WO 01/79169 | 10/2001 |
| WO | WO 01/94309 | 12/2001 |
| WO | WO 02/45718 | 6/2002 |
| WO | WO 02/051805 A1 | 7/2002 |
| WO | WO 02/094830 | 11/2002 |
| WO | WO 03/016254 | 2/2003 |
| WO | WO 03/066046 | 8/2003 |
| WO | WO 03/066047 | 8/2003 |
| WO | WO 03/078409 | 9/2003 |
| WO | WO 03/097042 | 11/2003 |
| WO | WO 03/097598 | 11/2003 |
| WO | WO 03/101961 | 12/2003 |
| WO | WO 03/101981 | 12/2003 |
| WO | WO 2004/037788 A1 | 5/2004 |
| WO | WO 2004/058164 | 7/2004 |
| WO | WO 2005/054176 A1 | 6/2005 |
| WO | WO 2011/014587 A2 | 2/2011 |
| WO | WO 2011/014588 A2 | 2/2011 |

OTHER PUBLICATIONS

Silverman, R.B., The Organic Chemistry of Drug Design and Drug Action, 1992, Academic Press, (16 pages).*

International Search Report for analogous PCT Application PCT/US2008/013833 dated Apr. 28, 2009.

International Preliminary Report on Patentability and Written Opinion for analogous PCT Application PCT/US2008/013833 dated Jun. 22, 2010.

Kiang, Y.-H. et al., "Crystal structure, crystal morphology, and surface properties of an investigational drug" Int. J. Pharm., 368(1-2), 76-82 (2009).

Li, H. et al., "Multiple approaches to pharmaceutical polymorphism investigation—A case study" Eur. J. Pharm. Sci. 38, 426-432 (2009).

Liu, J. et al., "Discovery and optimization of CRTH2 and DP dual antagonists" Bioorg. Med. Chem. Lett., 19, 6419-6423 (2009).

Liu, J. et al., "Discovery of AMG 853, a CRTH2 and DP Dual Antagonist" ACS Med. Chem. Lett., ACS ASAP (2011).

Wolff, M.E. "Burger's Medicinal Chemistry, 5$^{th}$ Ed. vol. I: Principles and Practice", John Wiley & Sons, New York, pp. 975-977 (1995).

Banker, G. S. et al., "Modern Pharmaceutics, 3$^{rd}$ Ed. Revised and Expanded", Marcel Dekker, New York pp. 451 and 596 (1996).

West, A.R., "Solid State Chemistry and its Applications", Wiley, New York pp. 358 and 365 (1988).

Armer et al., "Indole-3-acetic Acid Antagonists of the Prostaglandin D2 Receptor CRTH2", J. Med. Chem. 48, 6174-6177 (2005).

Sturino et al., "Discovery of a Potent and Selective Prostaglandin D2 Receptor Antagonists, [(3R)-4-(4-Chlorobenzyl)-7-fluoro-5-(methylsulfonyl)-1,2,3,4-tetrahydrocyclopenta[b]indol-3-yl]acetic Acid (MK-0524)", J. Med. Chem. 50, 794-806 (2007).

Medina, J. C. "Discovery and Development of AMG 009; A CRTH2 and DP Dual-Antagonist", Presentation at ACS National Meeting, Boston, MA, Aug. 19-23, 2007.

Medina, J. C. "Discovery and Development of AMG 009; A CRTH2 and DP Dual-Antagonist", Abstract for Presentation at ACS National Meeting, Boston, MA, Aug. 19-23, 2007. Abstract Published Jul. 25, 2007.

Johnson, M.G. et al., "Indole-phenylacetic acid inhibitors of CRTH2", Presentation at 235th ACS National Meeting, New Orleans, LA, Aug. 6-8, 2008.

Johnson, M.G. et al., "Indole-phenylacetic acid inhibitors of CRTH2", Abstract for Presentation at 235th ACS National Meeting, New Orleans, LA, Aug. 6-8, 2008. Abstract published Feb. 27, 2008.

Liu, J. et al., "Tetrahydroquinoline Derivatives as CRTH2 Antagonists", Bioorg. Med. Chem. Lett., 19, 6840-6844 (2009).

Liu, J. et al., "Benzodiazepinone Derivatives as CRTH2 Antagonists", ACS Med. Chem. Lett., ACS ASAP (2011). Received Feb. 11, 2011, Accepted Apr. 17, 2011.

Cosmi et al., "Chemoattractant Receptors Expressed on Type 3 T Cells and Their Role in Disease," Int. Arch. Allergy Immunol., 125:273-279 (2001).

Fujitani et al., "Pronounced Eosinophilic Lung Inflammation and Th2 Cytokine Release in Human Lipocalin-Type Prostaglandin D Synthase Transgenic Mice," J. Immunol., 168:443-449 (2002).

Hirai et al., "Prostaglandin D2 Selectively Induces Chemotaxis T Helper Type 2 Cells, Eosinophils, and Basophils via Seven-Transmembrane Receptor CRTH2," J. Exp. Med., 193(2):255-261 (2001).

Iwasaki et al., "Association of a New-Type Prostaglandin D2 Receptor CRTH2 with Circulating T Helper 2 Cells in Patients with Atoipic Dermatitis," J. Investigative Dermatology, 119(3):609-616 (2002).

Matsuoka et al., "Prostaglandin D2 as a Mediator of Allergic Asthma," Science, 287(17):2013-2017 (2000).

Monneret et al., "Prostaglandin D2 is a Potent Chemoattractant for Human Eosinophils that Act via a Novel DP Receptor," J. Exp. Med., 193(2):255-261 (2001).

Munns et al., "Contribution of Type 27 II PLA2 to Prostaglandin Formation: A Study Using a Type II PLA2 Specific Inhibitor SB 203347," Prostaglandins & Other Lipid Mediators 57:5,6:361-370 (1999).

Romagnani et al., "Cytokines and Chemoattractants in Allergic Inflammation," Molecular Immunology, 38:881-885 (2001).

Saito et al., "Prostaglandin D2 and Reproduction," AM. J. of Reproductive Immunology, 47:295-302 (2002).

* cited by examiner

AMG 009 Inhibits Antigen-Induced Late Airway Response (LAR) When Dosed At 7.5 mg/kg Single Dose —◇— Untreated
—□— 7.5 mg/kg single dose AMG 009 Inhibits Antigen-Induced Development of Airway Hyperreactivity to Carbochol When Dosed At 7.5 mg/kg Single Dose AMG 009 Inhibits Antigen-Induced Late Airway Response (LAR) When Dosed At 15 mg/kg Single Dose —◇— Untreated
—□— 15 mg/kg single dose AMG 009 Inhibits Antigen-Induced Development of Airway Hyperreactivity to Carbochol When Dosed At 15 mg/kg Single Dose AMG 009 Inhibits Antigen-Induced Late Airway Response (LAR) When Dosed At 7.5 mg/kg Multi-Dose — ◇ — Untreated
— □ — 7.5 mg/kg multi-dose AMG 009 Inhibits Antigen-Induced Development of Airway Hyperreactivity to Carbochol When Dosed At 7.5 mg/kg Multi-Dose

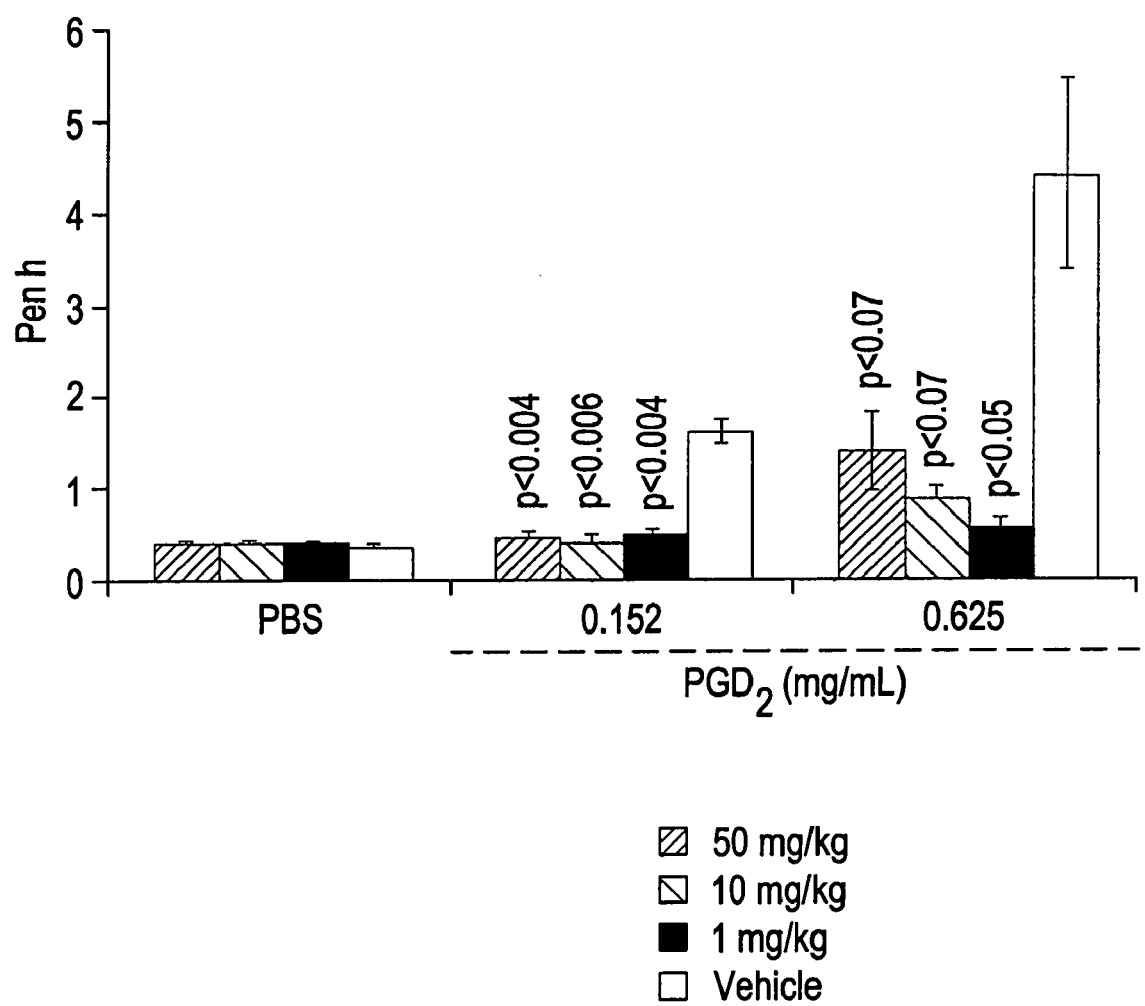

Powder X-Ray Diffraction Spectra for Form I Polymorph of Example Compound 14

Tabular Presentation of Powder X-Ray Data

| 2-theta | Intensity (%) | Peak Type<br>p = primary<br>s = secondary |
|---|---|---|
| 6.3 | 42.6 | p |
| 6.8 | 13.7 | s |
| 8.8 | 100 | p |
| 9.5 | 30.57 | s |
| 9.9 | 38.31 | p |
| 12.2 | 18.01 | s |
| 14.7 | 46.66 | p |
| 15.4 | 39.36 | s |
| 16.2 | 35.56 | p |
| 17.6 | 32.96 | s |
| 18.0 | 38.89 | p |
| 18.3 | 23.88 | s |
| 19.4 | 79.04 | p |
| 19.7 | 94.92 | p |
| 20.2 | 37.66 | p |

Powder X-Ray Diffraction Spectra for Anhydrous Form II Polymorph of Example Compound 14

Tabular Presentation of Powder X-Ray Data

| 2-theta | Intensity (%) | Peak Type p = primary s = secondary |
|---|---|---|
| 19.2 | 100 | p |
| 9.5 | 95.64 | p |
| 22.0 | 73.31 | p |
| 20.2 | 56.38 | p |
| 17.2 | 52.51 | p |
| 16.6 | 50.67 | p |
| 13.4 | 45.10 | p |
| 14.8 | 42.35 | p |
| 6.7 | 41.61 | p |
| 15.1 | 37.44 | p |
| 12.2 | 28.21 | s |
| 19.8 | 24.37 | s |
| 10.1 | 23.45 | s |
| 8.3 | 12.52 | s |

Powder X-Ray Diffraction Spectra for Form III Polymorph of Example Compound 14

Tabular Presentation of Powder X-Ray Data

| 2-theta | Intensity (%) | Peak Type<br>p = primary<br>s = secondary |
|---|---|---|
| 6.4 | 12.3 | s |
| 7.6 | 9.39 | s |
| 8.5 | 25.03 | p |
| 11.2 | 45.63 | p |
| 12.9 | 14.47 | s |
| 13.4 | 13.62 | s |
| 13.9 | 29.83 | p |
| 14.7 | 39.94 | p |
| 15.1 | 50.75 | p |
| 19.7 | 56.19 | p |
| 20.9 | 100 | p |

Powder X-Ray Diffraction Spectra for
Form IV (hydrate) Polymorph of Example Compound 14

Tabular Presentation of Powder X-Ray Data

| 2-theta | Intensity (%) | Peak Type<br>p = primary<br>s = secondary |
|---|---|---|
| 6.9 | 95.84 | p |
| 13.4 | 79.57 | p |
| 13.8 | 17.76 | s |
| 14.2 | 19.43 | s |
| 14.6 | 5.94 | s |
| 16.5 | 6.13 | s |
| 17.2 | 9.99 | s |
| 18.0 | 7.47 | s |
| 18.9 | 67.58 | p |
| 19.5 | 21.04 | s |
| 20.7 | 15.13 | s |
| 21.5 | 38.61 | p |
| 22.3 | 84.29 | p |
| 24.4 | 100 | p |

Powder X-Ray Diffraction Spectra for
Form V (EtOH solvate) Polymorph of Example Compound 14

Tabular Presentation of Powder X-Ray Data

| 2-theta | Intensity (%) | Peak Type<br>p = primary<br>s = secondary |
|---|---|---|
| 6.3 | 32.00 | p |
| 8.4 | 37.65 | p |
| 10.1 | 49.54 | p |
| 13.8 | 49.46 | p |
| 18.4 | 18.65 | s |
| 18.9 | 19.14 | s |
| 19.7 | 17.68 | s |
| 20.7 | 16.03 | s |
| 21.3 | 55.84 | p |
| 22.0 | 13.08 | s |
| 22.2 | 35.14 | p |
| 22.7 | 22.76 | s |
| 23.5 | 24.05 | p |
| 25.0 | 100 | p |

Powder X-Ray Diffraction Spectra for Form VI (hydrate) Polymorph of Example Compound 14

Tabular Presentation of Powder X-Ray Data

| 2-theta | Intensity (%) | Peak Type p = primary s = secondary |
|---|---|---|
| 6.4 | 41.62 | p |
| 6.8 | 13.60 | s |
| 7.5 | 22.04 | s |
| 8.4 | 100 | p |
| 9.0 | 37.47 | s |
| 11.1 | 62.66 | p |
| 13.4 | 46.79 | p |
| 13.9 | 23.68 | s |
| 14.6 | 40.05 | p |
| 15.1 | 44.33 | p |
| 17.8 | 60.89 | p |
| 18.0 | 69.33 | p |
| 20.8 | 65.55 | p |

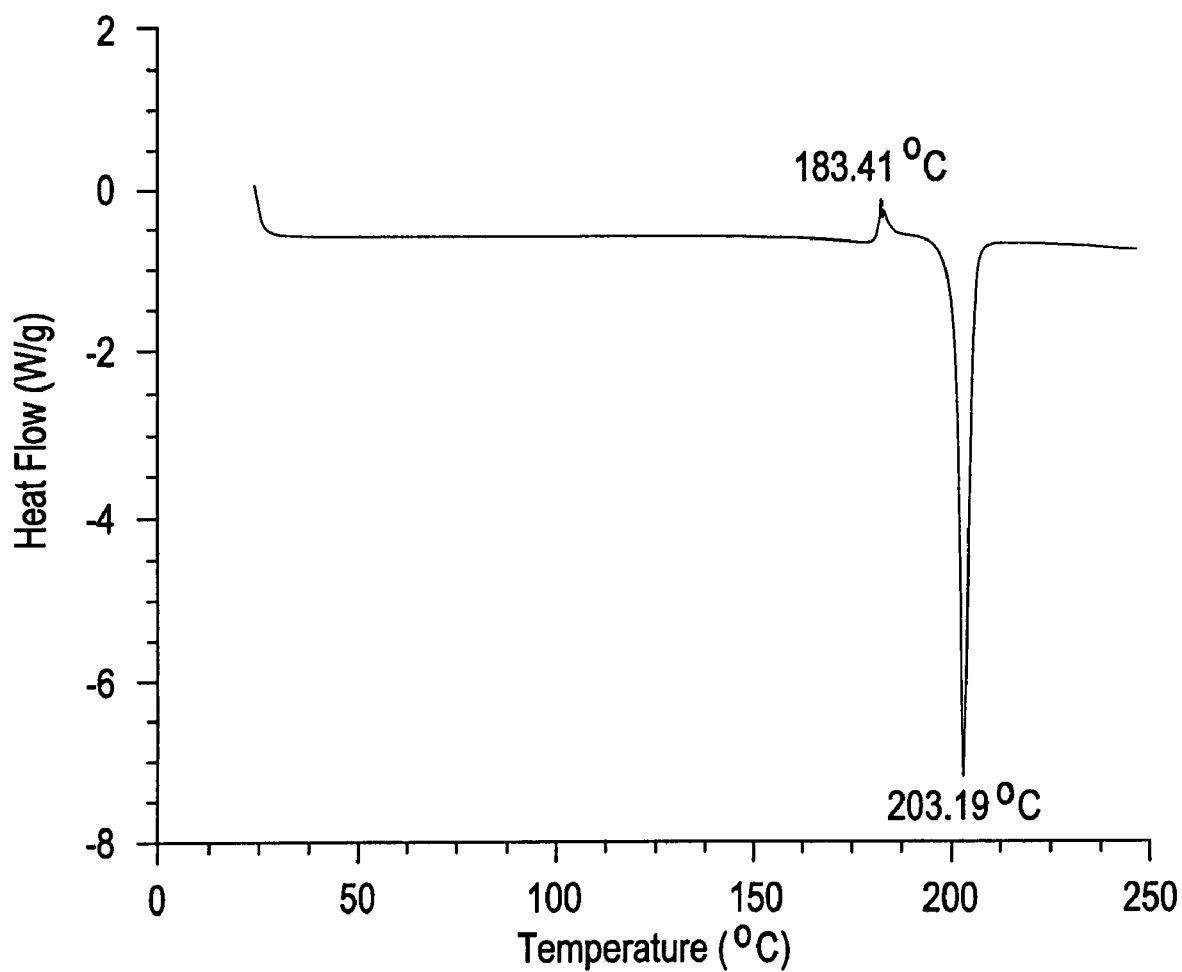

DSC Thermogram of Form II (anhydrous) Polymorph of Example Compound 14 Heating Rate = 10 °C per minute DSC Thermogram of Form III (anhydrous) Polymorph of Example Compound 14 Heating Rate = 10 °C per minute DSC Thermogram of Form IV (hydrate) Polymorph of Example Compound 14 Heating Rate = 10 °C per minute DSC Thermogram of Form V (EtOH solvate) Polymorph of Example Compound 14 Heating Rate = 10 °C per minute DSC Thermogram of Form VI (hydrate) Polymorph of Example Compound 14 Heating Rate = 10 °C per minute

PHENYL ACETIC ACID DERIVATIVES

CROSS-REFERENCE TO RELATED PATENT APPLICATIONS

This application claims priority to U.S. Provisional Application Ser. No. 61/008,433 filed Dec. 19, 2007 the entirety of which is incorporated herein by reference.

BACKGROUND OF THE INVENTION

G-protein coupled receptors play important roles in diverse signaling processes, including those involved in host defense mechanisms. Immune responses to infectious diseases, injury, tumors and organ transplantation and in diseases and conditions such as asthma, allergy, rheumatoid arthritis and neoplasia have been linked to GPCR regulation. Exaggerated or misdirected immune responses are responsible for many inflammatory and hypersensitivity diseases which, left untreated, can result in tissue or organ damage, pain and/or loss of function. Tissue inflammation is largely implicated in the pathogenesis of such diseases, of which asthma and allergic diseases are among the most well characterized. The mechanisms underlying airway inflammation and hyperreactivity are similar to those underlying allergic inflammation in other tissues, such as the skin and gut.

Prostaglandins are lipid-derived inflammatory mediators that recruit macrophages, T cells, eosinophils, basophils and neutrophils from peripheral blood to damaged or inflamed tissues. In addition, prostaglandins can, depending on the target cell type, induce or inhibit intracellular $Ca^{2+}$ mobilization, cAMP production, platelet aggregation, leukocyte aggregation, T cell proliferation, lymphocyte migration, and Th2 cell chemotaxis, IL-1a and IL-2 secretion and vascular and non-vascular smooth muscle contraction in responsive cells. Prostaglandins have been implicated in fever, various allergic diseases, vascular and non-vascular smooth muscle relaxation, pain perception, sleep, platelet aggregation and reproductive processes. Prostaglandins exert their effects by interacting with specific GPCRs.

Prostaglandin $D_2$ ($PGD_2$) is the major inflammatory mediator released by activated mast cells, typically found near skin surfaces, mucous membranes and blood vessels, upon immunological challenge (Lewis et al. (1982) *J. Immunol.* 129:1627-1631). During asthma and allergic responses, $PGD_2$ is released in large amounts. The role of $PGD_2$ in the initiation and maintenance of allergic inflammation has been well established in mouse models of asthma. For example, it has been demonstrated that overproduction of $PGD_2$ in vivo by $PGD_2$ synthase exacerbates airway inflammation in a mouse model of asthma (Fujitani et al. (2002) *J. Immunol.* 168:443-449).

A $PGD_2$-selective receptor, designated DP, has been identified (Power et al. (1995) *J. Biol. Chem.* 270:19495-19500). In humans, DP is expressed in smooth muscle, platelets, small intestine and brain, and its expression in lung epithelium is induced by allergic challenge. Receptor activation induces cAMP production and intracellular $Ca^{2+}$ mobilization, and is believed to inhibit platelet aggregation and cell migration and induce relaxation of various smooth muscles. DP is coupled primarily to G□s protein.

Significantly, in an OVA induced asthma model, $DP^{-/-}$ mice exhibited reduced asthma symptoms, e.g., reduced cellular infiltration of eosinophils and lymphocytes in BAL fluid, reduced Th2 cytokine levels in BAL fluid and reduced airway hyperreactivity to acetylcholine (Matsuoka et al. (2002) *Science* 287:2013-2019). The increased cellular infiltration in lung tissue and mucus secretion by airway epithelial cells characteristic of asthma in humans and observed in wild-type mice was not observed in DP-deficient mice.

Recently, an additional $PGD_2$-selective receptor, designated chemoattractant receptor-homologous molecule expressed on Th2 cells, or CRTH2, has been identified (Hirai et al. (2001) *J. Exp. Med.* 193(2):255-261). The receptor was previously referred to as GPR44 or DLIR. Among peripheral blood T lymphocytes, human CRTH2 is selectively expressed on Th2 cells, and is highly expressed on cell types associated with allergic inflammation such as eosinophils, basophils and Th2 cells. It has been shown that CRTH2 activation induces intracellular $Ca^{2+}$ mobilization and infiltration of Th2 cells, eosinophils and basophils.

Protein sequence analysis indicates that CRTH2 has no significant homology to DP, but rather, is related to members of the N-formyl peptide receptor (FPR) subfamily (Nagata et al. (1999) *J. Immunol.* 162:1278-1286). In contrast to DP, CRTH2 has been shown to couple primarily to G□i protein.

These observations suggest that CRTH2 and DP may function independently to regulate aspects of allergic inflammation.

The increasing incidence of asthma, allergic diseases and immunologic diseases worldwide underscores the need for new therapies to effectively treat or prevent these diseases. The discovery of small molecules that modulate CRTH2 and/or one or more other $PGD_2$ receptors is useful for the study of physiological processes mediated by CRTH2 and/or one or more other $PGD_2$ receptors and the development of therapeutic agents for asthma, allergic diseases and other immunologic diseases. Novel compounds which display such desirable activity are described herein.

WO 04/058164 discloses certain arylsulfonamide substituted carboxylic acid compounds as asthma and allergic inflammation modulators. From the class of compounds disclosed in WO 04/058164, AMG 009 was selected as the most preferred compound to advance into clinical trials. The structure of AMG 009 is provided below.

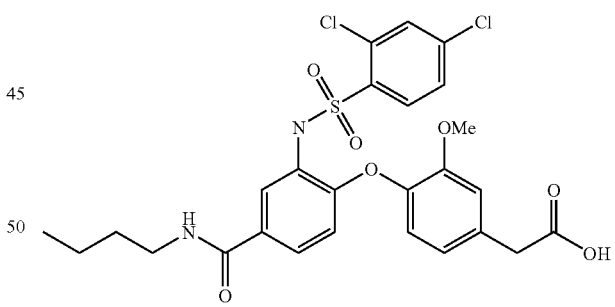

AMG 009

When tested in the sheep airway response model, as described in *Can J Physiol Pharmacol* 1995; 73:191, AMG 009 (1) inhibits antigen-induced late airway response (LAR); (2) blocks antigen-induced development of airway hyper-reactivity (AHR) to carbachol; and (3) blocked allergen-induced recruitment of inflammatory cells to the lung (BAL) (see FIGS. 1, 2 and 3 respectively).

The development of AMG 009 was suspended after unanticipated increases in hepatic ALT/AST levels were observed in healthy volunteers that had received AMG 009. Changes in hepatic function were not anticipated from preclinical safety studies with AMG 009. In vitro metabolism studies revealed that AMG 009 can be metabolically activated to chemically-reactive intermediates capable of forming covalent adducts with proteins. The propensity of AMG 009 metabolism to generate reactive metabolites was conducted in studies to evaluate in vitro covalent binding to protein by standardized methods (Day, et al., *J. Pharmacol. Toxicol. Methods.*, 52, 278-285 (2005)). These studies showed that [$^{14}$C]AMG 009 radioactive equivalents were bound covalently to protein following incubations with rat and human liver microsomes in the presence of NADPH cofactor at a level of ~50 pmol equivalent/mg protein. The covalent binding of [$^{14}$C]AMG 009 to protein in microsomes was in the same range as a target cutoff for acceptable covalent binding in microsomes (50 pmol equivalents/mg protein) as reported in the literature (Evans, et al. *Chem. Res. Toxicol.*, 17, 3-16 (2004)).

The target covalent binding number of 50 pmol equivalents of the drug residue per mg of protein is a target covalent binding value, but is not a threshold. The number of 50 pmol equivalents of the drug residue/mg of protein was not arbitrarily-derived, but came from a thorough literature search of the levels of covalent binding to liver proteins in animals dosed with known hepatotoxins, for example bromobenzene (Monks, T. J. et al., (1982) *Life Sci.*, 30, 841-848), isoniazid (Nelson, S. D. et al, (1978) *J. Pharmacol. Exp. Ther.*, 206, 574-585), and acetaminophen (Matthews, A. M. et al, (1997) *Toxicol. Lett.*, 90, 77-82), under conditions where these drugs induced hepatotoxicity (Evans, D. C. et al, (2004 *Chem. Res. Toxicol.*, 17, 3-16). When the values of covalent binding to protein for these drugs were measured, the levels were as high as 1000 to 2000 pmol equivalents/mg liver protein. Therefore, the covalent binding target adopted by Merck Research Laboratories (Evans, D. C. et al, (2004) *Chem. Res. Toxicol.*, 17, 3-16) is about 20-fold less than that caused by many of these model hepatotoxic drugs.

Many persons of skill in the art currently view chemically-reactive metabolites as an unwanted feature of any drug or drug candidate (Baillie, T. A. (2007) *Chem. Res. Toxicol.* 2007 Dec. 4 [Epub ahead of print]). Therefore, a goal in drug discovery is to eliminate, or at least to minimize, the metabolic activation liability of drug candidates in that it might assist in leading to the increased probability of safer drugs being successfully developed (Baillie, T. A. et al, (2001) *Adv. Exp. Med. Biol.*, 500, 45-51; Park, B. K., et al (2005) *Ann. Rev. Pharmacol. Toxicol.*, 45, 177-202; Baillie, T. A. (2006) *Chem. Res. Toxicol.*, 19, 889-893; Doss, G. A. and Baillie, T. A. (2006). *Drug Metab. Rev.*, 38, 641-649; Kalgutkar, A. S. and Soglia, J. R. (2005) *Expert Opin. Drug Metab. Toxicol.*, 1, 91-142).

The clinical dose of a pharmaceutical compound is also an important factor, since there have been very few drugs that have been removed from the market for toxicological reasons when the daily dose was less than 10 milligrams (Uetrecht, J. P. (1999) *Chem. Res. Toxicol.*, 12, 387-395).

The compounds of the current invention exhibit unexpectedly improved DP potency, and additionally exhibit improved balance of CRTH2 and DP potencies when compared to the closest compounds disclosed in WO 04/058164, as well as when compared to most preferred compound within that class, AMG 009. This improvement would be expected to allow for a lower clinical dose than that used for AMG 009. Moreover, structural distinctions between the compounds of the current invention and AMG 009 are expected to block metabolism at the metabolic sites found in AMG 009, which may further help to avoid the covalent binding problems that were encountered with AMG 009.

SUMMARY OF THE INVENTION

The invention provides compounds, pharmaceutical compositions and methods useful for treating or preventing conditions and disorders associated with allergic inflammation processes. In particular, the invention provides compounds, pharmaceutical compositions and methods useful for treating or preventing asthma, allergic diseases, inflammatory conditions and cancer.

The current invention relates to compounds of the following Formula I

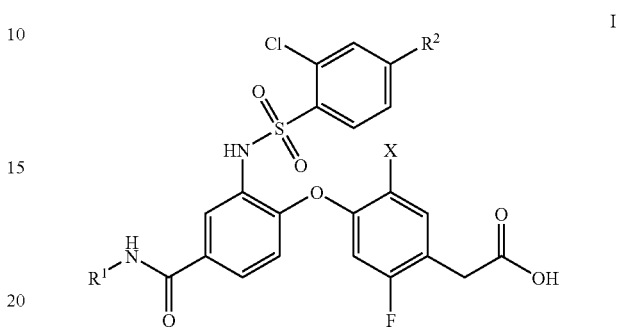

and salts thereof
wherein
$R^1$ is alkyl or cycloalkyl;
$R^2$ is halo, alkyl, haloalkyl, alkoxy, haloalkoxy or cycloalkyl; and
X is chloro or fluoro.

The invention also provides pharmaceutical compositions comprising compounds of Formula I, active metabolites or salts thereof together with a pharmaceutically acceptable carrier, excipient or diluent.

The invention also provides methods for treating or preventing asthma, allergic rhinitis, COPD, eczema, psoriasis, atopic dermatitis, fever, sepsis, systemic lupus erythematosus, diabetes, rheumatoid arthritis, multiple sclerosis, atherosclerosis, transplant rejection, inflammatory bowel disease and cancer, comprising administering to a subject in need thereof a therapeutically effective amount of a compound of Formula I, active metabolites, or salts thereof.

The invention further provides methods for treating or preventing a condition or disorder responsive to modulation of CRTH2 and/or one or more other $PGD_2$ receptors, comprising administering to a subject in need thereof a therapeutically effective amount of a compound of Formula I, active metabolites, or salts thereof.

The invention also provides methods for treating or preventing a condition or disorder mediated by CRTH2 and/or one or more other $PGD_2$ receptors, comprising administering to a subject in need thereof a therapeutically effective amount of a compound of Formula I, active metabolites, or salts thereof.

The invention also provides methods for modulating CRTH2 and/or one or more other $PGD_2$ receptors, comprising contacting a cell with a compound of Formula I, active metabolites, or salts thereof.

The invention also provides for a method of making compounds of Formula I, as well compounds made by claimed processes.

Other objects, features and advantages of the invention will become apparent to those skilled in the art from the following description and claims.

BRIEF DESCRIPTION OF THE DRAWINGS

FIG. 1A is a graph showing that AMG 009 inhibits antigen-induced late airway response when dosed at 7.5 mg/kg (single dose). FIG. 1B shows that AMG 009 inhibits antigen-induced development of airway hyperreactivity to carbochol when dosed at 7.5 mg/kg (single dose).

FIG. 2A is a graph showing that AMG 009 inhibits antigen-induced late airway response when dosed at 15 mg/kg (single dose). FIG. 2B shows that AMG 009 inhibits antigen-induced development of airway hyperreactivity to carbochol when dosed at 15 mg/kg (single dose).

FIG. 3A is a graph showing that AMG 009 inhibits antigen-induced late airway response when dosed at 7.5 mg/kg (multi-dose). FIG. 3B shows that AMG 009 inhibits antigen-induced development of airway hyperreactivity to carbochol when dosed at 7.5 mg/kg (multi-dose).

FIG. 4A shows total cells. FIG. 4B shows neutrophils. FIG. 4C shows eosinophils. FIG. 4D shows monocytes. FIG. 4E shows macrophages. FIG. 4F shows lymphocytes.

FIG. 5 is a graph of Guinea Pig Model data showing that Example Compound 14 provides a dose-dependent response when the subject animals are pretreated with aerosolized $PGD_2$ at doses as high as 0.625 mg/mL.

FIG. 7A is the powder x-ray diffraction spectrum and FIG. 7B is a table with the powder x-ray data.

FIG. 8A is the powder x-ray diffraction spectrum and FIG. 8B is a table with the powder x-ray data.

FIG. 9A is the powder x-ray diffraction spectrum and FIG. 9B is a table with the powder x-ray data.

FIG. 10A is the powder x-ray diffraction spectrum and FIG. 10B is a table with the powder x-ray data.

FIG. 11A is the powder x-ray diffraction spectrum and FIG. 11B is a table with the powder x-ray data.

FIG. 12A is the powder x-ray diffraction spectrum and FIG. 12B is a table with the powder x-ray data.

FIG. 13 illustrates a DSC thermogram obtained for Example Compound 14 Form I polymorph, which shows two thermal transitions (an exothermic transition at around 183.41° C. and an endothermic transition at around 203.19° C.

Figure 1A:
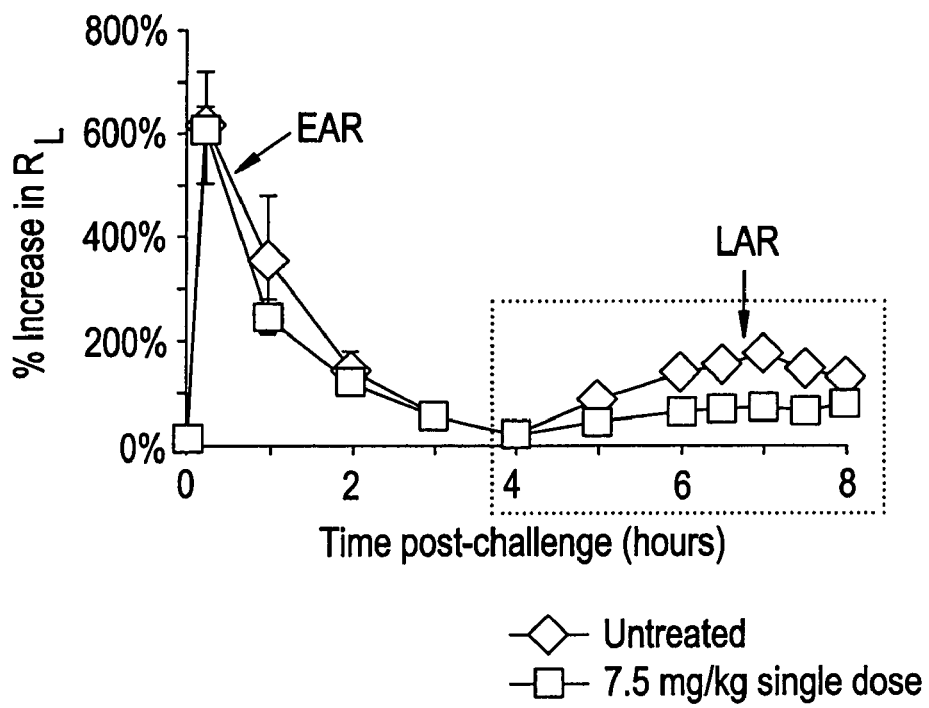
FIGS. 1A and 1B are graphs showing data obtained demonstrating the efficacy of AMG 009 (when dosed at 7.5 mg/kg single dose) in the Sheep Airway Response Model of Asthma.
Figure 1B:
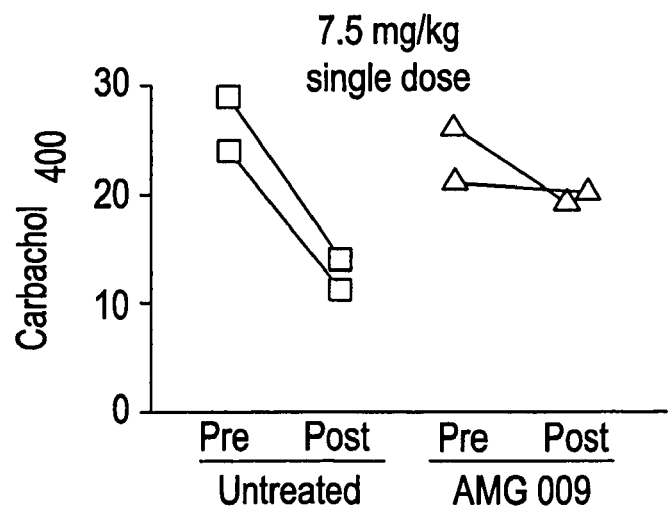
Figure 2A:
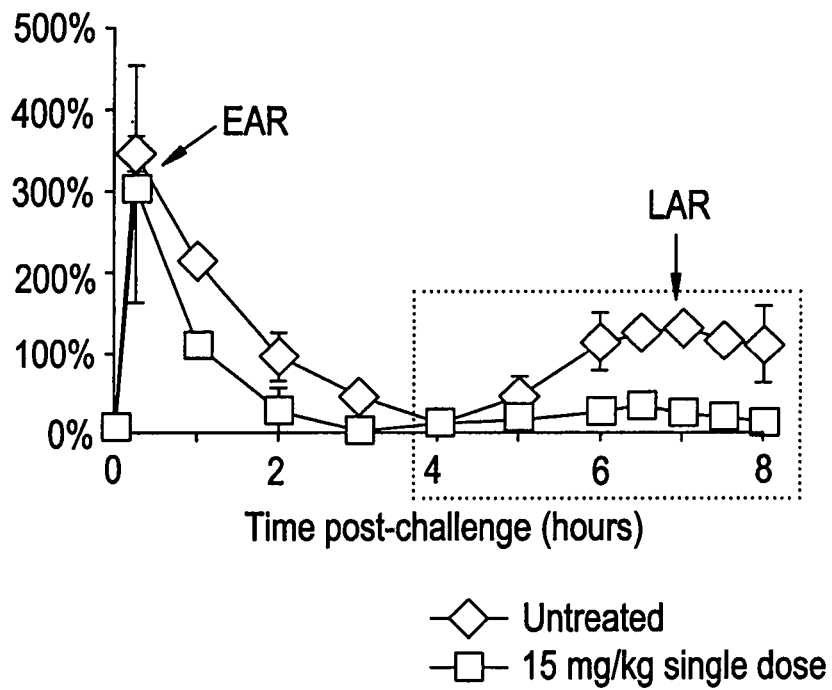
FIGS. 2A and 2B are graphs showing data obtained demonstrating the efficacy of AMG 009 (when dosed at 15 mg/kg single dose) in the Sheep Airway Response Model of Asthma.
Figure 2B:
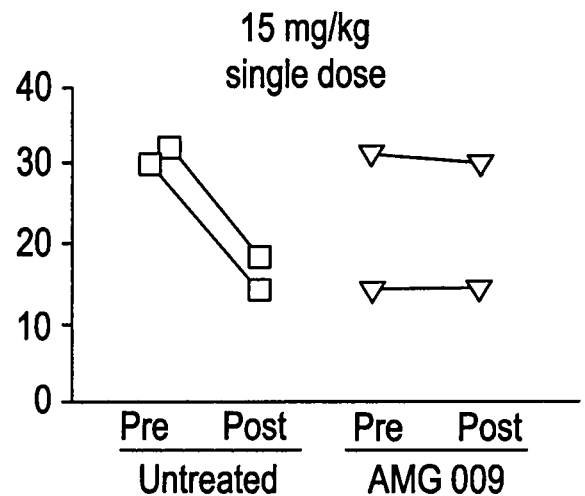
Figure 3A:
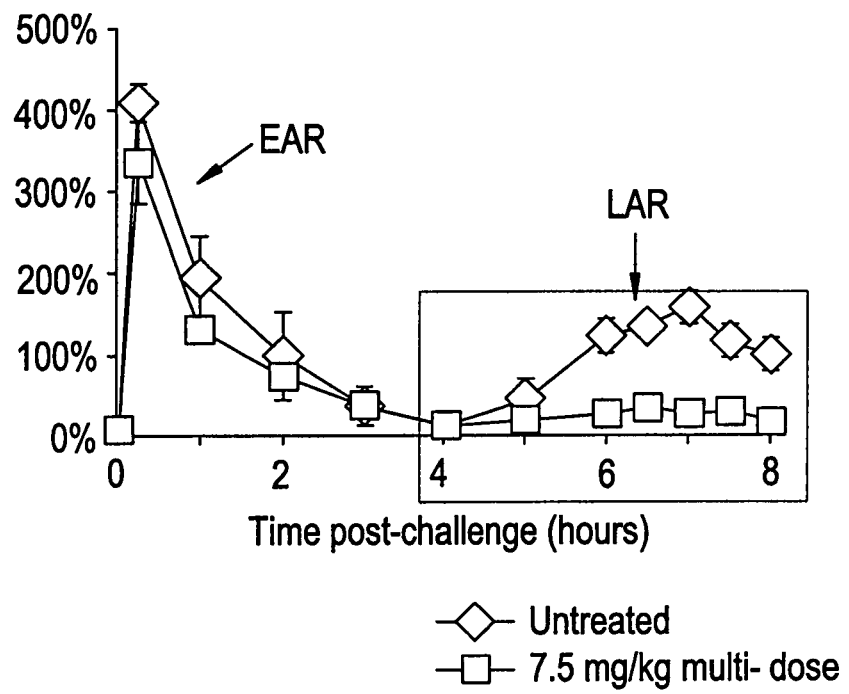
FIGS. 3A and 3B are graphs showing data obtained demonstrating the efficacy of AMG 009 (when dosed at 7.5 mg/kg multi-dose) in the Sheep Airway Response Model of Asthma.
Figure 3B:
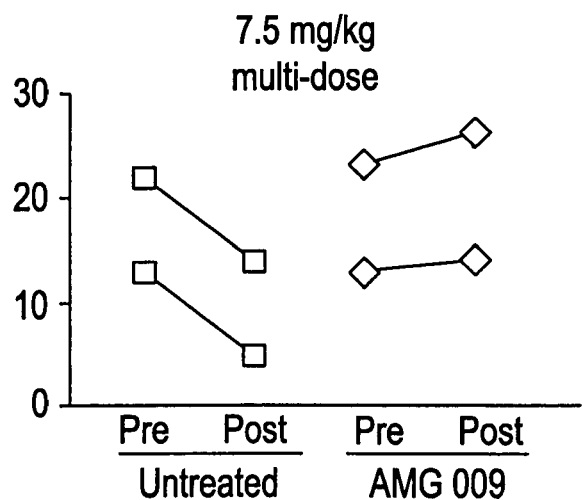
Figure 4A:
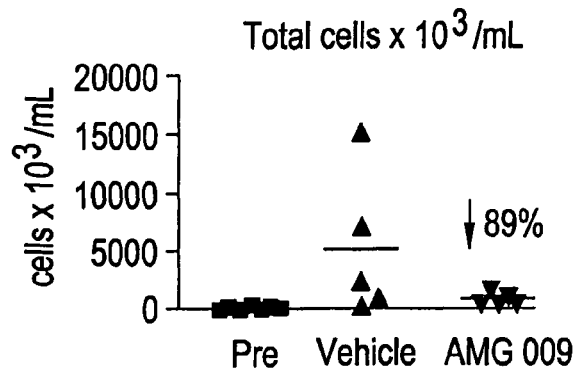
FIGS. 4A, 4B, 4C, 4D, 4E, and 4F are graphs showing further Sheep Model data demonstrating that AMG 009 was effective in blocking the recruitment of various inflammatory cells to the lungs of sheep.
Figure 4B:
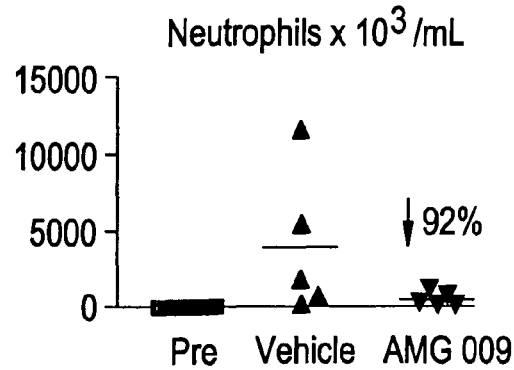
Figure 4C:
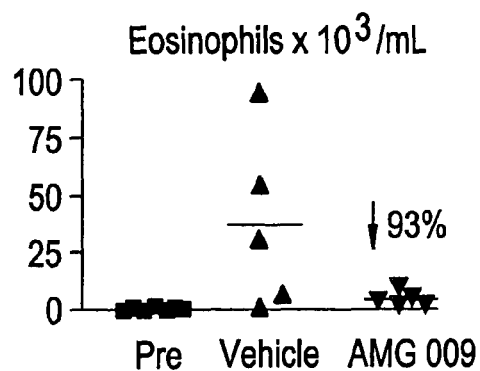
Figure 4D:
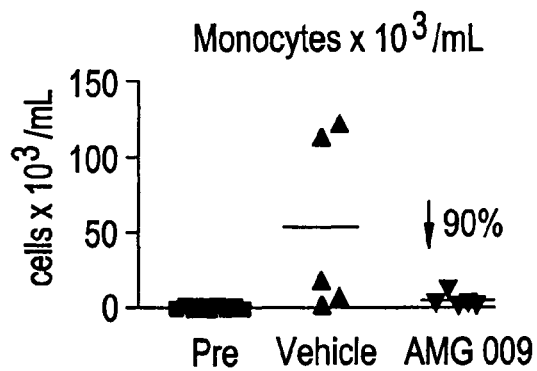
Figure 4E:
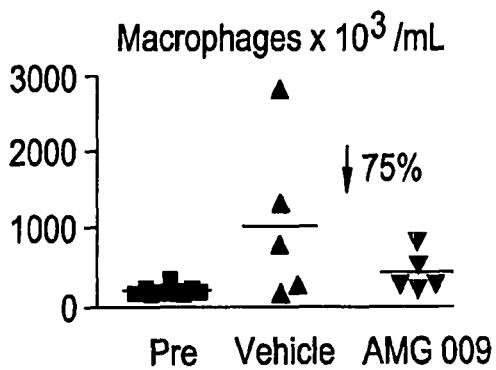
Figure 4F:
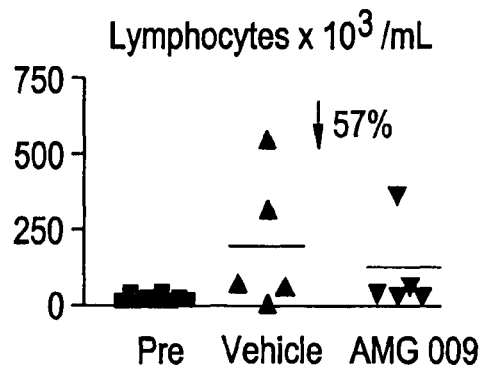
Figure 6A:
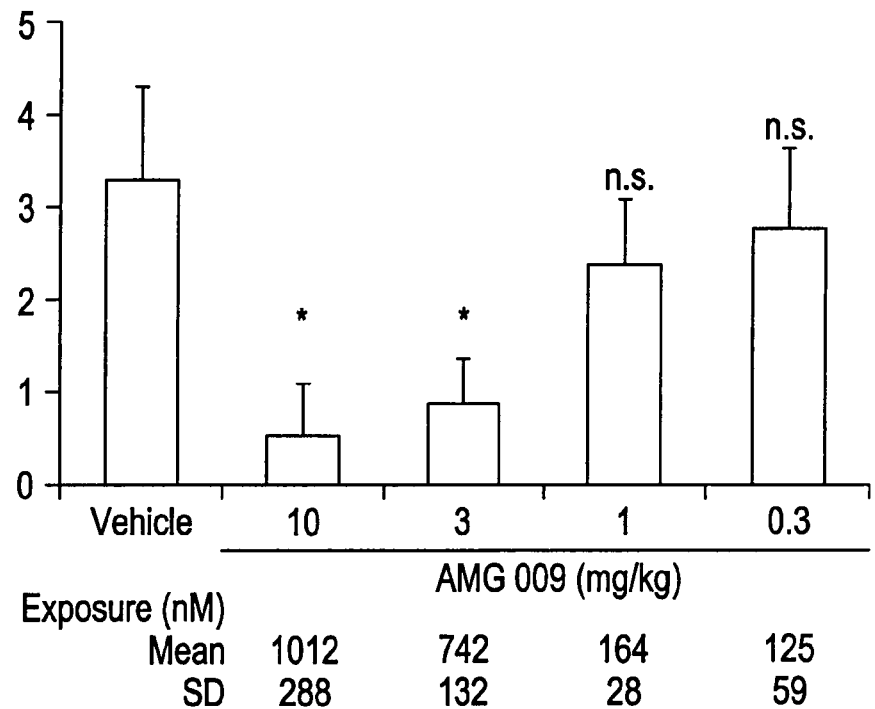
FIGS. 6A and 6B are graphs comparing the efficacy of AMG 009 (FIG. 6A) and Example Compound 14 (FIG. 6A) in the Guinea Pig Model of airway constriction.
Figure 6B:
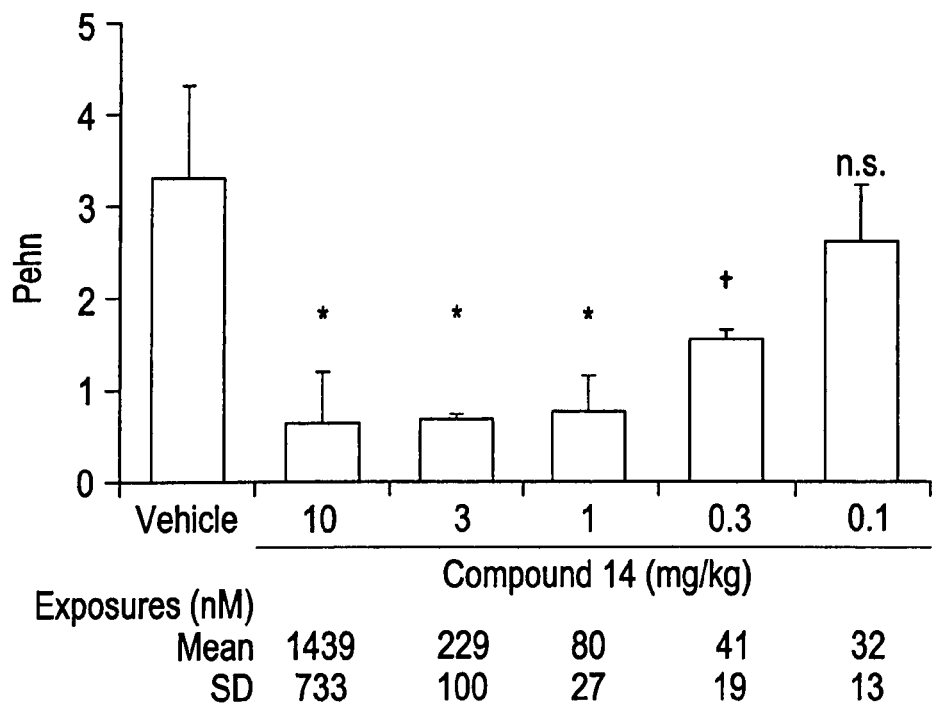

The sheep and guinea pig models employed herein are disclosed in publications such as Abraham, W. M., *Sheep Models of Allergic Bronchoconstriction*)(in *Allergy and Allergic Disease* 2:1045 1977); Isenberg-Feig, H et al., *Animal Models of Allergic Asthma* (in *Current Allergy and Asthma Reports* 2003, 3:70-78); Abraham, W. M., et al. *Am J Respir Crit. Care Med* vol. 159. pp. 1205-1214, 1999; Abraham, W. M. et al, *Am J Respir Crit. Care Med* vol. 169. pp. 97-104, 2004; and Jones, T. R. et al *Can. J. Physiol. Pharmacol.* 73: 191-201 1995.

DETAILED DESCRIPTION OF THE INVENTION

Abbreviations and Definitions

The abbreviations used herein are conventional, unless otherwise defined.

The terms "treat", "treating" and "treatment", as used herein, are meant to include alleviating or abrogating a disease and/or its attendant symptoms a and alleviating or eradicating the cause of the disease itself.

The terms "prevent", "preventing" and "prevention", as used herein, refer to a method of delaying or precluding the onset of a disease and/or its attendant symptoms, barring a subject from acquiring a disease or reducing a subject's risk of acquiring a disease.

The term "therapeutically effective amount" refers to the amount of the subject compound that will elicit the biological or medical response of a tissue, system, animal or human that is being sought by the researcher, veterinarian, medical doctor or other clinician. The term "therapeutically effective amount" includes that amount of a compound that, when administered, is sufficient to prevent development of, or alleviate to some extent, one or more of the symptoms of the condition or disorder being treated. The therapeutically effective amount will vary depending on the compound, the disease and its severity and the age, weight, etc., of the mammal to be treated.

The "subject" is defined herein to include animals such as mammals, including, but not limited to, primates (e.g., humans), cows, sheep, goats, horses, dogs, cats, rabbits, rats, mice and the like. In preferred embodiments, the subject is a human.

As used herein, the term "CRTH2" refers to a CRTH2 protein or variant thereof that is capable of mediating a cellular response to PGD$_2$ in vitro or in vivo. CRTH2 variants include proteins substantially homologous to native CRTH2, i.e., proteins having one or more naturally or non-naturally occurring amino acid deletions, insertions or substitutions (e.g., CRTH2 derivatives, homologs and fragments). The amino acid sequence of CRTH2 variant preferably is at least about 80% identical to a native CRTH2, more preferably at least about 90% identical, and most preferably at least about 95% identical.

As used herein, the terms "other PGD$_2$ receptor", "another PGD$_2$ receptor" and the like refer to a prostanoid receptor protein other than CRTH2, or variant thereof, that is capable of mediating a cellular response to PGD$_2$ in vitro or in vivo. Another PGD$_2$ receptor may be selective for PGD$_2$ (e.g., DP) or other one or more other prostanoids (e.g., EP$_1$, EP$_2$, EP$_3$ and EP$_4$, FP, IP and TP). Other PGD$_2$ receptor variants include proteins substantially homologous to a corresponding native prostanoid receptor other than CRTH2, i.e., proteins having one or more naturally or non-naturally occurring amino acid deletions, insertions or substitutions (e.g., derivatives, homologs and fragments of another PGD$_2$ receptor). The amino acid sequence of other PGD$_2$ receptor variants preferably is at least about 80% identical to the corresponding native other PGD$_2$ receptors, more preferably at least about 90% identical, and most preferably at least about 95% identical.

The terms "modulate", "modulation" and the like refer to the ability of a compound to increase or decrease the function and/or expression of CRTH2 and/or one or more other PGD$_2$ receptors, where such function may include transcription regulatory activity and/or protein-binding. Modulation may occur in vitro or in vivo. Modulation, as described herein, includes the inhibition, antagonism, partial antagonism, activation, agonism or partial agonism of a function or characteristic associated with CRTH2 and/or one or more other PGD$_2$ receptors, either directly or indirectly, and/or the upregulation or downregulation of the expression of CRTH2 and/or one or more other PGD$_2$ receptors, either directly or indirectly. In a preferred embodiment, the modulation is direct. Inhibitors or antagonists are compounds that, e.g., bind to, partially or totally block stimulation, decrease, prevent, inhibit, delay activation, inactivate, desensitize, or downregulate signal transduction. Activators or agonists are compounds that, e.g., bind to, stimulate, increase, open, activate, facilitate, enhance activation, activate, sensitize or upregulate signal transduction. The ability of a compound to inhibit the function of CRTH2 and/or one or more other PGD$_2$ receptors can be demonstrated in a biochemical assay, e.g., binding assay, or a cell-based assay, e.g., a transient transfection assay.

The term "CRTH2-modulating amount" refers to that amount of a compound that is needed to produce a desired effect in any one of the cell-based assays, biochemical assays or animal models described herein. Typically, a CRTH2-modulating amount of a compound will be at least that amount which exhibits an EC$_{50}$ in a reporter-gene cell-based assay (relative to an untreated control).

As used herein, the terms "CRTH2-responsive condition or disorder", "condition or disorder responsive to CRTH2" and related terms and phrases refer to a condition or disorder associated with inappropriate, e.g., less than or greater than normal, CRTH2 activity and at least partially responsive to or affected by CRTH2 modulation (e.g., a CRTH2 antagonist or agonist results in some improvement in patient well-being in at least some patients). Inappropriate CRTH2 functional activity might arise as the result of CRTH2 expression in cells which normally do not express CRTH2, increased CRTH2 expression or degree of intracellular activation (leading to, e.g., inflammatory and immune-related disorders and diseases) or decreased CRTH2 expression. A CRTH2-associated condition or disorder may include a CRTH2-mediated condition or disorder.

As used herein, the phrases "CRTH2-mediated condition or disorder", "a condition or disorder mediated by CRTH2" and related phrases and terms refer to a condition or disorder characterized by inappropriate, e.g., less than or greater than normal, CRTH2 activity. Inappropriate CRTH2 functional activity might arise as the result of CRTH2 expression in cells which normally do not express CRTH2, increased CRTH2 expression or degree of intracellular activation (leading to, e.g., inflammatory and immune-related disorders and diseases) or decreased CRTH2 expression. A CRTH2-mediated condition or disorder may be completely or partially mediated by inappropriate CRTH2 functional activity. However, a CRTH2-mediated condition or disorder is one in which modulation of CRTH2 results in some effect on the underlying condition or disorder (e.g., an CRTH2 antagonist or agonist results in some improvement in patient well-being in at least some patients).

The term "PGD$_2$ receptor-modulating amount" and related terms and phrases refers to that amount of a compound that is needed to produce a desired effect in any one of the cell-based assays, biochemical assays or animal models described herein. Typically, a PGD$_2$ receptor-modulating amount of a compound will be at least that amount which exhibits an EC$_{50}$ in a reporter-gene cell-based assay (relative to an untreated control).

As used herein, the term "condition or disorder responsive to another PGD$_2$ receptor" and related terms and phrases refer to a condition or disorder associated with inappropriate, e.g., less than or greater than normal, activity of another PGD$_2$ receptor and at least partially responsive to or affected by modulation of another PGD$_2$ receptor (e.g., another PGD$_2$ receptor antagonist or agonist results in some improvement in patient well-being in at least some patients). Inappropriate functional activity of another PGD$_2$ receptor might arise as the result of expression of another PGD$_2$ receptor in cells which normally do not express the receptor, increased expression of another PGD$_2$ receptor or degree of intracellular activation (leading to, e.g., inflammatory and immune-related disorders and diseases) or decreased expression of another PGD$_2$ receptor. A condition or disorder associated with another PGD$_2$ receptor may include a condition or disorder mediated by another PGD$_2$ receptor.

As used herein, the phrase "condition or disorder mediated by another PGD$_2$ receptor" and related phrases and terms refer to a condition or disorder characterized by inappropriate, e.g., less than or greater than normal, activity of another PGD$_2$ receptor. Inappropriate functional activity of another PGD$_2$ receptor might arise as the result of expression of another PGD$_2$ receptor in cells which normally do not express the receptor, increased expression of another PGD$_2$ receptor or degree of intracellular activation (leading to, e.g., inflammatory and immune-related disorders and diseases) or decreased expression of another PGD$_2$ receptor. A CRTH2-mediated condition or disorder may be completely or partially mediated by inappropriate functional activity of another PGD$_2$ receptor. However, a condition or disorder mediated by of another PGD$_2$ receptor is one in which modulation of another PGD$_2$ receptor results in some effect on the underlying condition or disorder (e.g., another PGD$_2$ receptor antagonist or agonist results in some improvement in patient well-being in at least some patients).

The term "alkyl," by itself or as part of another substituent, means, unless otherwise stated, a straight or branched chain, or combination thereof, which is fully saturated. Preferred alkyl groups have 1 to 8 carbon atoms (i.e. $C_1$-$C_8$). More preferred alkyl groups have 1 to 6 carbon atoms (i.e. $C_1$-$C_6$). Examples of alkyl groups include methyl, ethyl, n-propyl, isopropyl, n-butyl, t-butyl, isobutyl, sec-butyl, n-pentyl, n-hexyl, n-heptyl, n-octyl, homologs and the like.

The term "heteroalkyl" refers to alkyl groups wherein one or more carbon atoms is substituted with a heteroatom selected from nigrogen, oxygen or sulfur.

The terms "alkoxy," and "haloalkoxy" are used in their conventional sense, and refer to those alkyl groups, and haloalkyl groups, attached to the remainder of the molecule via an oxygen atom.

The term "cycloalkyl" by itself or in combination with other terms, represents, unless otherwise stated, cyclic versions of "alkyl". Preferred cycloalkyl groups have 3 to 8 carbon atoms (i.e. $C_3$-$C_8$). More preferred alkyl groups have 3 to 6 carbon atoms (i.e. $C_3$-$C_6$). Examples of cycloalkyl include cyclopropyl, cyclobutyl, cyclopentyl, cyclohexyl, 1-cyclohexenyl, 3-cyclohexenyl, cycloheptyl, and the like.

The terms "halo" or "halogen," by themselves or as part of another substituent, mean, unless otherwise stated, a fluorine, chlorine, bromine, or iodine atom. Additionally, terms such as "haloalkyl", are meant to include alkyl substituted with halogen atoms which can be the same or different, in a number ranging from one to (2m'+1), where m' is the total number of carbon atoms in the alkyl group. For example, the term "halo ($C_1$-$C_4$)alkyl" is meant to include trifluoromethyl, 2,2,2-trifluoroethyl, 4-chlorobutyl, 3-bromopropyl, and the like. Thus, the term "haloalkyl" includes monohaloalkyl (alkyl substituted with one halogen atom) and polyhaloalkyl (alkyl substituted with halogen atoms in a number ranging from two to (2m'+1) halogen atoms). The term "perhaloalkyl" means, unless otherwise stated, alkyl substituted with (2m'+1) halogen atoms, where m' is the total number of carbon atoms in the alkyl group. For example, the term "perhalo($C_1$-$C_4$)alkyl", is meant to include trifluoromethyl, pentachloroethyl, 1,1,1-trifluoro-2-bromo-2-chloroethyl, and the like.

The term "aryl" means, unless otherwise stated, a polyunsaturated, typically aromatic, hydrocarbon substituent which can be a single ring or multiple rings (up to three rings) which are fused together or linked covalently. The term "heteroaryl" refers to aryl groups (or rings) that contain from one to four heteroatoms selected from the group consisting of N, O and S, wherein the nitrogen and sulfur atoms are optionally oxidized, and the nitrogen atom(s) are optionally quaternized. A heteroaryl group can be attached to the remainder of the molecule through a heteroatom. Non-limiting examples of aryl and heteroaryl groups include phenyl, 1-naphthyl, 2-naphthyl, 4-biphenyl, 1-pyrrolyl, 2-pyrrolyl, 3-pyrrolyl, 3-pyrazolyl, 2-imidazolyl, 4-imidazolyl, pyrazinyl, 2-oxazolyl, 4-oxazolyl, 2-phenyl-4-oxazolyl, 5-oxazolyl, 3-isoxazolyl, 4-isoxazolyl, 5-isoxazolyl, 2-thiazolyl, 4-thiazolyl, 5-thiazolyl, 2-furyl, 3-furyl, 2-thienyl, 3-thienyl, 2-pyridyl, 3-pyridyl, 4-pyridyl, 2-pyrimidyl, 4-pyrimidyl, 2-pyrimidinyl, 4-pyrimidinyl, 5-pyrimidinyl, 3-pyridazinyl, 4-pyridazinyl, 5-benzothiazolyl, purinyl, 2-benzimidazolyl, 5-indolyl, 1H-indazole, carbazole, □-carboline, □-carboline, □-carboline, 1-isoquinolyl, 5-isoquinolyl, 2-quinoxalinyl, 5-quinoxalinyl, 2-quinolyl, 3-quinolyl, 4-quinolyl, 5-quinolyl, 6-quinolyl, 7-quinolyl and 8-quinolyl.

Preferably, the term "aryl" refers to a phenyl or naphthyl group which is unsubstituted or substituted. Preferably, the term "heteroaryl" refers to a pyrrolyl, pyrazolyl, imidazolyl, pyrazinyl, oxazolyl, isoxazolyl, thiazolyl, furyl, thienyl, pyridyl, pyrimidyl, benzothiazolyl, purinyl, benzimidazolyl, indolyl, isoquinolyl, quinoxalinyl, quinoxalinyl, quinolyl or quinolyl group which is unsubstituted or substituted.

For brevity, the term "aryl" when used in combination with other terms (e.g., aryloxy, arylthioxy, arylalkyl) includes both aryl and heteroaryl rings as defined above. Thus, the term "arylalkyl" is meant to include those radicals in which an aryl group is attached to an alkyl group (e.g., benzyl, phenethyl, pyridylmethyl and the like) including those alkyl groups in which a carbon atom (e.g., a methylene group) has been replaced by, for example, an oxygen atom (e.g., phenoxymethyl, 2-pyridyloxymethyl, 3-(1-naphthyloxy)propyl, and the like).

Each of the above terms (e.g., "alkyl," "aryl" and "heteroaryl") is meant to include both substituted and unsubstituted forms of the indicated radical, unless otherwise indicated. Preferred substituents for each type of radical are provided below.

Substituents for the alkyl radicals (as well as those groups referred to as alkylene, alkenyl, heteroalkylene, heteroalkenyl, alkynyl, cycloalkyl, heterocycloalkyl, cycloalkenyl and heterocycloalkenyl) can be a variety of groups selected from: —OR', =O, =NR', =N—OR', —NR'R", —SR', halogen, —SiR'R"R'", —OC(O)R', —C(O)R', —CO₂R', —CONR'R", —OC(O)NR'R", —NR"C(O)R', —NR'—C(O) NR"R'", —NR'—SO₂NR"R'", —NR"CO₂R', —NH—C(NH₂)=NH, —NR'C(NH₂)=NH, —NH—C(NH₂)=NR', —S(O)R', —SO₂R', —SO₂NR'R", —NR"SO₂R, —CN and —NO₂, in a number ranging from zero to three, with those groups having zero, one or two substituents being particularly preferred. R', R" and R'" each independently refer to hydrogen, unsubstituted ($C_1$-$C_8$)alkyl and heteroalkyl, unsubstituted aryl, aryl substituted with one to three halogens, unsubstituted alkyl, alkoxy or thioalkoxy groups, or aryl-($C_1$-$C_4$) alkyl groups. When R' and R" are attached to the same nitrogen atom, they can be combined with the nitrogen atom to form a 5-, 6- or 7-membered ring. For example, —NR'R" is meant to include 1-pyrrolidinyl and 4-morpholinyl. Typically, an alkyl or heteroalkyl group will have from zero to three substituents, with those groups having two or fewer substituents being preferred in the present invention. More preferably, an alkyl or heteroalkyl radical will be unsubstituted or monosubstituted. Most preferably, an alkyl or heteroalkyl radical will be unsubstituted. From the above discussion of substituents, one of skill in the art will understand that the term "alkyl" is meant to include groups such as trihaloalkyl (e.g., —$CF_3$ and —$CH_2CF_3$).

Preferred substituents for the alkyl radicals are selected from: —OR', =Q, —NR'R", —SR', halogen, —SiR'R"R'", —OC(O)R', —C(O)R', —CO₂R', —CONR'R", — OC(O) NR'R", —NR"C(O)R', —NR'CO₂R', —NR'—SO₂NR"R'", —S(O)R', —SO₂R', —SO₂NR'R", —NR"SO₂R, —CN and —NO₂, where R' and R" are as defined above. Further preferred substituents are selected from: —OR', =O, —NR'R", halogen, —OC(O)R', —CO₂R', —CONR'R", —OC(O) NR'R", —NR"C(O)R', —NR'CO₂R', —NR'—SO₂NR"R'", —SO₂R', —SO₂NR'R", —NR"SO₂R', —CN and —NO₂.

Similarly, substituents for the aryl and heteroaryl groups are varied and are selected from: -halogen, —OR, —OC(O) R', —NR'R", —SR', —R', —CN, —NO₂, —CO₂R', —CONR'R", —C(O)R', —OC(O)NR'R", —NR"C(O)R', —NR"C(O)₂R', —NR'—C(O)NR"R'", —NH—C(NH₂)=NH, —NR'C(NH₂)=NH, —NH—C(NH₂)=NR', —S(O) R', —S(O)₂R', —S(O)₂NR'R", —N₃, —CH(Ph)₂, perfluoro ($C_1$-$C_4$)alkoxy, and perfluoro($C_1$-$C_4$)alkyl, in a number ranging from zero to the total number of open valences on the aromatic ring system; and where R', R" and R'" are independently selected from hydrogen, $(C_1-C_8)$alkyl and heteroalkyl, unsubstituted aryl and heteroaryl, (unsubstituted aryl)-$(C_1-C_4)$alkyl, and (unsubstituted aryl)oxy-$(C_1-C_4)$alkyl.

Two of the substituents on adjacent atoms of the aryl or heteroaryl ring may optionally be replaced with a substituent of the formula —T—C(O)—$(CH_2)_q$—U—, wherein T and U are independently —NH—, —O—, —$CH_2$— or a single bond, and q is an integer of from 0 to 2. Alternatively, two of the substituents on adjacent atoms of the aryl or heteroaryl ring may optionally be replaced with a substituent of the formula —A—$(CH_2)_r$—B—, wherein A and B are independently —$CH_2$—, —O—, —NH—, —S—, —S(O)—, —$S(O)_2$—, —$S(O)_2NR'$— or a single bond, and r is an integer of from 1 to 3. One of the single bonds of the new ring so formed may optionally be replaced with a double bond. Alternatively, two of the substituents on adjacent atoms of the aryl or heteroaryl ring may optionally be replaced with a substituent of the formula —$(CH_2)_n$—X—$(CH_2)_n$—, where s and t are independently integers of from 0 to 3, and X is —O—, —NR'—, —S—, —S(O)—, —$S(O)_2$—, or —$S(O)_2NR'$—. The substituent R' in —NR'— and —$S(O)_2NR'$— is selected from hydrogen or unsubstituted $(C_1-C_6)$alkyl.

As used herein, the term "heteroatom" is meant to include oxygen (O), nitrogen (N), sulfur (S) and silicon (Si).

The term "transition metal catalyst", as used herein, comprises two components: a transition metal source, and a ligand. The ligand can be either complexed together with the transition metal source, or the ligand can be independently introduced into the reaction vessel with the transition metal source. The active form of the transition metal catalyst is not well characterized. Therefore, it is contemplated that the term "transition metal catalyst", as used herein, shall include any catalytic transition metal and/or catalyst precursor as it is introduced into the reaction vessel and which is, if necessary, converted in situ into the active form, as well as the active form of the catalyst which participates in the reaction. In general, any transition metal (i.e., selected from Groups 3-12 of the periodic table or from the lanthanide series) may be used to form the catalyst. However, in preferred embodiments, the metal will be selected from the group of late transition metals, preferably from Groups 5-12, and more preferably from Groups 7-11. Preferred transition metals include platinum, palladium, iron, nickel, ruthenium, rhodium and copper. More preferred transition metals include nickel, palladium and copper. Palladium is the most preferred transition metal.

Suitable transition metal catalyst include soluble or insoluble complexes of platinum, palladium, nickel and copper. Suitable complexes include, but are not limited to, Pd/C, $PdCl_2$, $Pd(OAc)_2$, $(CH_3CN)_2PdCl_2$, $Pd[P(C_6H_5)_3]_4$, tris(dibenzylideneacetone)dipalladium $[Pd_2(dba)_3]$, bis(dibenzylideneacetone)palladium $[Pd(dba)_2]$, allylpalladium(II) chloride $[(\eta^3-C_3H_5)_2Pd_2Cl_2]$, CuCuI, $Ni(acac)_2$, $NiCl_2-[P(C_6H_5)]_2$, $Ni(1,5-cyclooctadiene)_2$, $Ni(1,10-phenanthroline)_2$, $Ni(dppf)_2$, $NiCl_2(dppf)$, $NiCl_2(1-10-phenanthroline)$, Raney nickel and the like, wherein "acac" represents acetylacetonate.

The term "ligand", as used herein, includes chelating ligands, such as, by way of example, alkyl and aryl derivatives of phosphines and biphospines, amines, diamines, imines, arsines and hybrids thereof, including hybrids of phosphines with amines. Weakly or non-nucleophilic stabilizing ions are preferred to avoid undesired side reactions involving the counterion. In preferred embodiments the ligand includes one or more phosphine or aminophosphine ligands. Phosphine ligands are commercially available or can be prepared by methods known to those of skill in the art. The phosphines can be monodentate phosphine ligands (such as trimethylphosphine, triethylphosphine, tripropylphosphine, triisopropylphosphine, tributylphosphine, tricyclohexylphoshpine, triphenylphosphine ("$PCy_3$"), tri(o-tolyl)phosphine, trimethylphosphite, triethylphosphite, tripropylphosphite, triisopropylphosphite, tributylphosphite, tricyclohexylphoshpite, triphenylphosphite, tri(o-tolyl)phosphine, 4,5-bis(diphenylphosphino)-9,9-dimethyl-9H-xanthene ("Xantphos"), t-butyl 2-di-tertbutylphosphino-2',4',6'-triisopropyl-1,1'-biphenyl ("t-Bu-X-Phos"), and the like), or bidentate phoshine ligands (such as 2,2'-bis(diphenylphosphino)-1,1'-binapthyl (BINAP), 1,2-bis(dimethylphosphino)ethane, 1,2-bis(diethylphosphino)ethane, 1,2-bis(dipropylphosphino)ethane, 1,2-bis(diisopropylphosphino)ethane, 1,2-bis(dibutylphosphino)ethane, 1,2-bis(dicyclohexylphosphino)ethane, 1,3-bis(dicyclohexylphosphino)propane, 1,3-bis(dicisopropylphosphino)propane, 1,4-bis(diisopropylphosphino)butane, 2,4-bis(dicyclohexylphosphino)pentate, and the like), or ligands such as those disclosed in *Organic Letters* 2000, Vol. 2, No. 8, pp. 1101-1104, and in *Journal of the American Chemical Society* 2002, Vol. 124, pp. 6043-6048, or similar analogues within the knowledge of persons skilled in the art of chemical synthesis. Preferred ligands include Xanthpos, $PCy_3$, t-Bu-X-Phos, and the like.

Suitable ligands may further include heteroaryl phosphines such as 2-(di-tert-butylphosphino)-1-(2-methoxyphenyl)-1H-indole, 2-(di-tert-butylphosphino)-1-(2-methoxyphenyl)-1H-pyrrole, 1-(2-methoxyphenyl)-2-methyl-1H-pyrrole, 5-(di-tert-butylphosphino)-1-(1,3,5-triphenyl-1H-pyrazol-4-yl)-1H-pyrazole, and similar analogues.

The term "base" as used herein includes fluorides, amines, hydroxides, carbonates, phosphates, alkoxides, metal amides and carbanions. Preferred bases include carbonates (especially cesium carbonate) and phosphates (especially potassium phosphate).

The term "acid" as used herein refers to compounds which are hydrogen donors, such as acetic acid, hydrochloric acid, hydrogen fluoride, sulfuric acid, nitric acid, trifilic acid, trifluoroacetic acid ("TFA"), and the like.

The term "reductant" is intended to encompass compounds that have reduction potential to cleave C—O bond and deliver $H_2$. The term reductant includes borane, hydrogen boride, organosilanes, organogermanes, organostannanes, phosphites, hypophosphite, sulfites, thiosulfate, bisulfite, hydrosulfite, formats. The term is intended to electrochemical reduction.

The term "metal iodide salt" is intended to refer to a salt comprising a stoichiometric combination of iodo anion $(I^{-1})$ and metal cation, where the metal is selected from either the Alkaline or Alkaline Earth family. Preferred metal iodide salts include sodium iodide.

"Elevated Temperature" refers to temperatures above 25° C.

"Inert atmosphere" refers to reaction conditions conducted under nitrogen which is supplied to the reaction container under positive pressure.

References to data obtained using "DSC" or "Differential Scanning Calorimetry" refer to DSC measurements obtained using a heating rate of 10° C. per minute under standard conditions deemed generally acceptable by those of ordinary skill in the art.

A "thermal transition" observed in DSC experiments includes both endothermic transitions and exothermic transitions.

References to "2-theta" values obtained from Powder X-Ray Diffraction spectroscopy, refer to values obtained when using Copper Kα radiation as the radiation source, under conditions deemed generally acceptable to those of skill in the art.

The term "about" when used in conjunction with "° C." is intended to provide a margin of error of ±0.25. The term "about" when used in conjunction with 2-theta values in powder X-Ray diffraction patterns is intended to provide a margin of error of +0.1.

The term "pharmaceutically acceptable salts" is meant to include salts of the active compounds which are prepared with relatively nontoxic acids or bases, depending on the particular substituents found on the compounds described herein. When compounds of the invention contain relatively acidic functionalities, base addition salts can be obtained by contacting the neutral form of such compounds with a sufficient amount of the desired base, either neat or in a suitable inert solvent. Examples of pharmaceutically acceptable base addition salts include sodium, potassium, calcium, ammonium, organic amino, or magnesium salt, or a similar salt. When compounds of the invention contain relatively basic functionalities, acid addition salts can be obtained by contacting the neutral form of such compounds with a sufficient amount of the desired acid, either neat or in a suitable inert solvent. Examples of pharmaceutically acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived from relatively nontoxic organic acids like acetic, propionic, isobutyric, maleic, malonic, benzoic, succinic, suberic, fumaric, mandelic, phthalic, benzenesulfonic, p-tolylsulfonic, citric, tartaric, methanesulfonic, and the like. Also included are salts of amino acids such as arginate and the like, and salts of organic acids like glucuronic or galacturonic acids and the like (see, for example, Berge et al. (1977) *J. Pharm. Sci.* 66:1-19). Certain specific compounds of the invention contain both basic and acidic functionalities that allow the compounds to be converted into either base or acid addition salts.

The neutral forms of the compounds may be regenerated by contacting the salt with a base or acid and isolating the parent compound in the conventional manner. The parent form of the compound differs from the various salt forms in certain physical properties, such as solubility in polar solvents, but otherwise the salts are equivalent to the parent form of the compound for the purposes of the invention.

In addition to salt forms, the invention provides compounds which are in a prodrug form. Prodrugs of the compounds described herein are those compounds that readily undergo chemical changes under physiological conditions to provide the compounds of the invention. Additionally, prodrugs can be converted to the compounds of the invention by chemical or biochemical methods in an ex vivo environment. For example, prodrugs can be slowly converted to the compounds of the invention when placed in a transdermal patch reservoir with a suitable enzyme or chemical reagent. Prodrugs are often useful because, in some situations, they may be easier to administer than the parent drug. They may, for instance, be bioavailable by oral administration whereas the parent drug is not. The prodrug may also have improved solubility in pharmaceutical compositions over the parent drug. A wide variety of prodrug derivatives are known in the art, such as those that rely on hydrolytic cleavage or oxidative activation of the prodrug. An example, without limitation, of a prodrug would be a compound of the invention which is administered as an ester (the "prodrug"), but then is metabolically hydrolyzed to the carboxylic acid, the active entity. Additional examples include peptidyl derivatives of a compound of the invention.

Certain compounds of the invention can exist in unsolvated forms as well as solvated forms, including hydrated forms. In general, the solvated forms are equivalent to unsolvated forms and are intended to be encompassed within the scope of the invention. Certain compounds of the invention may exist in multiple crystalline or amorphous forms. In general, all physical forms are equivalent for the uses contemplated by the invention and are intended to be within the scope of the invention.

Certain compounds of the invention possess asymmetric carbon atoms (optical centers) or double bonds; the racemates, enantiomers, diastereomers, geometric isomers and individual isomers are all intended to be encompassed within the scope of the invention. These isomers can be resolved or asymmetrically synthesized using conventional methods to render the isomers "optically pure", i.e., substantially free of its other isomers.

The compounds of the invention may also contain unnatural proportions of atomic isotopes at one or more of the atoms that constitute such compounds. For example, the compounds may be radiolabeled with radioactive isotopes, such as for example tritium ($^3H$), iodine-125 ($^{125}I$) or carbon-14 ($^{14}C$). Radiolabled compounds are useful as therapeutic or prophylactic agents, e.g., cancer therapeutic agents, research reagents, e.g., CRTH2 assay reagents, and diagnostic agents, e.g., in vivo imaging agents. All isotopic variations of the compounds of the invention, whether radioactive or not, are intended to be encompassed within the scope of the invention.

EMBODIMENTS OF THE INVENTION

A class of compounds that modulate CRTH2 and/or one or more other $PGD_2$ receptors has been discovered. Depending on the biological environment (e.g., cell type, pathological condition of the host, etc.), these compounds can activate or inhibit the actions of CRTH2 and/or one or more other $PGD_2$ receptors (e.g., ligand binding). By activating or inhibiting CRTH2 and/or one or more other $PGD_2$ receptors, the compounds will find use as therapeutic agents capable of modulating diseases and conditions responsive to modulation of CRTH2 and/or one or more other $PGD_2$ receptors and/or mediated by CRTH2 and/or one or more other $PGD_2$ receptors. As noted above, examples of such diseases and conditions include asthma, allergic rhinitis, eczema, psoriasis, atopic dermatitis, fever, sepsis, systemic lupus erythematosus, diabetes, rheumatoid arthritis, multiple sclerosis, atherosclerosis, transplant rejection, inflammatory bowel disease and cancer. Additionally, the compounds are useful for the treatment and/or prevention of complications of these diseases and disorders (e.g., cardiovascular disease).

While the compounds of the invention are believed to exert their effects by interacting with CRTH2, the mechanism of action by which the compounds act is not a limiting embodiment of the invention. For example, compounds of the invention may interact with $PGD_2$ receptor subtypes other than CRTH2, e.g., DP receptor, and/or other prostanoid receptors, e.g., thromboxane $A_2$ ($TXA_2$) receptor. Indeed, as alluded to above, the present invention specifically contemplates the use of the disclosed compounds to modulate one or more $PGD_2$ receptors other than CRTH2.

Compounds contemplated by the invention include, but are not limited to, the exemplary compounds provided herein.

Compounds

In one aspect, the invention provides compounds of formula (I):

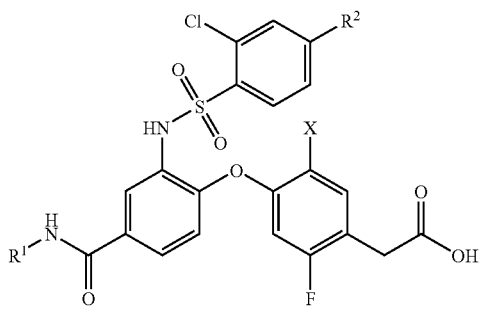

I and salts thereof
wherein
R¹ is alkyl or cycloalkyl;
R² is halo, alkyl, haloalkyl, alkoxy, haloalkoxy or cycloalkyl; and
X is chloro or fluoro.

Preferred compounds within the scope of Formula I include compounds where X is chloro.

Preferred compounds within the scope of Formula I further include compounds where R¹ is alkyl, ($C_1$-$C_5$ alkyl more preferred) (t-butyl most preferred).

Preferred compounds within the scope of Formula I further include compounds where R² is cycloalkyl, ($C_3$-$C_5$ cycloalkyl more preferred) (cyclopropyl especially preferred).

Preferred compounds within the scope of Formula I include the following compounds:

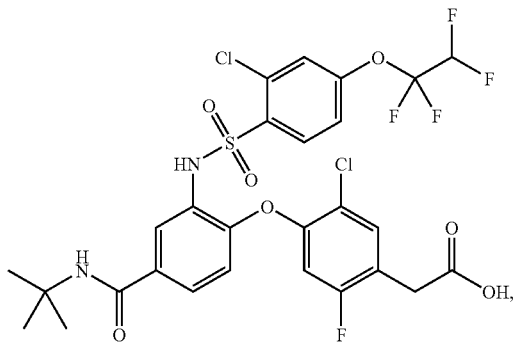

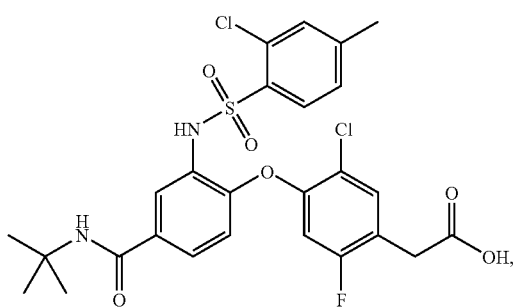

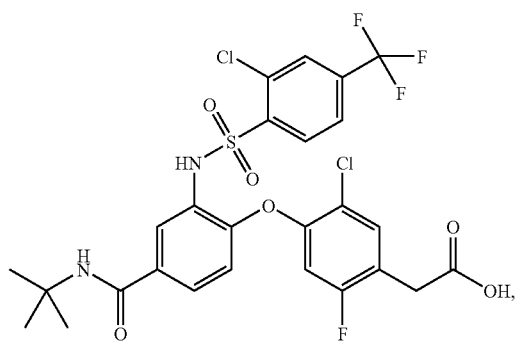

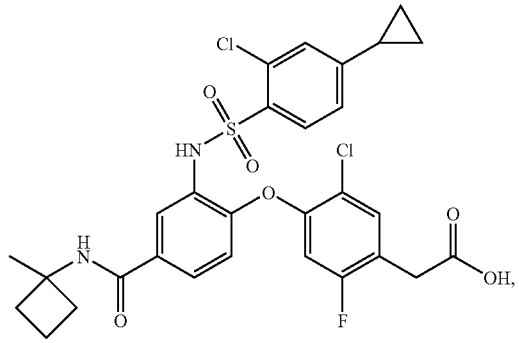

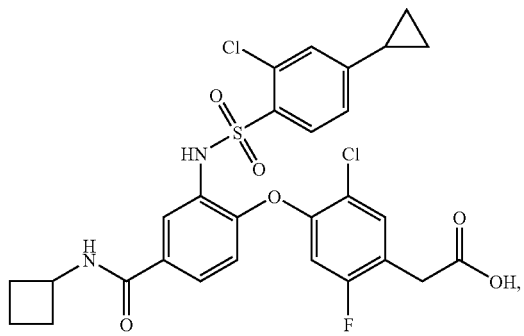

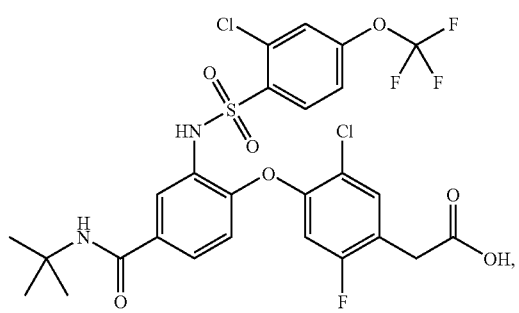

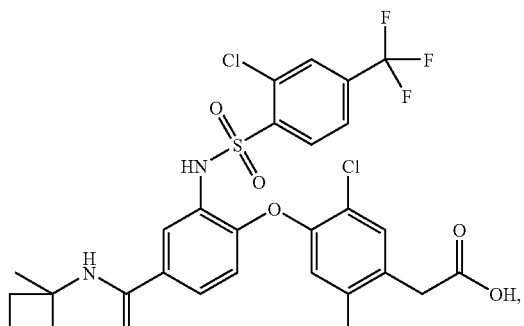

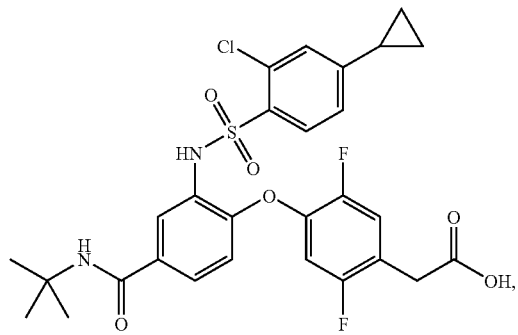

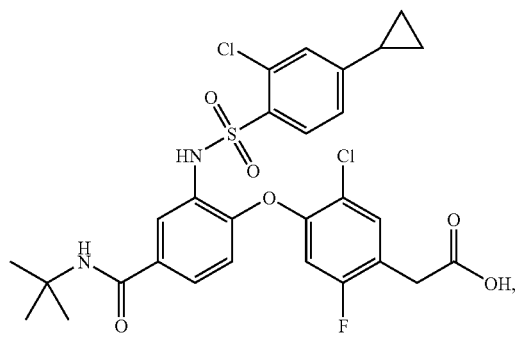

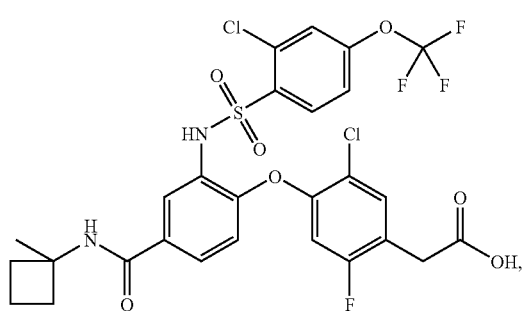

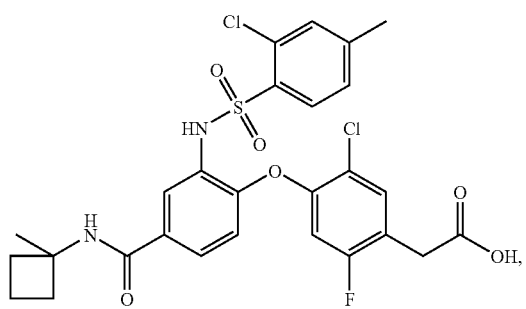

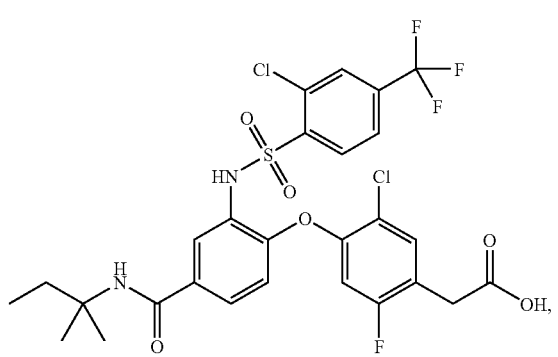

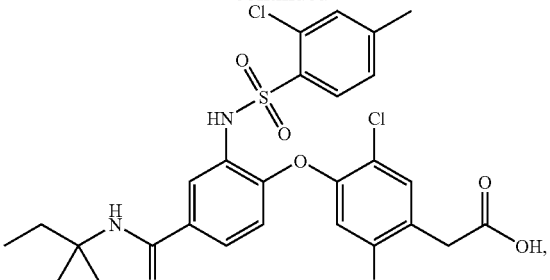

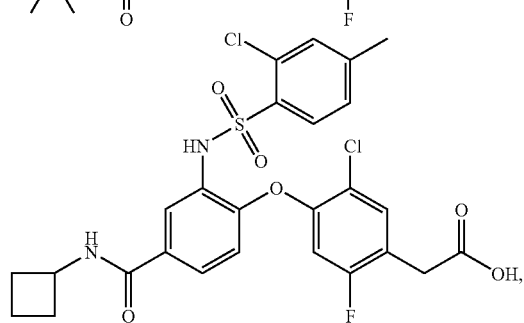

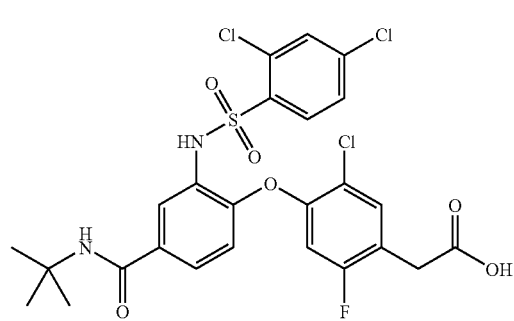

and salts thereof.

Preparation of the Compounds

Synthetic routes to the compounds provided herein are described in the Examples. One of skill in the art will understand that the synthetic routes can be modified to use different starting materials and/or alternate reagents to accomplish the desired transformations. Additionally, one of skill in the art will recognize that protecting groups may be necessary for the preparation of certain compounds and will be aware of those conditions compatible with a selected protecting group. Accordingly, the methods and reagents described herein are all expressed as non-limiting embodiments.

The present invention includes A process for manufacturing a compound of Formula II

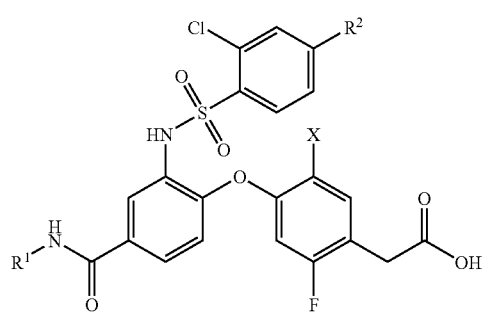

II wherein

R¹ is t-butyl;

R² is alkyl, haloalkyl, alkoxy, haloalkoxy or cycloalkyl (where preferred R² groups are the same as those listed for R² groups in Formula I); and X is chloro or fluoro;

comprising the step of contacting a compound of Formula A

A where R³ is chloro, bromo, iodo, —OS(O)₂alkyl or —OS(O)₂aryl;

with a compound of formula B

B in the presence of
a) a transition metal catalyst; and
b) a base; and to form a compound of Formula C

C

The present invention further includes a process wherein the compound of Formula C is further contacted with a compound of Formula D R¹—O—C(=O)-alkyl          D in the presence of an acid to form a compound of Formula E

E wherein the compound of Formula E is subsequently hydrolyzed to form a compound of Formula II.

The present invention further includes a process wherein the compound of Formula A is prepared by contacting a compound of Formula F

F with a compound of Formula G

G where R⁴ is halogen or OTs;

in the presence of a base.

The present invention further includes a process wherein the compound of Formula B is prepared by a process comprising the step of contacting a compound of Formula H

H with a compound selected from R²—BY, and R²-M-X¹
where Y is —(OR)₂, —F₃—, or R'₂;
R is independently H, alkyl, aryl or arylalkyl;
   or the two R groups may combine to form pinacol or catechol;
R' is alkyl, or the two R¹ groups may combine to form 9-Borabicyclononane (9-BBN);
M is Zn or Mg; and
X¹ is Cl, Br or I;

in the presence of a
a) a transition metal catalyst; and
b) a base;
to form a compound of Formula J

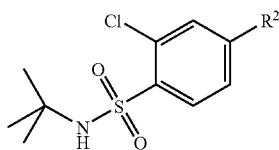

Suitable examples of $R^2$—BY and $R^2$-M-$X^1$ include $R^2ZnC^1$, $R^2ZnBr$, $R^2ZnI$, $R^2MgCl$, $R^2MgBr$, $R^2MgI$, $R^2B(OH)_2$, $R^2B$ (pinacol), $R^2B$(catechol), $R^2B(OiPr)_2$, $R^2BF_3K$, and $R^2$-9-BBN).

The present invention further includes a process wherein the compound of Formula F is prepared by a process comprising contacting a compound of Formula K

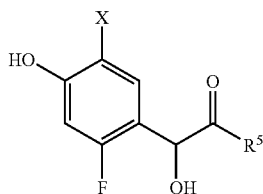

where $R^5$ is CN, —C(=O)OH or —C(=O)O-alkyl
with either
(1) aqueous hydrogen iodide or a metal iodide salt in the presence of a strong acid; or
(2) a reductant in the presence of an acid.

Preferred reaction conditions include the use of elevated temperatures and inert atmosphere.

Intermediates

The present invention further includes novel intermediates of Formula C useful for making a compound of Formula II

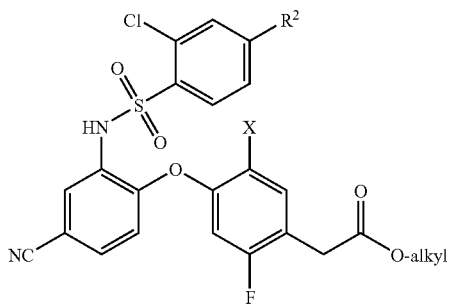

Compositions

In another aspect, the invention provides pharmaceutical compositions suitable for pharmaceutical use comprising one or more compounds of the invention and a pharmaceutically acceptable carrier, excipient or diluent.

The term "composition" as used herein is intended to encompass a product comprising the specified ingredients (and in the specified amounts, if indicated), as well as any product which results, directly or indirectly, from combination of the specified ingredients in the specified amounts. By "pharmaceutically acceptable" it is meant that the carrier or excipient is compatible with the other ingredients of the formulation and not deleterious to the recipient thereof.

Formulation may improve one or more pharmacokinetic properties (e.g., oral bioavailabilty, membrane permeability) of a compound of the invention (herein referred to as the active ingredient).

The pharmaceutical compositions for the administration of the compounds of this invention may conveniently be presented in unit dosage form and may be prepared by any of the methods well known in the art. All methods include the step of bringing the active ingredient into association with the carrier which constitutes one or more accessory ingredients. In general, the pharmaceutical compositions are prepared by uniformly and intimately bringing the active ingredient into association with a liquid carrier or a finely divided solid carrier or both, and then, if necessary, shaping the product into the desired formulation. In the pharmaceutical composition the active object compound is included in an amount sufficient to produce the desired effect upon the process or condition of diseases.

The pharmaceutical compositions containing the active ingredient may be in a form suitable for oral use, for example, as tablets, troches, lozenges, aqueous or oily suspensions, dispersible powders or granules, emulsions, hard or soft capsules, or syrups or elixirs. Compositions intended for oral use may be prepared according to any method known to the art for the manufacture of pharmaceutical compositions. Such compositions may contain one or more agents selected from sweetening agents, flavoring agents, coloring agents and preserving agents in order to provide pharmaceutically elegant and palatable preparations. Tablets contain the active ingredient in admixture with other non-toxic pharmaceutically acceptable excipients which are suitable for the manufacture of tablets. These excipients may be, for example, inert diluents, such as calcium carbonate, sodium carbonate, lactose, calcium phosphate or sodium phosphate; granulating and disintegrating agents, for example, corn starch, or alginic acid; binding agents, for example starch, gelatin or acacia, and lubricating agents, for example magnesium stearate, stearic acid or talc. The tablets may be uncoated or they may be coated by known techniques to delay disintegration and absorption in the gastrointestinal tract and thereby provide a sustained action over a longer period. For example, a time delay material such as glyceryl monostearate or glyceryl distearate may be employed. They may also be coated by the techniques described in U.S. Pat. Nos. 4,256,108; 4,166,452 and 4,265,874 to form osmotic therapeutic tablets for control release.

Formulations for oral use may also be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example peanut oil, liquid paraffin, or olive oil.

Aqueous suspensions contain the active materials in admixture with excipients suitable for the manufacture of aqueous suspensions. Such excipients are suspending agents, for example sodium carboxymethylcellulose, methylcellulose, hydroxy-propylmethylcellulose, sodium alginate, polyvinyl-pyrrolidone, gum tragacanth and gum acacia; dispersing or wetting agents may be a naturally-occurring phosphatide, for example lecithin, or condensation products of an alkylene oxide with fatty acids, for example polyoxyethylene stearate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives, for example ethyl, or n-propyl, p-hydroxybenzoate, one or more coloring agents, one or more flavoring agents, and one or more sweetening agents, such as sucrose or saccharin.

Oily suspensions may be formulated by suspending the active ingredient in a vegetable oil, for example arachis oil, olive oil, sesame oil or coconut oil, or in a mineral oil such as liquid paraffin. The oily suspensions may contain a thickening agent, for example beeswax, hard paraffin or cetyl alcohol. Sweetening agents such as those set forth above, and flavoring agents may be added to provide a palatable oral preparation. These compositions may be preserved by the addition of an anti-oxidant such as ascorbic acid.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, for example sweetening, flavoring and coloring agents, may also be present.

The pharmaceutical compositions of the invention may also be in the form of oil-in-water emulsions. The oily phase may be a vegetable oil, for example olive oil or arachis oil, or a mineral oil, for example liquid paraffin or mixtures of these. Suitable emulsifying agents may be naturally-occurring gums, for example gum acacia or gum tragacanth, naturally-occurring phosphatides, for example soy bean, lecithin, and esters or partial esters derived from fatty acids and hexitol anhydrides, for example sorbitan monooleate, and condensation products of the said partial esters with ethylene oxide, for example polyoxyethylene sorbitan monooleate. The emulsions may also contain sweetening and flavoring agents.

Syrups and elixirs may be formulated with sweetening agents, for example glycerol, propylene glycol, sorbitol or sucrose. Such formulations may also contain a demulcent, a preservative and flavoring and coloring agents.

The pharmaceutical compositions may be in the form of a sterile injectable aqueous or oleagenous suspension. This suspension may be formulated according to the known art using those suitable dispersing or wetting agents and suspending agents which have been mentioned above. The sterile injectable preparation may also be a sterile injectable solution or suspension in a non-toxic parenterally-acceptable diluent or solvent, for example as a solution in 1,3-butane diol. Among the acceptable vehicles and solvents that may be employed are water, Ringer's solution and isotonic sodium chloride solution. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

The pharmaceutical compositions may also be administered in the form of suppositories for rectal administration of the drug. These compositions can be prepared by mixing the drug with a suitable non-irritating excipient which is solid at ordinary temperatures but liquid at the rectal temperature and will therefore melt in the rectum to release the drug. Such materials are cocoa butter and polyethylene glycols.

For topical use, creams, ointments, jellies, solutions or suspensions, etc., containing the compounds of the invention are employed. As used herein, topical application is also meant to include the use of mouthwashes and gargles.

The pharmaceutical compositions and methods of the invention may further comprise other therapeutically active compounds, as noted herein, useful in the treatment of asthma, allergic diseases, inflammatory conditions and cancer and pathologies associated therewith (e.g., cardiovascular disease) or other adjuvant. In many instances, compositions which include a compounds of the invention and an alternative agent have additive or synergistic effects when administered.

Methods of Use

In yet another aspect, the invention provides methods of treating or preventing a disease or condition associated with CRTH2 and/or one or more other $PGD_2$ receptors by administering to a subject having such a condition or disease, a therapeutically effective amount of a compound or composition of the invention. In one group of embodiments, diseases and conditions, including chronic diseases of humans or other species, can be treated with modulators, or antagonists, of CRTH2 and/or one or more other $PGD_2$ receptors. These diseases and conditions include (1) inflammatory or allergic diseases such as systemic anaphylaxis and hypersensitivity disorders, COPD, atopic dermatitis, urticaria, drug allergies, insect sting allergies, food allergies (including celiac disease and the like) and mastocytosis, (2) inflammatory bowel diseases such as Crohn's disease, ulcerative colitis, ileitis and enteritis, (3) vasculitis, Behcet's syndrome, (4) psoriasis and inflammatory dermatoses such as dermatitis, eczema, atopic dermatitis, allergic contact dermatitis, urticaria, viral cutaneous pathologies such as those derived from human papillomavirus, HIV or RLV infection, bacterial, fungal and other parasital cutaneous pathologies, and cutaneous lupus erythematosus, (5) asthma and respiratory allergic diseases such as allergic asthma, allergic rhinitis, otitis media, allergic conjunctivitis, hypersensitivity lung diseases, chronic obstructive pulmonary disease and the like, (6) autoimmune diseases, such as arthritis (including rheumatoid and psoriatic), systemic lupus erythematosus, type I diabetes, myasthenia gravis, multiple sclerosis, Graves' disease, glomerulonephritis and the like, (7) graft rejection (including allograft rejection and graft-v-host disease), e.g., skin graft rejection, solid organ transplant rejection, bone marrow transplant rejection, (8) fever, (9) cardiovascular disorders such as acute heart failure, hypotension, hypertension, angina pectoris, myocardial infarction, cardiomyopathy, congestive heart failure, atherosclerosis, coronary artery disease, restenosis and vascular stenosis, (10) cerebrovascular disorders such as traumatic brain injury, stroke, ischemic reperfusion injury and aneurysm, (11) cancers of the breast, skin, prostate, cervix, uterus, ovary, testes, bladder, lung, liver, larynx, oral cavity, colon and gastrointestinal tract (e.g., esophagus, stomach, pancreas), brain, thyroid, blood and lymphatic system, (12) fibrosis, connective tissue disease and sarcoidosis, (13) genital and reproductive conditions such as erectile dysfunction, (14) gastrointestinal disorders such as gastritis, ulcers, nausea, pancreatitis and vomiting; (15) neurologic disorders, such as Alzheimer's disease, (16) sleep disorders such as insomnia, narcolepsy, sleep apnea syndrome and Pickwick Syndrome, (17) pain, (18) renal disorders, (19) ocular disorders such as glaucoma, and (20) infectious diseases such as HIV.

In yet another aspect, the invention provides methods of treating or preventing a disease or disorder responsive to modulation of CRTH2 and/or one or more other $PGD_2$ receptors comprising administering to a subject having such a disease or disorder, a therapeutically effective amount of one or more of the subject compounds or compositions.

In yet another aspect, the invention provides methods of treating or preventing a disease or disorder mediated by CRTH2 and/or one or more other $PGD_2$ receptors comprising administering to a subject having such a condition or disease, a therapeutically effective amount of one or more of the subject compounds or compositions.

In yet another aspect, the invention provides methods of modulating CRTH2 and/or one or more other $PGD_2$ receptors comprising contacting a cell with one or more of the subject compounds or compositions.

Depending on the disease to be treated and the subject's condition, the compounds of the invention may be administered by oral, parenteral (e.g., intramuscular, intraperitoneal, intravenous, ICV, intracisternal injection or infusion, subcutaneous injection or implant), inhalation, nasal, vaginal, rectal, sublingual, or topical (e.g., transdermal, local) routes of administration and may be formulated, alone or together, in suitable dosage unit formulations containing conventional non-toxic pharmaceutically acceptable carriers, adjuvants and vehicles appropriate for each route of administration. The invention also contemplates administration of the compounds of the invention in a depot formulation, in which the active ingredient is released over a defined time period.

In the treatment or prevention of asthma, COPD, allergic rhinitis, eczema, psoriasis, atopic dermatitis, fever, sepsis, systemic lupus erythematosus, diabetes, rheumatoid arthritis, multiple sclerosis, atherosclerosis, transplant rejection, inflammatory bowel disease, cancer or other conditions or disorders associated with CRTH2 and/or one or more other $PGD_2$ receptors, an appropriate dosage level will generally be about 0.001 to 100 mg per kg patient body weight per day which can be administered in single or multiple doses. Preferably, the dosage level will be about 0.01 to about 25 mg/kg per day; more preferably about 0.05 to about 10 mg/kg per day. A suitable dosage level may be about 0.01 to 25 mg/kg per day, about 0.05 to 10 mg/kg per day, or about 0.1 to 5 mg/kg per day. Within this range the dosage may be 0.005 to 0.05, 0.05 to 0.5 or 0.5 to 5.0 mg/kg per day. For oral administration, the compositions are preferably provided in the form of tablets containing 1.0 to 1000 milligrams of the active ingredient, particularly 1.0, 5.0, 10.0, 15.0, 20.0, 25.0, 50.0, 75.0, 100.0, 150.0, 200.0, 250.0, 300.0, 400.0, 500.0, 600.0, 750.0, 800.0, 900.0, and 1000.0 milligrams of the active ingredient for the symptomatic adjustment of the dosage to the patient to be treated. The compounds may be administered on a regimen of 1 to 4 times per day, preferably once or twice per day.

It will be understood, however, that the specific dose level and frequency of dosage for any particular patient may be varied and will depend upon a variety of factors including the activity of the specific compound employed, the metabolic stability and length of action of that compound, the age, body weight, general health, sex, diet, mode and time of administration, rate of excretion, drug combination, the severity of the particular condition, and the host undergoing therapy.

The compounds of the invention can be combined or used in combination with other agents useful in the treatment, prevention, suppression or amelioration of the diseases or conditions for which compounds of the invention are useful, including asthma, allergic rhinitis, eczema, psoriasis, atopic dermatitis, fever, sepsis, systemic lupus erythematosus, diabetes, rheumatoid arthritis, multiple sclerosis, atherosclerosis, transplant rejection, inflammatory bowel disease, cancer and those pathologies noted above.

Such other agents, or drugs, may be administered, by a route and in an amount commonly used therefor, simultaneously or sequentially with a compound of the invention. When a compound of the invention is used contemporaneously with one or more other drugs, a pharmaceutical composition containing such other drugs in addition to the compound of the invention is preferred. Accordingly, the pharmaceutical compositions of the invention include those that also contain one or more other active ingredients or therapeutic agents, in addition to a compound of the invention.

Examples of other therapeutic agents that may be combined with a compound of the invention, either administered separately or in the same pharmaceutical compositions, include, but are not limited to: (a) VLA-4 antagonists, (b) corticosteroids, such as beclomethasone, methylprednisolone, betamethasone, prednisone, prenisolone, dexamethasone, fluticasone and hydrocortisone, and corticosteroid analogs such as budesonide; (c) immunosuppressants such as cyclosporine (cyclosporine A, Sandimmune®, Neoral®), tacrolimus (FK-506, Prograf®), rapamycin (sirolimus, Rapamune®) and other FK-506 type immunosuppressants, and mycophenolate, e.g., mycophenolate mofetil (CellCept®); (d) antihistamines (H1-histamine antagonists) such as bromopheniramine, chlorpheniramine, dexchlorpheniramine, triprolidine, clemastine, diphenhydramine, diphenylpyraline, tripelennamine, hydroxyzine, methdilazine, promethazine, trimeprazine, azatadine, cyproheptadine, antazoline, pheniramine pyrilamine, astemizole, terfenadine, loratadine, cetirizine, fexofenadine, descarboethoxyloratadine, and the like; (e) non-steroidal anti-asthmatics such as $\square_2$-agonists (e.g., terbutaline, metaproterenol, fenoterol, isoetharine, albuterol, bitolterol and pirbuterol) and $\square$2-agonist-corticosteroid combinations (e.g., salmeterol-fluticasone (Advair®), formoterol-budesonid (Symbicort®)), theophylline, cromolyn sodium, atropine, ipratropium bromide, leukotriene antagonists (e.g., zafirlukast, montelukast, pranlukast, iralukast, pobilukast and SKB-106,203), leukotriene biosynthesis inhibitors (zileuton, BAY-1005); (f) non-steroidal anti-inflammatory agents (NSAIDs) such as propionic acid derivatives (e.g., alminoprofen, benoxaprofen, bucloxic acid, carprofen, fenbufen, fenoprofen, fluprofen, flurbiprofen, ibuprofen, indoprofen, ketoprofen, miroprofen, naproxen, oxaprozin, pirprofen, pranoprofen, suprofen, tiaprofenic acid and tioxaprofen), acetic acid derivatives (e.g., indomethacin, acemetacin, alclofenac, clidanac, diclofenac, fenclofenac, fenclozic acid, fentiazac, furofenac, ibufenac, isoxepac, oxpinac, sulindac, tiopinac, tolmetin, zidometacin and zomepirac), fenamic acid derivatives (e.g., flufenamic acid, meclofenamic acid, mefenamic acid, niflumic acid and tolfenamic acid), biphenylcarboxylic acid derivatives (e.g., diflunisal and flufenisal), oxicams (e.g., isoxicam, piroxicam, sudoxicam and tenoxican), salicylates (e.g., acetyl salicylic acid and sulfasalazine) and the pyrazolones (e.g., apazone, bezpiperylon, feprazone, mofebutazone, oxyphenbutazone and phenylbutazone); (g) cyclooxygenase-2 (COX-2) inhibitors such as celecoxib (Celebrex®) and rofecoxib (Vioxx®); (h) inhibitors of phosphodiesterase type IV (PDE-IV); (i) other $PGD_2$ receptor antagonists, especially DP antagonists; (j) opioid analgesics such as codeine, fentanyl, hydromorphone, levorphanol, meperidine, methadone, morphine, oxycodone, oxymorphone, propoxyphene, buprenorphine, butorphanol, dezocine, nalbuphine and pentazocine; (k) cholesterol lowering agents such as HMG-CoA reductase inhibitors (e.g., lovastatin, simvastatin, pravastatin, fluvastatin, atorvastatin and other statins), bile acid sequestrants (e.g., cholestyramine and colestipol), vitamin $B_3$ (also known as nicotinic acid, or nia cin), vitamin B$_6$ (pyridoxine), vitamin B$_{12}$ (cyanocobalamin), fibric acid derivatives (e.g., gemfibrozil, clofibrate, fenofibrate and benzafibrate), probucol, nitroglycerin, and inhibitors of cholesterol absorption (e.g., beta-sitosterol and acyl-CoA-cholesterol acyltransferase (ACAT) inhibitors such as melinamide), HMG-CoA synthase inhibitors, squalene epoxidase inhibitors and squalene synthetase inhibitors; (l) antithrombotic agents, such as thrombolytic agents (e.g., streptokinase, alteplase, anistreplase and reteplase), heparin, hirudin and warfarin derivatives, □-blockers (e.g., atenolol), □-adrenergic agonists (e.g., isoproterenol), ACE inhibitors and vasodilators (e.g., sodium nitroprusside, nicardipine hydrochloride, nitroglycerin and enaloprilat); (m) anti-diabetic agents such as insulin and insulin mimetics, sulfonylureas (e.g., glyburide, meglinatide), biguanides, e.g., metformin (Glucophage®), □-glucosidase inhibitors (acarbose), thiazolidinone compounds, e.g., rosiglitazone (Avandia®), troglitazone (Rezulin®), ciglitazone, pioglitazone (Actos®) and englitazone; (n) preparations of interferon beta (interferon □-1□, interferon □-1□); (o) gold compounds such as auranofin and aurothioglucose, (p) TNF inhibitors, e.g., etanercept (Enbrel®), antibody therapies such as orthoclone (OKT3), daclizumab (Zenapax®), basiliximab (Simulect®), infliximab (Remicade®) and D2E6 TNF antibody, (q) lubricants or emollients such as petrolatum and lanolin, keratolytic agents, vitamin D$_3$ derivatives (e.g., calcipotriene and calcipotriol (Dovonex®)), PUVA, anthralin (Drithrocreme®), etretinate (Tegison®) and isotretinoin; (r) multiple sclerosis therapeutic agents such as interferon □-1□ (Betaseron®), interferon □-1□ (Avonex®), azathioprine (Imurek®, Imuran®), glatiramer acetate (Capoxone®), a glucocorticoid (e.g., prednisolone) and cyclophosphamide; (s) other compounds such as 5-aminosalicylic acid and prodrugs thereof; (t) DNA-alkylating agents (e.g., cyclophosphamide, ifosfamide), antimetabolites (e.g., azathioprine, 6-mercaptopurine, methotrexate, a folate antagonist, and 5-fluorouracil, a pyrimidine antagonist), microtubule disruptors (e.g., vincristine, vinblastine, paclitaxel, colchicine, nocodazole and vinorelbine), DNA intercalators (e.g., doxorubicin, daunomycin and cisplatin), DNA synthesis inhibitors such as hydroxyurea, DNA cross-linking agents, e.g., mitomycin C, hormone therapy (e.g., tamoxifen, and flutamide), and cytostatic agents, e.g., imatinib (ST1571, Gleevec®) and rituximab (Rituxan®). The weight ratio of the compound of the invention to the second active ingredient may be varied and will depend upon the effective dose of each ingredient. Generally, an effective dose of each will be used. Thus, for example, when a compound of the invention is combined with an NSAID, the weight ratio of the compound of the invention to the NSAID will generally range from about 1000:1 to about 1:1000, preferably about 200:1 to about 1:200. Combinations of a compound of the invention and other active ingredients will generally also be within the aforementioned range, but in each case, an effective dose of each active ingredient should be used.

EXAMPLES

The following examples are provided by way of illustration only and not by way of limitation. Those of skill in the art will readily recognize a variety of noncritical parameters that could be changed or modified to yield essentially similar results.

Example 1

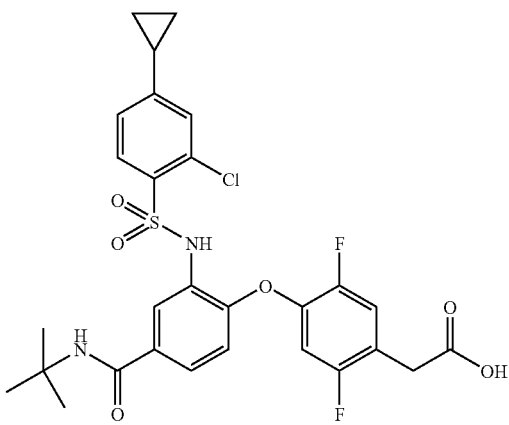

2-(4-(4-(tert-butylcarbamoyl)-2-(2-chloro-4-cyclopropylphenylsulfonamido)phenoxy)-2,5-difluorophenyl)acetic acid (A)

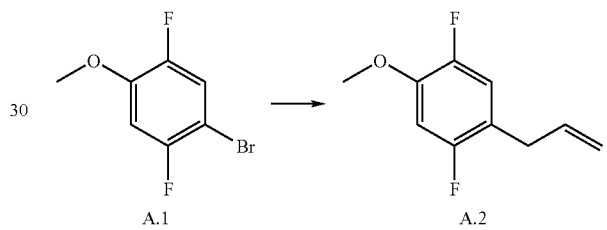

1-Allyl-2,5-difluoro-4-methoxybenzene (A.2). Under Argon atmosphere, the mixture of compound A.1 (5 g, 22.4 mmol) and allyltributyltin (8.91 g, 27 mmol) in the presence of Pd(PPh$_3$)$_4$ (2.59 g, 2.24 mmol) in anhydrous DMF (100 ml) was stirred at 110° C. for 4 hours. The solution was diluted with ethyl acetate and then filtered. The filtrate was washed with water and brine, dried over Na$_2$SO$_4$ and concentrated in vacuo. The residue was purified by flash chromatography (silica gel, 100% hexane eluent) to give compound A.2 (4.0 g, 97%). $^1$H NMR (400 MHz) (CDCl$_3$) δ 7.30 (d, J=13.7 Hz, 1H); 7.19 (d, J=7.8 Hz, 1H); 5.87-5.97 (m, 1H); 5.07-5.12 (m, 2H); 3.91 (s, 3H); 3.33 (d, J=6.45 Hz, 2H)

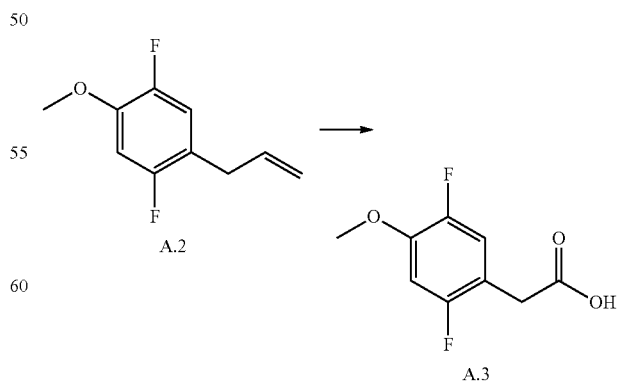

2-(2,5-Difluoro-4-methoxyphenyl)acetic acid (A.3). To a solution of compound A.2 (4.0 g, 22 mmol) in a mixed solvent (CCl₄:CH₃CN:H₂O=1:1:1.5, 350 ml), NaIO₄ (23.25 g, 22 mmol) and RuCl₃.H₂O (0.68 g, 3.3 mmol) were added in one portion. The reaction mixture was stirred at room temperature for 1 hour and then poured into water. The aqueous layer was extracted with DCM (3×), the combined organic layers were washed with water and brine, dried over Na₂SO₄ and concentrated in vacuo to give compound A.3 (2.7 g, 56%). LC-MS ESI (neg.) m/z: 201.1 (M–H).

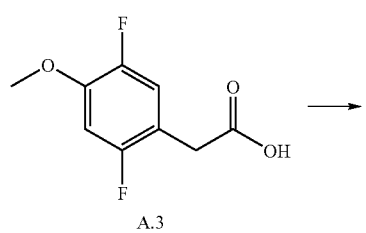

2-(2,5-Difluoro-4-hydroxyphenyl)acetic acid (A.4). Under N₂, to a solution of compound A.3 (2.7 g, 13.4 mmol) in DCM (60 ml) at −78° C., was added a solution of BBr₃ in dichloromethane (1M, 38 mmol) dropwise over 1 hour. The reaction mixture was stirred at room temperature for 5 hours and then poured into ice water. The aqueous layer was extracted with ethyl acetate (3×), the combined organic layers were washed with water and brine, dried over Na₂SO₄ and concentrated in vacuo to give compound A.4 (2.5 g, 97%). LC-MS ESI (pos.) m/z: 188.9 (M+H). $^1$H NMR (500 MHz) (DMSO-d₆) δ 7.14 (dd, J=11.0, 7.2 Hz, 1H); 6.74 (dd, J=11.0, 7.2 Hz, 1H); 3.49 (s, 2H).

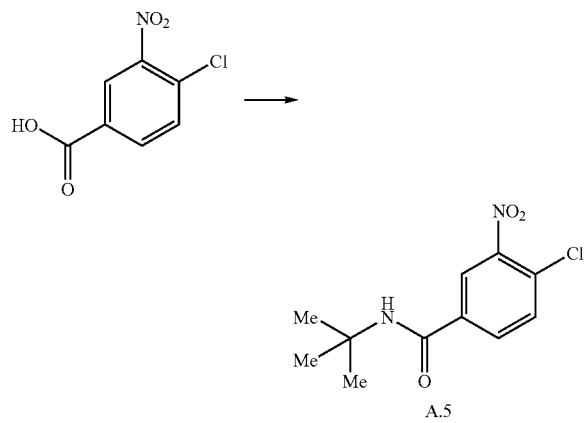

N-tert-butyl-4-chloro-3-nitrobenzamide (A.5). To a solution of 4-chloro-3-nitrobenzoic acid (56.17 g, 255 mmol) dissolved in 325 mL THF cooled by an ice-bath was added dropwise over 30 minutes a solution of tert-butylamine (26.9 mL, 255 mmol) and 39.1 mL triethylamine in 75 mL THF. The reaction was equilibrated to room temperature. After 5 hours, the solids were removed by filtration and the filtrate concentrated in vacuo. The resulting solid was partitioned between 250 mL each ethyl acetate and 0.5N aqueous hydrochloric acid. The organic layer was washed with 4×150 mL saturated bicarb solution followed by 100 mL each water and brine. The organic layer was stirred over magnesium sulfate, filtered and the filtrate concentrated in vacuo to afford an off-white solid. $^1$H NMR (500 MHz) (CDCl₃) δ 8.07 (d, J=8.8 Hz, 1H); 7.93 (d, J=2.2 Hz, 1H); 7.73 (s, 1H); 7.49 (dd, J₁=1.9 Hz, J₂=8.6 Hz, 1H); 7.38 (d, J=7.3 Hz, 1H); 7.22 (s, 1H); 7.17 (d, J=8.6 Hz, 1H); 6.62 (d, J=8.6 Hz, 1H); 6.38 (d, J=9.5 Hz, 1H); 5.94 (s, 1H); 3.67 (s, 2H); 1.47 (s, 9H) ppm.

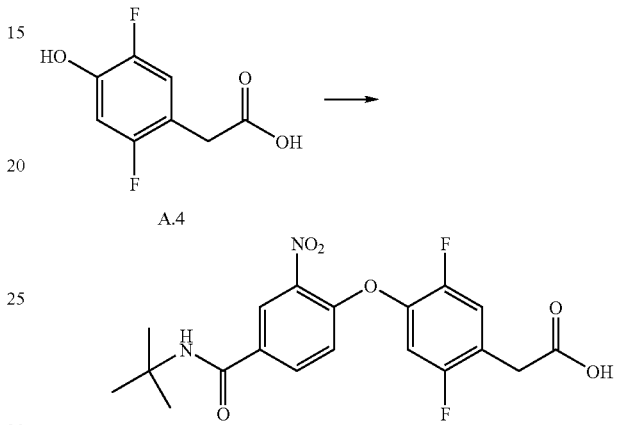

Methyl 2-(4-(4-(tert-butylcarbamoyl)-2-nitrophenoxy)-2,5-difluorophenyl)acetate (A.6) To a solution of compound A.4 (500 mg, 2.66 mmol) and N-tert-butyl-4-chloro-3-nitrobenzamide (A.5) (682 mg, 2.66 mmol) in DMSO (25 ml), Cs₂CO₃ (1.73 g, 5.32 mmol) was added in one portion. The reaction mixture was stirred at 80° C. for 1 hour, diluted with ethyl acetate and then 10% citric acid was added to adjust pH=2. The aqueous layer was extracted with ethyl acetate (2×), the combined organic layers were washed with water and brine, dried over Na₂SO₄ and concentrated in vacuo. The residue was dissolved in methanol (10 ml) then chlorotrimethylsilane was added to the solution. The reaction was stirred at room temperature for 1 hour and concentrated in vacuo. The residue was purified by flash column chromatography (silica gel, 30% ethyl acetate in hexane.eluent) to give compound A.6 (340 mg, 30%, 2 steps). LC-MS ESI (pos.) m/z: 423.1 (M+H).

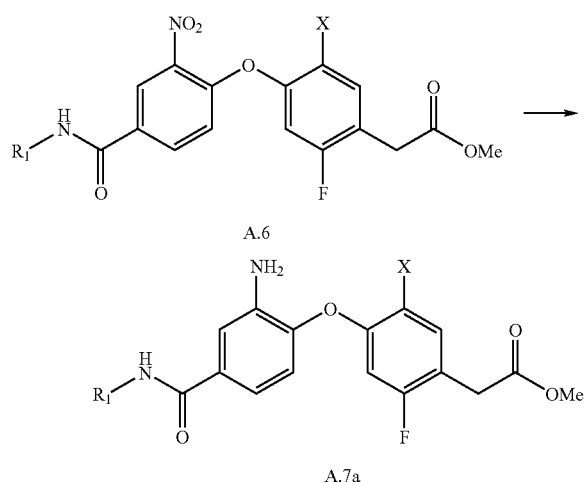

A.6

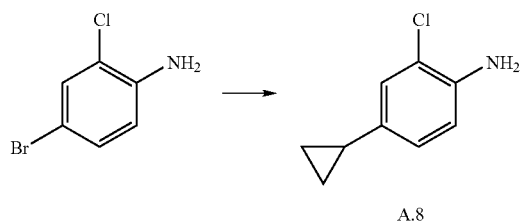

A.7a

Condition 1. (X=F)

Compound A.6 (0.81 mmol) was dissolved in a mixture of ethyl acetate (5 ml) and methanol (5 ml). 10% Pd/C (86 mg, 0.081 mmol) was added and the reaction mixture was stirred under H₂ at room temperature for 1 hour. The reaction mixture was filtered and the filtrate was concentrated in vacuo to give compound A.7a.

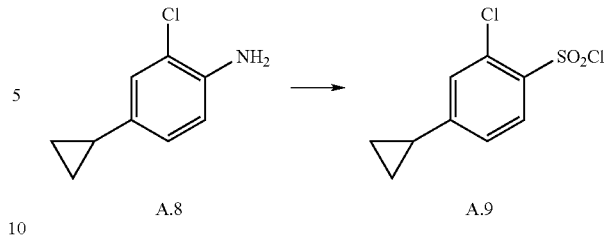

2-chloro-4-cyclopropylbenzenamine (A.8). To a 5 L jacketed reactor equipped with a mechanical stirrer and a reflux condenser under nitrogen was added 4-bromo-2-chloroaniline (103 g, 499 mmol), cyclopropylboronic acid (58 g, 673 mmol), and potassium phosphate (376 g, 1771 mmol) in 2.5 L toluene. The reaction flask was evacuated and back filled with nitrogen before adding tricyclohexylphosphine (14 g, 51 mmol) followed by water (100 mL). The reaction was again evacuated and back-filled with nitrogen 3 times before adding palladium(II) acetate (5.8 g, 26 mmol). The flask was evacuated and back-filled with nitrogen one more time and heated to 94° C. using a heating mantle. Upon heating, the gummy precipitate turned into a dark brown solution. After 2.5 hours, the reaction was checked by HPLC to find that no starting materials remained. The reaction was cooled to room temperature and then transferred to a separation funnel to be extracted with water (2×500 mL) and then brine (500 mL). The organics were stirred over MgSO₄ for 10 minutes and then filtered and the filtrate concentrated under in vacuo to afford an orange oil as the crude material (80 g). The crude material was then purified by flash chromatography (Silica; 1-10% EtOAc in Hexanes) as a gradient. The final purified material A.8 (67.7 g, 81% yield) was collected as an orange oil which crystallized overnight. LC-MS ESI (pos.) m/e: 168.1 (M+H).

2-chloro-4-cyclopropylbenzene-1-sulfonyl chloride (A.9). To a 5 L jacketed reaction vessel equipped with an overhead stirrer, nitrogen inlet, and a temperature probe was dissolved 2-chloro-4-cyclopropylbenzenamine (66.0 g, 394 mmol) in 1.6 L acetonitrile. To this stirring solution was added concentrated hydrochloric acid (632 ml). [Note: the jacketed reactor was set to 15° C. for the HCl addition] Upon addition of HCl, the reaction exothermed slightly (from 18° C. to 22° C.). The reaction was then cooled to −2-0° C. before adding sodium nitrite (15 ml, 472 mmol) as a solution in water (80.0 ml) via dropping funnel over 20 minutes. This resulting orange mixture was then stirred under cooled conditions (0-5° C.) for an additional hour before adding 750 mL chilled acetic acid. Then sulfur dioxide (141 g) was bubbled into the reaction mixture by lecture bottle through a gas dispersion tube over a period of 20 minutes. Then, a mixture of copper (II) chloride (27 g, 201 mmol) and copper(I) chloride (0.1 ml, 5 mmol) was added all at once to the reaction. The resulting green reaction mixture was equilibrated to room temperature and stirred overnight. The reaction mixture was filtered to remove solids. The filtrate was then concentrated in vacuo until a precipitate developed. The mixture was then diluted with ethyl acetate (1 L) and extracted with water (2×500 mL) and brine (1×500 mL). The organic layer was stirred over magnesium sulfate, filtered and the filtrate concentrated to a dark orange oily solid. The crude material was purified by column chromatography (Silica; 0-5% EtOAc in Hexanes). The final product A.9 (86 g, 87% yield) was obtained as a light yellow (oily textured) solid. ¹H NMR (500 MHz) (CDCl₃) □ 8.01 (d, J=8.4 Hz, 1H); 7.29 (d, J=1.7 Hz, 1H); 7.13 (dd, J=2.0, 8.6 Hz, 1H); 1.99 (m, 1H); 1.21 (m, 2H); 0.87 (m, 2H).

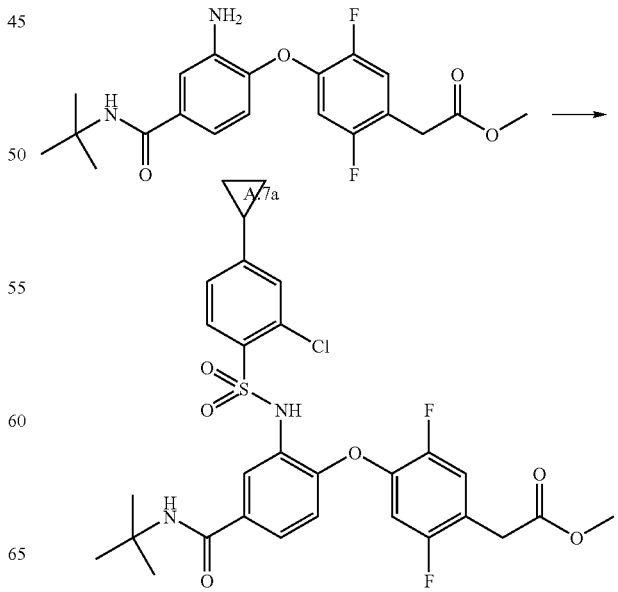

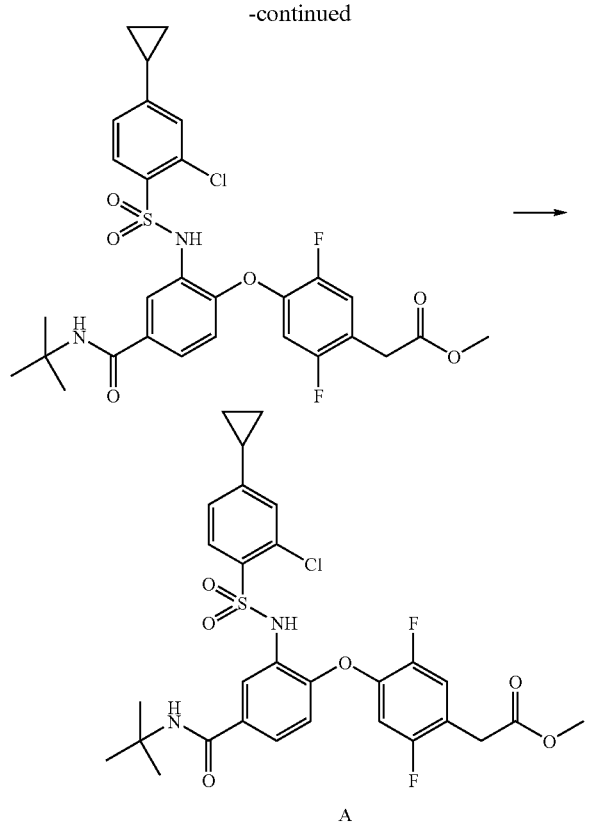

2-(4-(4-(tert-Butylcarbamoyl)-2-(2-chloro-4-cyclopropylphenylsulfonamido)phenoxy)-2,5-difluorophenyl)acetic acid (A) To a solution of compound A.7a (100 mg, 0.255 mmol) in pyridine (2 ml), sulfonyl chloride A.9 (76.8 mg, 0.306 mmol) was added. The reaction mixture was stirred at room temperature for 2 hours and then concentrated in vacuo. The concentrate was dissolved in the mixed solvent (THF: MeOH: $H_2O$=2:2:1, 2 ml) and lithium hydroxide (75.5 mg, 1.8 mmol) was added to the solution. The reaction mixture was stirred at room temperature for 2 hours and then concentrated in vacuo. The residue was purified by HPLC to give compound A (90 mg, 60% in two steps). MS ESI (pos.) m/e: 593.0 (M+H). $^1$H NMR (400 MHz) (DMSO-$d_6$) □ 7.96 (d, J=2.0 Hz, 1H); 7.75 (d, J=8.3 Hz, 1H); 7.50 (d, J=2.0 Hz, 1H), 7.48 (dd, J=8.0, 2.0 Hz, 1H); 7.08 (d, J=1.4 Hz, 1H); 6.98 (dd, J=8.3, 1.4 Hz, 1H); 6.71 (d, J=8.6 Hz, 1H); 6.32-6.35 (m, 1H); 3.33 (s, 2H); 1.89-1.90 (m, 1H); 1.46 (s, 9H); 1.06-1.10 (m, 2H); 0.72-0.75 (m, 2H).

The following example compounds 2 through 12 were prepared according to the methods described in Example 1. The step in Example 1 where compound A.6 is transformed to compound A.7a under "condition 1" was modified as set forth below:

Condition 2. (X=Cl)

Compound A.6 (1.02 mmol) was dissolved in a mixture of AcOH (20 ml) and $H_2O$ (8 ml). Fe power (3.07 mmol) was added to the solution. The reaction mixture was stirred at 60° C. for 3 hours and then concentrated in vacuo. The residue was diluted with ethyl acetate, saturated $Na_2CO_3$ was added to adjust PH=8. The aqueous layer was extracted with ethyl acetate (2×), the combined organic layers were washed with water and brine, dried over $Na_2SO_4$ and concentrated in vacuo to give compound A.7b.

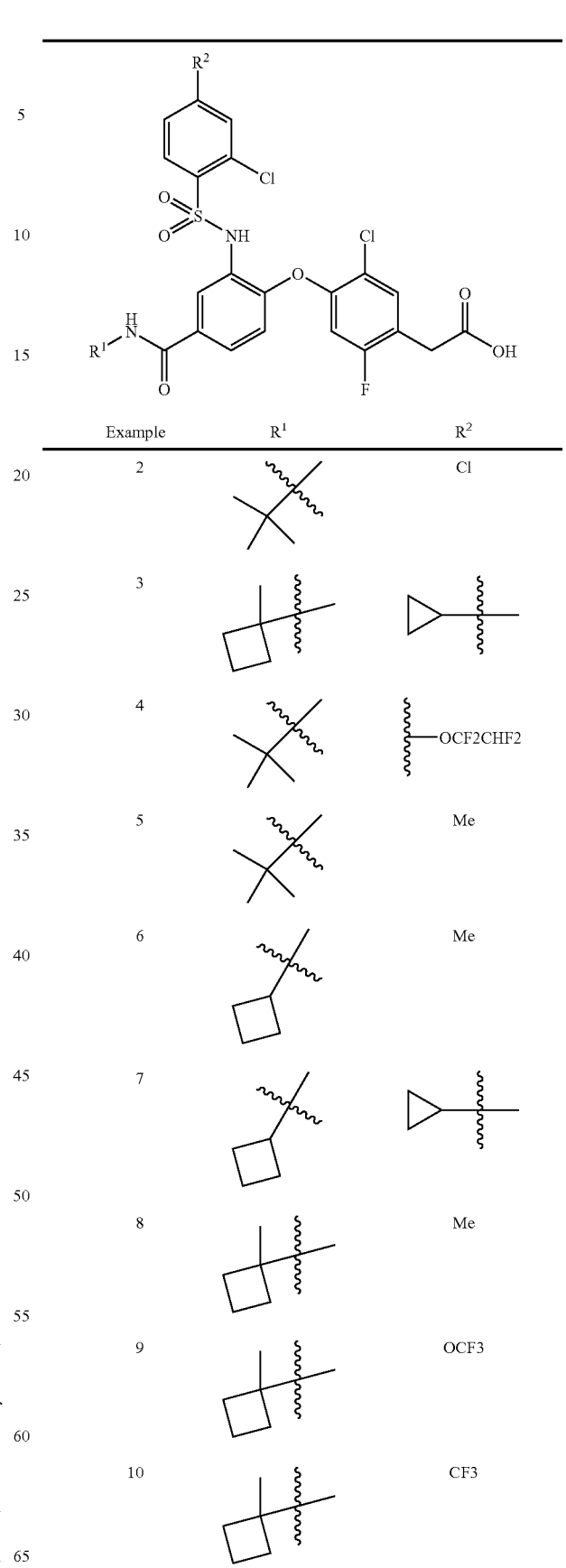

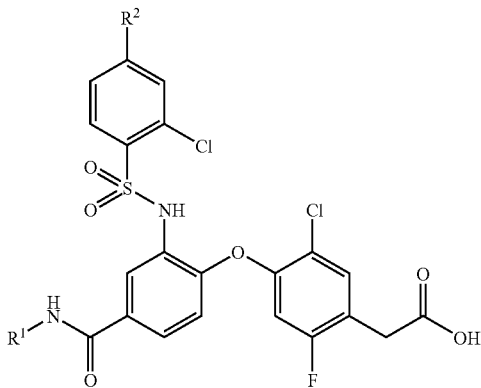

| Example | R¹ | R² |
|---------|-----|-----|
| 11 | (neopentyl-like group) | CF3 |
| 12 | (neopentyl-like group) | Me |

2-(4-(4-(tert-butylcarbamoyl)-2-(2,4-dichlorophenylsulfonamido)phenoxy)-5-chloro-2-fluorophenyl)acetic acid (B.1). MS ESI (pos.) m/e: 605.0 (M+H). $^1$H NMR (400 MHz) (CDCl$_3$) □ 7.98 (d, J=1.7 Hz, 1H); 7.90 (d, J=8.5 Hz, 1H); 7.47-7.55 (m, 3H); 7.37 (d, J=8.5 Hz 1H); 6.72 (d, J=8.5 Hz, 1H); 6.35 (d, J=10.0 Hz, 1H); 3.68 (s, 2H); 1.46 (s, 9H).

2-(5-chloro-4-(2-(2-chloro-4-cyclopropylphenylsulfonamido)-4-((1-methylcyclobutyl) carbamoyl)phenoxy)-2-fluorophenyl)acetic acid (B.2). MS ESI (pos.) m/e: 621.1 (M+H) $^1$H NMR (400 MHz) (MeOD) □ 8.04 (d, J=2.0 Hz, 1H); 7.77 (d, J=8.3 Hz, 1H); 7.53 (dd, J=8.6, 2.0 Hz, 1H); 7.47 (d, J=7.5 Hz, 1H); 7.09 (d, J=1.4 Hz, 1H); 6.98 (d, J=8.3, 1.4 Hz, 1H); 6.64 (d, J=8.6 Hz, 1H); 6.26 (d, J=10.0 Hz, 1H); 3.68 (s, 2H); 2.40 (dd, J=21.3, 9.5 Hz, 2H); 2.07-2.13 (m, 2H); 1.87-1.94 (m, 3H); 0.71-0.75 (m, 2H).

2-(4-(4-(tert-butylcarbamoyl)-2-(2-chloro-4-(1,1,2,2-tetrafluoroethoxy)phenylsulfonamido) phenoxy)-5-chloro-2-fluorophenyl)acetic acid (B.3). MS ESI (neg.) m/e: 683. (M−H). $^1$H NMR (400 MHz)(MeOD) 7.98-8.03 (m, 2H); 7.53 (dd, J=2.1, 4.0, 2H); 7.47 (d, J=7.5, 1H); 7.38 (d, J=2.1 Hz, 1H); 7.26 (d, J=8.8 Hz, 1H); 6.68 (d, J=8.8 Hz, 1H); 6.24-6.46 (m, 2H); 3.36 (s, 2H); 1.46 (s, 9H).

2-(4-(4-(tert-butylcarbamoyl)-2-(2-chloro-4-methylphenylsulfonamido)phenoxy)-5-chloro-2-fluorophenyl)acetic acid (B.4). MS ESI (neg.) m/e: 581.0 (M−H) $^1$H NMR (400 MHz) (MeOD) □ 7.99 (d, J=2.1 Hz, 1H); 7.81 (d, J=8.1 Hz, 1H); 7.65 (d, J=8.1 Hz, 1H); 7.47-7.51 (m, 2H); 7.23 (s, 1H); 7.16 (d, J=8.1, 1H); 6.68 (d, J=8.6 Hz, 1H); 6.19 (d, J=10.1 Hz, 1H); 3.67 (s, 2H); 2.33 (s, 3H); 1.46 (s, 9H).

2-(5-chloro-4-(2-(2-chloro-4-methylphenylsulfonamido)-4-(cyclobutylcarbamoyl)phenoxy)-2-fluorophenyl)acetic acid (B.5). MS ESI (pos.) m/e: 581.0 (M+H) $^1$H NMR (400 MHz) (MeOD) □ 8.08 (d, J=2.1 Hz, 1H); 7.80 (d, J=8.1 Hz, 1H); 7.57 (dd, J=8.6, 2.1 Hz, 1H); 7.48 (d, J=7.5 Hz, 1H); 7.23 (s, 1H); 7.15 (d, J=8.1 Hz, 1H); 6.68 (d, J=8.6 Hz, 1H); 6.21 (d, J=10.2 Hz, 1H); 4.44-4.53 (m, 1H); 3.67 (s, 2H); 2.32-2.40 (m, 5H); 2.07-2.17 (m, 2H); 1.75-1.83 (m, 2H).

2-(5-chloro-4-(2-(2-chloro-4-cyclopropylphenylsulfonamido)-4-(cyclobutylcarbamoyl)phenoxy)-2-fluorophenyl)acetic acid (B.7). MS ESI (neg.) m/e: 605.0 (M−H) $^1$H NMR (400 MHz) (MeOD) □ 8.08 (d, J=1.8 Hz, 1H); 7.77 (d, J=8.2 Hz, 1H); 7.56 (dd, J=1.9, 8.6 Hz, 1H); 7.48 (d, J=7.4 Hz, 1H); 7.09 (s, 1H); 6.98 (d, J=8.2 Hz, 1H); 6.65 (d, J=8.6 Hz, 1H); 6.27 (d, J=9.9 Hz, 1H); 4.44-4.52 (m, 1H), 3.68 (s, 2H); 2.34-2.67 (b, 2H); 2.10-2.14 (m, 2H); 1.87-1.91 (m, 1H); 1.76-1.82 (m, 2H); 1.05-1.10 (m, 2H); 0.72-0.75 (m, 2H).

2-(5-chloro-4-(2-(2-chloro-4-methylphenylsulfonamido)-4-((1-methylcyclobutyl)carbamoyl)phenoxy)-2-fluorophenyl)acetic acid (B.8). MS ESI (pos.) m/e: 595.0 (M+H). $^1$H NMR (400 MHz) (MeOD) □ 8.00 (d, J=2.10 Hz, 1H); 7.74 (d, J=8.1 Hz, 1H); 7.48 (dd, J=8.6, 2.1 Hz, 1H); 7.41 (d, J=7.5 Hz, 1H); 7.60 (s, 1H); 7.09 (d, J=8.1 Hz, 1H); 6.61 (d, J=8.6, 1H); 6.11 (d, J=10.1 Hz, 1H); 3.60 (s, 2H); 2.30-2.38 (m, 2H); 2.26 (s, 3H); 1.98-2.08 (m, 2H); 1.81-1.88 (m, 2H); 1.6 (m, 3H).

2-(5-chloro-4-(2-(2-chloro-4-(trifluoromethoxy)phenylsulfonamido)-4-((1-methylcyclobutyl) carbamoyl)phenoxy)-2-fluorophenyl)acetic acid (B.9). MS ESI (pos.) m/e: 665.0 (M+H) $^1$H NMR (400 MHz) (MeOD) □ 8.05 (d, J=3.3 Hz, 1H); 8.04 (d, J=3.3 Hz, 1H); 7.58 (dd, J=8.6, 2.1 Hz, 1H); 7.48 (d, J=7.5 Hz, 1H); 7.42 (s, 1H); 7.28 (d, J=8.8 Hz, 1H); 6.67 (d, J=8.6 Hz, 1H); 6.48 (d, J=9.9 Hz, 1H); 3.68 (s, 2H); 2.37-2.45 (m, 2H); 2.09-2.15 (m, 2H); 1.88-1.95 (m, 2H); 1.59 (s, 3H).

2-(5-chloro-4-(2-(2-chloro-4-(trifluoromethyl)phenylsulfonamido)-4-((1-methylcyclobutyl) carbamoyl)phenoxy)-2-fluorophenyl)acetic acid (B.10). MS ESI (pos.) m/e: 649.0 (M+H) $^1$H NMR (400 MHz) (MeOD) □ 8.11 (d, J=8.2 Hz, 1H); 8.03-8.04 (m, 1H); 7.79 (s, 1H); 7.66 (d, J=8.3 Hz, 1H); 7.58-7.61 (m, 1H); 7.45 (d, J=7.5 Hz, 1H); 6.68 (d, J=8.6, 1.8 Hz, 1H); 6.42 (d, J=9.9, 1.8 Hz, 1H); 3.66 (s, 2H); 2.38-2.45 (m, 2H); 2.09-2.15 (m, 2H); 1.90-1.96 (m, 2H); 1.56 (s, 3H).

2-(5-chloro-4-(2-(2-chloro-4-(trifluoromethyl)phenylsulfonamido)-4-(tert-pentylcarbamoyl)phenoxy)-2-fluorophenyl)acetic acid (B.11). MS ESI (pos.) m/e: 651.0 (M+H). $^1$H NMR (400 MHz) (CDCl$_3$) □ 8.11 (d, J=8.3 Hz, 1H); 7.97 (d, J=2.0 Hz, 1H); 7.84 (s, 1H); 7.65 (d, J=8.2 Hz, 1H); 7.54 (dd, J=9.0, 2.0 Hz, 1H); 7.44 (d, J=7.5 Hz, 1H); 6.68 (d, J=8.6 Hz, 1H); 6.43 (d, J=10.0 Hz, 1H); 3.66 (s, 2H); 1.87 (q, J=7.4 Hz, 2H), 1.41 (s, 6H); 0.91 (t, J=7.4 Hz, 3H).

2-(5-chloro-4-(2-(2-chloro-4-methylphenylsulfonamido)-4-(tert-pentylcarbamoyl)phenoxy)-2-fluorophenyl)acetic acid (B.12). MS ESI (pos.) m/e: 597.1.0 (M+H). $^1$H NMR (400 MHz) (CDCl$_3$) □ 7.98 (d, J=2.0 Hz, 1H); 7.81 (d, J=8.1 Hz, 1H); 7.47-7.50 (m, 2H); 7.23 (s, 1H); 7.16 (d, J=8.0 Hz 1H); 6.68 (d, J=8.6 Hz, 1H); 6.21 (d, J=10.0 Hz, 1H); 3.67 (s, 2H); 2.32 (s, 3H); 1.87 (q, J=7.4 Hz, 2H), 1.40 (s, 6H); 0.91 (t, J=7.4 Hz, 3H).

Example 13

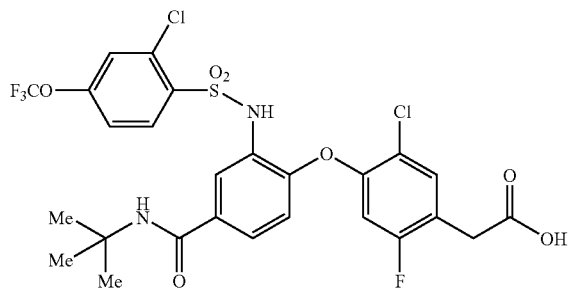

2-(4-(4-(tert-butylcarbamoyl)-2-(2-chloro-4-(trifluoromethoxy)phenylsulfonamido)phenoxy)-5-chloro-2-fluorophenyl)acetic acid (D)

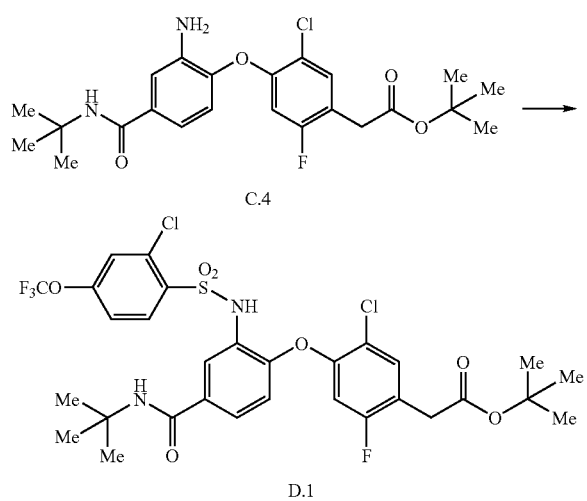

tert-butyl 2-(4-(4-(tert-butylcarbamoyl)-2-(2-chloro-4-(trifluoromethoxy)phenylsulfonamido)phenoxy)-5-chloro-2-fluorophenyl)acetate (D.1). Sulfonylation of the aniline C.4 was carried out according to the method of Example C (Scheme C.5). Ester D.1 was obtained as a light yellow glassy solid in 84% yield. $^1$H NMR (500 MHz) (CDCl$_3$) ☐ 8.10 (d, J=8.8 Hz, 1H); 7.96 (s, 1H); 7.67 (s, 1H); 7.47 (dd, J=2.1, 8.5 Hz, 1H); 7.39 (d, J=7.4 Hz, 1H); 7.27 (s, 1H); 7.19 (dd, J=1.0, 8.8 Hz, 1H); 6.64 (d, J=8.6 Hz, 1H); 6.39 (d, J=9.6 Hz, 1H); 5.91 (s, 1H); 3.57 (s, 2H); 1.49 (s, 9H); 1.48 (s, 9H).

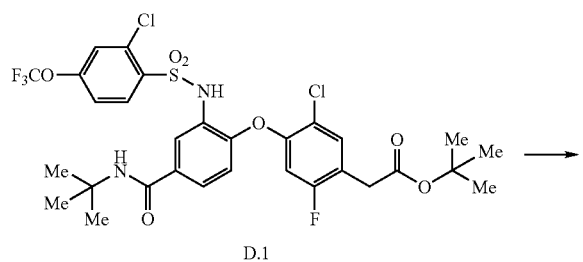

2-(4-(4-(tert-butylcarbamoyl)-2-(2-chloro-4-(trifluoromethoxy)phenylsulfonamido) phenoxy)-5-chloro-2-fluorophenyl)acetic acid (D). Hydrolysis of the tert-butyl ester was carried out according to the method of Example C (Scheme C.6). Acid D was obtained as a colorless solid in 98% yield. LC-MS ESI (neg.) m/e: 651.0 (M–H). $^1$H NMR (500 MHz) (CDCl$_3$) ☐ 8.07 (d, J=8.8 Hz, 1H); 7.93 (d, J=2.2 Hz, 1H); 7.73 (s, 1H); 7.49 (dd, J=1.9, 8.6 Hz, 1H); 7.38 (d, J=7.3 Hz, 1H); 7.22 (s, 1H); 7.17 (d, J=8.6 Hz, 1H); 6.62 (d, J=8.6 Hz, 1H); 6.38 (d, J=9.5 Hz, 1H); 5.94 (s, 1H); 3.67 (s, 2H); 1.47 (s, 9H) ppm.

Example 14

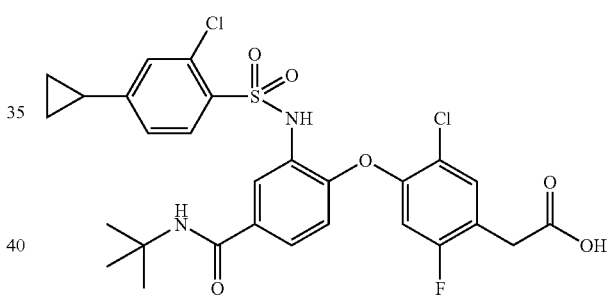

2-(4-(4-(tert-butylcarbamoyl)-2-(2-chloro-4-cyclopropylphenylsulfonamido) phenoxy)-5-chloro-2-fluorophenyl)acetic acid (C)

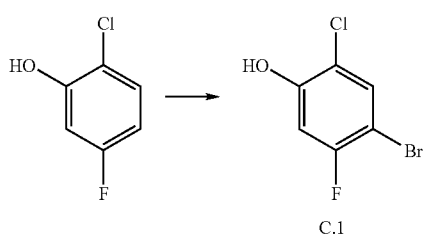

4-bromo-2-chloro-5-fluorophenol (C.1). 2-Chloro-5-fluorophenol (24.1 g, 165 mmol) was dissolved in anhydrous chloroform (200 mL), heated to 75° C. and treated with a solution of bromine (8.5 mL, 165 mmol) in anhydrous chloroform (40 mL) added dropwise over 5 minutes. After 3 hours the reaction was treated with additional bromine (1.7 mL, 33 mmol) in anhydrous chloroform (15 mL) and stirred at 75° C.

After 2 hours, the reaction was cooled to room temperature and treated with dichloromethane (300 mL) and Na₂S₂O₃ (100 mL, saturated aqueous solution). After mixing vigorously, the layers were separated and the organic layer was dried over MgSO₄, filtered and concentrated under reduced pressure. The resulting yellow liquid was purified by vacuum distillation. Compound C.1 (22.3 g, 60%) was obtained as a colorless liquid. LC-MS ESI (neg.) m/e: 224.9 (M−H). ¹H NMR (400 MHz) (CDCl₃) ☐ 7.51 (d, J=6.9 Hz, 1H); 6.85 (d, J=9.2 Hz, 1H); 5.69 (s, 1H).

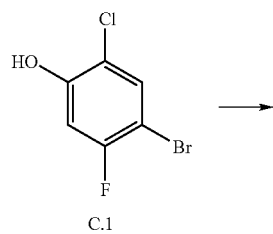

4-(4-bromo-2-chloro-5-fluorophenoxy)-N-tert-butyl-3-nitrobenzamide (C.2). Compound C.1 (13.0 g, 58.0 mmol) was dissolved in DMSO (140 mL) and treated with Cs₂CO₃ (24.6 g, 75.4 mmol). After 10 minutes N-tert-butyl-4-chloro-3-nitrobenzamide (A.5) (12.9 g, 50.2 mmol) was added in one portion and the resulting mixture was heated to 75° C. After 18 hours the reaction mixture was cooled to room temperature and treated with ethyl acetate (450 mL) and water (200 mL). The separated organic layer was washed with H₂O (2×150 mL), dried over MgSO₄, filtered and concentrated under reduced pressure. The resulting brown solid was dissolved in hot ethyl acetate (200 mL) and poured into hexane (200 mL). The precipitate was filtered and washed with cold hexane (50 mL). Compound C.2 (16.1 g, 72%) was obtained as a white solid. LC-MS ESI (pos.) m/e: 445.0 (M+H). ¹H NMR (400 MHz) (CDCl₃) ☐ 8.32 (d, J=2.1 Hz, 1H); 7.97 (dd, J=8.6, 2.1 Hz, 1H); 7.72 (d, J=6.9 Hz, 1H); 6.91 (dd, J=19.0, 8.6 Hz, 2H); 5.93 (s, 1H); 1.50 (s, 9H).

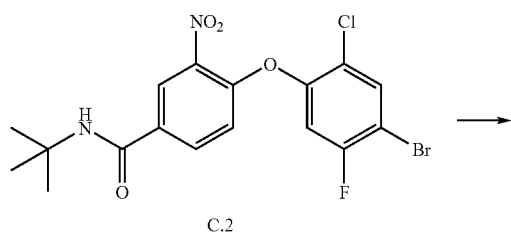

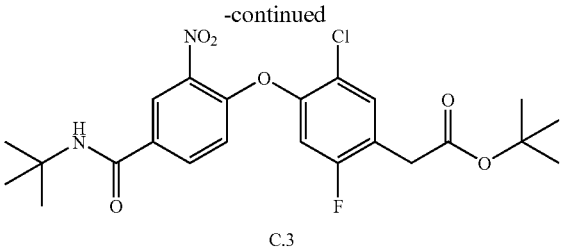

tert-butyl 2-(4-(4-(tert-butylcarbamoyl)-2-nitrophenoxy)-5-chloro-2-fluorophenyl)acetate (C.3). Compound C.2 (17.38 g, 39.1 mmol) was dissolved in anhydrous THF (150 mL) and the mixture was degassed for 20 minutes with a flow of nitrogen gas. Pddba₂ (672 mg, 1.17 mmol) and CTC-Q-Phos (833 g, 1.17 mmol) were then added in one portion to the stirred reaction mixture. After 10 minutes a 0.5 M solution of 2-tert-butoxy-2-oxoethylzinc chloride (117.3 mL, 58.6 mmol) in Et₂O was added dropwise via an addition funnel over 10 minutes. After the addition was completed the reaction was heated to reflux. After 1 hour the reaction was cooled to room temperature and the mixture was dissolved in ethyl acetate (400 mL) and water (200 mL). The separated organic layer was dried over MgSO₄, filtered and concentrated under reduced pressure. The residue was purified by flash chromatography (silica gel, 15% ethyl acetate in hexane eluent). Compound C.3 (13.2 g, 70%) was obtained as a pale yellow solid. LC-MS ESI (pos.) m/e: 481.1 (M+H). ¹H NMR (400 MHz) (CDCl₃) ☐8.29 (d, J=2.1 Hz, 1H); 7.89 (dd, J=8.6, 2.1 Hz, 1H); 7.35 (d, J=7.3 Hz, 1H); 6.80 (dd, J=8.6, 7.3 Hz, 2H); 6.43 (s, 1H); 3.48 (s, 2H); 1.40 (s, 18H).

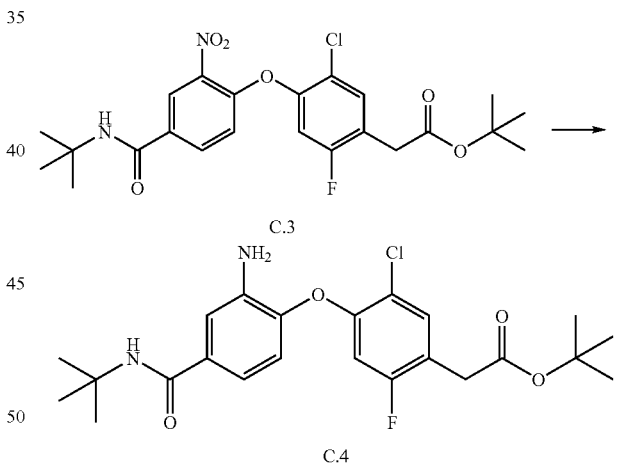

tert-butyl 2-(4-(2-amino-4-(tert-butylcarbamoyl)phenoxy)-5-chloro-2-fluorophenyl)acetate. Compound C.3 (13.2 g, 27.5 mmol) was dissolved in acetic acid (108 mL) and water (72 mL), treated with iron powder (7.7 g, 137.5 mmol) and then heated to 65° C. After 3 hours the reaction was concentrated under reduced pressure and the resulting residue was diluted with ethyl acetate (500 mL). NaHCO₃ (saturated aqueous solution, 200 mL) was carefully added dropwise and the separated organic layer was dried over MgSO₄, filtered and concentrated under reduced pressure. The residue was purified by flash chromatography (silica gel, 10% MeOH in CH₂Cl₂ eluent). Compound C.4 (9.2 g, 74%) was isolated as a white foam. LC-MS ESI (pos.) m/e: 451.1 (M+H). ¹H NMR (400 MHz) (CDCl₃) ☐7.33 (d, J=7.5 Hz, 1H); 7.25 (s, 1H);

6.96 (d, J=7.5 Hz, 1H); 6.76 (d, J=8.2 Hz, 1H); 6.58 (d, J=10.1 Hz, 1H); 5.94 (s, 1H); 3.50 (s, 2H); 1.44 (s, 18H).

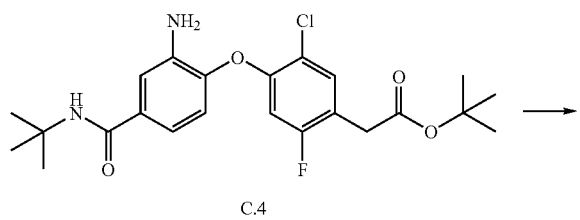

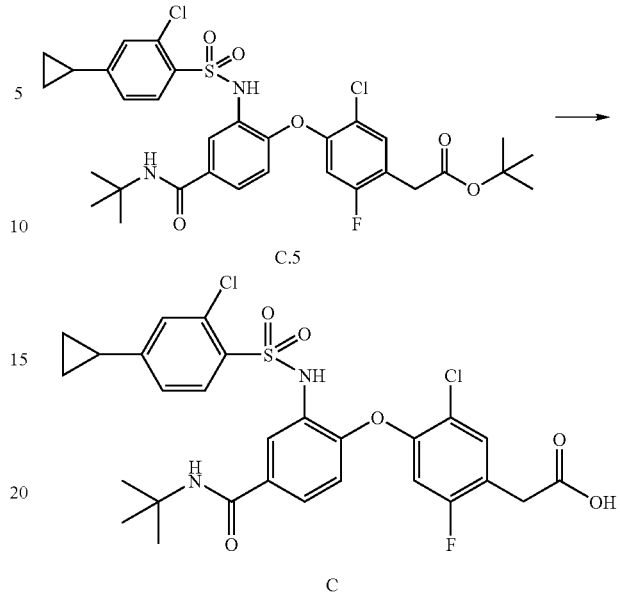

tert-butyl 2-(4-(4-(tert-butylcarbamoyl)-2-(2-chloro-4-cyclopropylphenylsulfonamido) phenoxy)-5-chloro-2-fluorophenyl)acetate (C.5). Compound C.4 (10.4 g, 23.1 mmol) was dissolved in pyridine (100 mL) and treated with 2-chloro-4-cyclopropylbenzene-1-sulfonyl chloride (6.4 g, 25.4 mmol). After 2 hours the mixture was concentrated under reduced pressure and the resulting residue was purified by flash chromatography (silica gel, 10% methanol in $CH_2Cl_2$ eluant). Compound C.5 (11.5 g, 75%) was obtained as a white solid. $^1$H NMR (400 MHz) (CDCl$_3$) □ 7.90-7.87 (m, 2H); 7.62 (s, 1H); 7.46 (d, J=8.5 Hz, 1H); 7.38 (d, J=7.3 Hz, 1H); 7.01 (s, 1H); 6.96 (d, J=8.6 Hz, 1H); 6.63 (d, J=8.6 Hz, 1H); 6.27 (d, J=9.8 Hz, 1H); 5.86 (s, 1H); 3.55 (s, 2H); 1.85-1.75 (m, 1H); 1.46 (s, 18H); 1.10-1.07 (m, 2H); 0.75-0.73 (m, 2H).

2-(4-(4-(tert-butylcarbamoyl)-2-(2-chloro-4-cyclopropylphenylsulfonamido) phenoxy)-5-chloro-2-fluorophenyl) acetic acid (C). Compound C.5 (7.2 g, 10.8 mmol) was dissolved in acetic acid (60 mL), cooled to 10° C. and treated with a 30% solution of HBr in AcOH (18 mL). After 15 minutes the reaction was warmed to room temperature for 15 minutes and then was poured into water (100 mL). The resulting precipitate was dissolved in ethyl acetate (300 mL) and then washed with $H_2O$ (100 mL) and brine (100 mL). The resulting organic layer was dried over $MgSO_4$, filtered and concentrated under reduced pressure. Compound C (3.8 g, 58%) was obtained as a white solid. LC-MS ESI (pos.) m/e: 609.0 (M+H). $^1$H NMR (400 MHz) (CDCl$_3$) □ 7.88 (s, 1H); 7.87 (d, J=6.5 Hz, 1H); 7.62 (s, 1H); 7.52 (dd, J=8.5, 2.1 Hz, 1H); 7.39 (d, J=7.4 Hz, 1H); 7.01 (s, 1H); 6.96 (d, J=8.2 Hz, 1H); 6.63 (d, J=8.5 Hz, 1H); 6.27 (d, J=9.6 Hz, 1H); 5.88 (s, 1H); 3.69 (s, 2H); 1.87-1.81 (m, 1H); 1.47 (s, 9H); 1.11-1.07 (m, 2H); 0.75-0.71 (m, 2H).

Alternative Synthesis

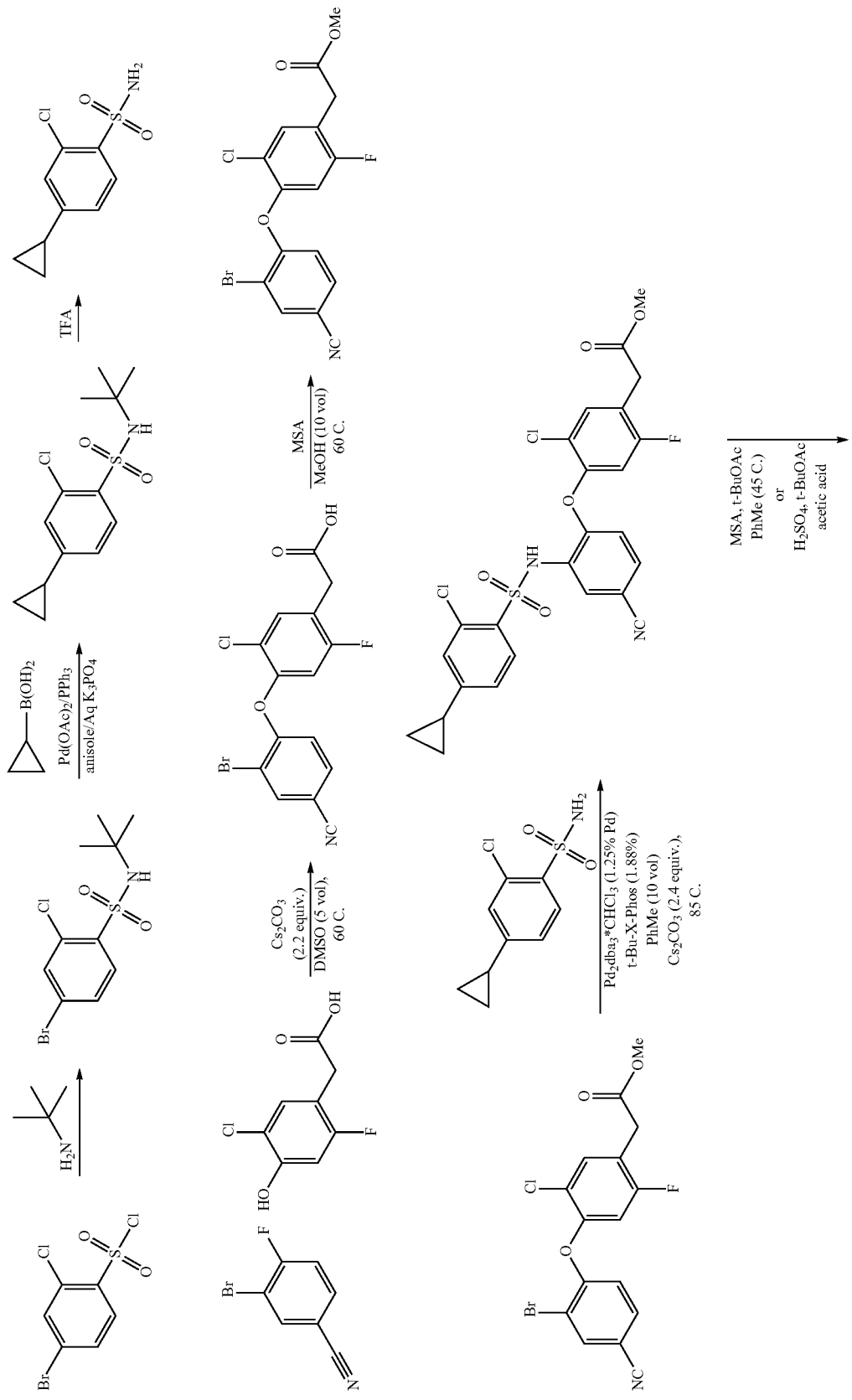

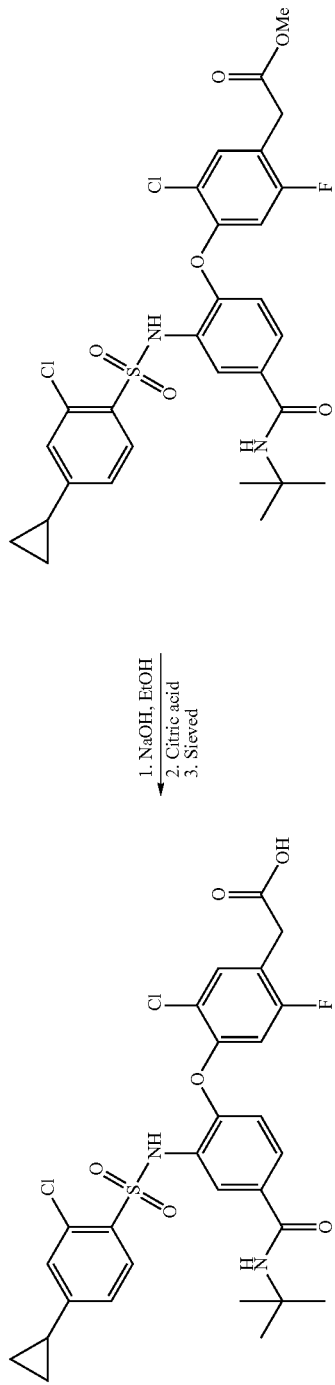

Sulfonamide Synthesis

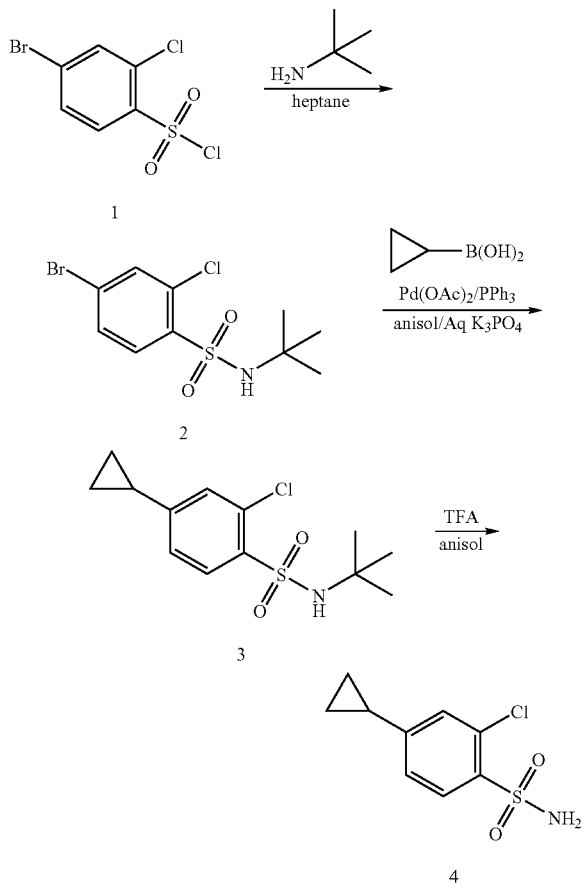

Mandelic Acid Synthesis

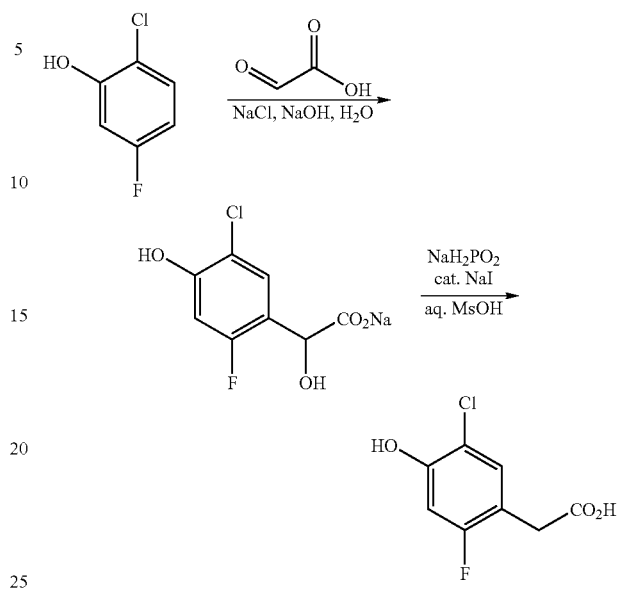

4-Bromo-2-chlorobenzene sulfonyl chloride 1 (4.0 Kg, 13.8 mol) was slurried in heptane (32 L). t-Butyl amine (7.25 L, 69 mol) was charged over 2 h, maintaining a temperature below 40° C. The slurry was aged overnight, then 5 N HCl (8.5 L, 42 mol) was charged maintaining the temperature below 40° C. The product was isolated via filtration followed by a water wash (40 L). After drying, 4.2 Kg (93%) of 2 was obtained.

150 g of 2 (0.46 mol), cyclopropyl boronic acid (50 g, 0.58 mol), potassium phosphate (195 g, 0.92 mol), palladium acetate (200 mg, 0.92 mmol), triphenyl phosphine (480 mg, 1.83 mmol), anisole (300 mL) and water (900 mL) were combined and heated to 80° C. overnight. The mixture was cooled to ambient temperature, and isopropyl acetate was added (1050 mL). The mixture was neutralized with 5N HCl (150 mL), dissolving the solids. Water was added (600 mL), and the aq phase was removed. The isopropyl acetate was distilled off at reduced pressure, and trifluoroacetic acid (410 mL) was added. The mixture was heated to 50° C. overnight, then was cooled to ambient temperature and isopropyl acetate (1500 mL) was added. The mixture was neutralized with 5N NaOH 1050 mL), then water was added (750 mL), and the aqueous phase was removed. The isopropyl acetate was distilled off at reduced pressure, and then heptane (900 mL) was added. After an overnight age, the product was isolated by filtration, with a heptane (450 mL) wash. After drying, 101 g of material was recovered, for a purity corrected yield of 91%.

The procedure used to prepare the mandelic acid reactant is outlined below:
1. Charge 2-Chloro-5-fluorophenol (1 equiv.)
2. Charge NaCl (0.86 equiv.)
3. Charge water.
4. Begin agitation.
5. Charge NaOH (10 N, 1.8 equiv.) maintaining temp below 40° C.
6. Charge Glyoxylic Acid (1.2 equiv.) dropwise maintaining temp below 40° C.
7. Adjust pH around 8.6.
8. Maintain stirring and temperature (35±5° C.) for 24 h.
9. Pull sample (HPLC). IPC: <3% starting material
10. Slowly charge HCl (5 N) maintaining temp below 40° C. pH adjust to 5.9.
11. Cool overnight
12. Stop stirring sample mother liquor. IPC: <12 mg/mL
13. Filter the white crystalline solid.
14. Wash filter cake with 10% NaCl aq solution.
15. Dry at 40° C. in a vacuum oven under nitrogen flush to constant weight.

Reduction of Mandelic Acid
1. Charge 10.93 g/1.0 equiv./of the mandelic acid sodium salt into the flask, followed by 2.44 g/0.5 equiv./of sodium hypophosphite.
2. Under nitrogen, charge 25 mL of 50% aq. methanesulfonic acid into the flask at room temperature.
3. Establish efficient stirring.
4. Heat the contents of the flask to 95±1.5° C.
5. Under nitrogen, slowly add a solution of 1.023 g/0.15 equiv./sodium iodide and 3.655 g/0.75 equiv./sodium hypophosphite in 25 mL 50% aq. methanesulfonic acid. Continue stirring the homogeneous reactor content at 95±1.5° C. until conversion reaches ≧99% LCAP product.
6. Stop heating. Slowly cool to 55° C. over 1 h.
7. Seed at 55° C. with 50 mg. Seed holds. Hold at 55° C.±1.5° C. for at least 1 h.
8. Slowly cool to 45° C. over 1 h, then to 35° C. over 1 h, then to 0-4° C. over a period not shorter than 3 h (or overnight). Stop stirring. Draw sample for ML assay (c=8.8 mg/g).

9. Filter suspension over glass flit.
10. Use filtrate to rinse reactor & filter again. Total ML: 67.92 g (53 ml), contains 0.60 g (6.5% yield).
11. Wash filter cake by applying a single ice cold DI water rinse (10 ml). (filtrate: 16.459 g, contains 123 mg (1.3%) product
12. Dry filter cake at 45-55° C. to constant weight, delump after 3-4 h.
13. Determine weight: 8.45 g (89% corr. yield; 97.3 wt %) white, crystalline powdery solid, 99.7% LCAP {220 nm}.

Aryl Bromide Synthesis

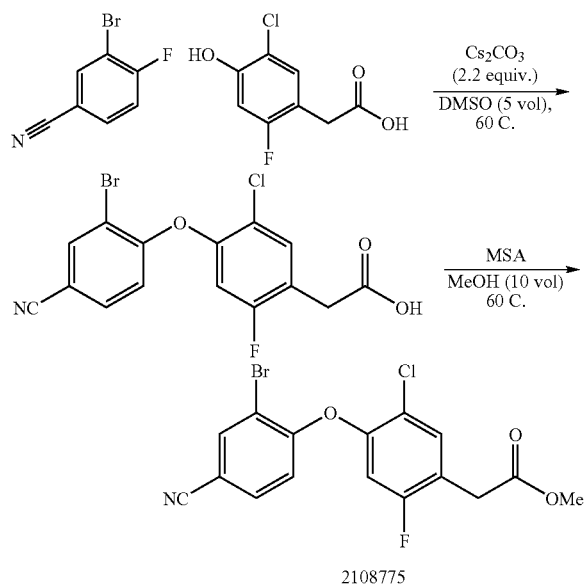

Phenyl acetic acid (1.82 Kg, 8.89 mol, 1.1 eq) and nitrile (1.62 Kg, 8.08 mol, 1.0 eq) were dissolved in DMSO (8 L) at 25° C. To this solution was added $K_2CO_3$ (2.46 Kg, 17.8 mol, 2.2 eq) in portions to control off gassing. The purple slurry was heated to 60° C. and aged overnight. Upon reaction completion the reaction mixture was inversely quenched in to a mixture of (16 L) of MTBE, (12.9 L) DI water and (3.5 L) methane sulfonic acid slowly. After mixing for 30 minutes the aqueous layer was removed and the organic layer was washed with 16 L of DI water and concentrated to dryness. MeOH (4 L) was added and the solution concentrated to dryness twice, until the residual MTBE was <5% by GC. To the product, MeOH (22 L) and 8.3 mL of methane sulfonic acid were charged, and the batch was heated to 63° C. over 15 hours, until 99% conversion. The reaction was cooled by ramping to 20° C. and the resulting suspension was filtered and washed with MeOH (2×3 L). The solid cake was dried under $N_2$ to provide 74% yield with 101.8 wt % potency and 99.5 A % purity. Chloroisomer content was 2.16 A %. A second recrystallization using 23.6 L of MeOH and heating to 68° C. obtained the desired product in 67% with 100 wt % potency, 99.7 A % purity and 0.74 A % chloroisomer content. Recrystallization process was repeated until <0.5 A % of chloroisomer content was achieved.

Pd-Catalyzed Sulfonamide Coupling 2330.9 g of methyl 2-(4-(2-bromo-4-cyanophenoxy)-5-chloro-2-fluorophenyl)acetate, 1490.3 g of 2-chloro-4-cyclopropyl-benzenesulfonamide, 47.0 g of tBu X-Phos, 4513.1 g of cesium carbonate, and 38.3 g of $Pd_2\,dba_3$*$CHCl_3$ were charged to the 100 L reactor. The reactor was purged once by evacuating it to 3 psia and then back up to atmospheric with $N_2$. 23 L of toluene were charged to the reactor and the vessel was again vacuum purged to 5 psia. The reactor jacket was set to 85° C. and agitated at 350 rpm overnight. At ~16 hours of elapsed reaction time, a sample analyzed for reaction completion confirmed 0.88% aryl bromide starting material.

6 L of purified water was charged to the reactor and another 6 L charged to the 50 L portable reactor. The reactor contents were then transferred into the 50 L portable. A 3 L portion of toluene was used to rinse the reactor and was flushed forward into the portable reactor. 6455 mL of 5N HCl were charged to the reactor over 1 hr 10 min; this rate was bounded by $CO_2$ evolution. The batch was stirred for 1 hr and a sample taken for pH confirmed pH<1. Agitation was halted for phase separation, and solids were visible precipitating out of the organic. 2.3 L of HCl were charged and the batch was agitated in an effort to dissolve the solids, but upon halting mixing they were still visible. 2.3 L of MTBE were charged, the batch was stirred, and when agitation was halted the batch phase split cleanly.

In order to remove palladium from the endl product 547.6 g of Silicycle® Si-Thiourea silica gel were charged to the reactor and agitated overnight. The batch was then filtered over a 5 um polypropylene filter cloth with 2 kg of celite 521 in order to remove the Silicycle®. 8.75 L of toluene were used to rinse the portable reactor and cake bed. The filtrate was charged back into the 50 L portable reactor and agitated overnight with an additional 255.4 g of Silicycle®. The batch was then filtered over the same celite bed, and an 8 L toluene wash was flushed from the reactor forward through the filter. An additional 2 L wash was used to clear the 50 L vessel. Sample analysis confirmed a palladium level of 13 ppm.

Ritter Reaction

To 3358 g of the benzonitrile starting material (6.1 mol, 1.0 equiv) in toluene (9 L) at 45-50° C., methanesulfonic acid (397 ml) was added followed by tert-butylacetate (8.24 L). The reaction was maintained at 45° C. After 2 h, additional MsOH (0.177 L) and tBuOAc (1.84 L) were added and the reaction was stirred until 97% conversion was reached. The reaction was diluted with toluene (13.43 L), cooled to 25° C., washed with sodium phosphate dibasic 1M aq. solution (2×4.5 vol, 15 L) and water (1×15 L). The solution was heated to 45-50° C. and concentrated to 5 vol. under reduced pressure. Additional toluene was added to readjust to 7.4 vol. (24.85 L). The solution was heated to 60° C. and n-heptane (6.21 L=1.85 vol). The solution was seeded with 1g and slowly cooled to 20° C. over a period of 4 h or overnight. The toluene/heptane ratio was adjusted to 65:35 by slowly charging n-heptane (7.17 L). The suspension was filtered to isolate white, cryst. solid. The filter cake was washed with n-heptane-toluene 35:65 (2 vol, 6.7 L) and n-heptane (2 vol, 6.7 L) at r.t. and dried at r.t. under nitrogen flush to constant weight to give 2.68 kg of Ritter product, 77%, 97 LCAP, 0.84 LCAP Cl-isomer, 9 ppm Pd.

Hydrolysis

To a slurry of the methyl ester starting material (1139 g, 1 equiv.) in ethanol (10.3 L) and water (2.9 L), 10NaOH (455 mL, 2.5 equiv.) was charged. After 100% conversion was reached the solution was polish filtered. The solution was heated to 60 C and citric acid (1.29 M, 3.6 L, 2.5 equiv.) was added. The solution was seeded with 62 g product and water (4.5 L) was charged slowly and mixture was cooled to RT. The product was isolated by filtration, washed with 1:1 ethanol/water (2.3 L), followed by water (4.5 L). The product was dried at 40° C. in a vacuum oven 1,048.5 g of title compound, 88.5% yield.

Polymorphs

Example compound 14 exists in at least six different physical forms. Anhydrous Form II free acid is the preferred embodiment. Form II is isolated from the hydrolysis of the methyl ester precursor of compound starting material according to the following procedure:

Form II

Slurry of the methyl ester starting material in (1139 g, 1 equiv.) in ethanol (10.3 L), water (2.9 L), 10N NaOH (455 mL, 2.5 equiv.). After 100% conversion was reached the solution was polish filtered. The solution was heated to 60 C and citric acid (1.29 M, 3.6 L, 2.5 equiv.) was added. The solution was seeded with 62 g product and water (4.5 L) was charged slowly and mixture was cooled to RT. The product was isolated by filtration, washed with 1:1 ethanol/water (2.3 L), and followed by water (4.5 L). The product was dried at 40° C. in a vacuum oven 1,048.5 g of Form II, 88.5% yield.

Figures 8A, 8B:
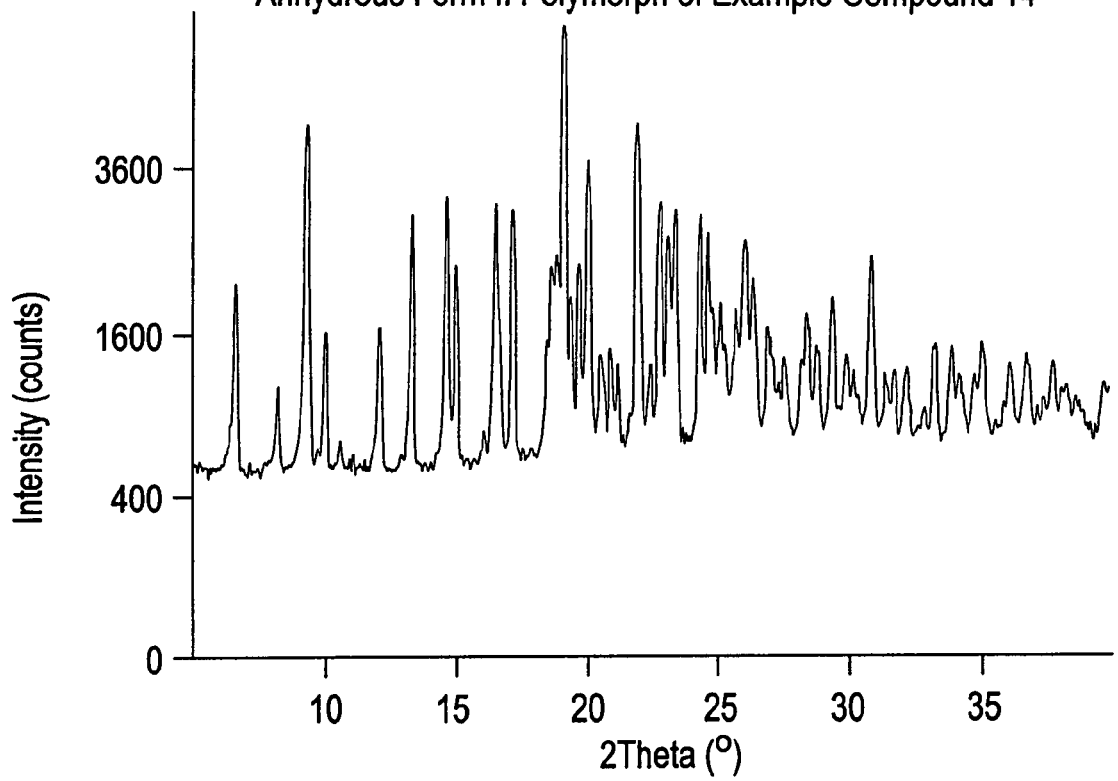
FIGS. 8A and 8B present X-Ray Powder Diffraction data obtained for Example Compound 14 Form II anhydrous polymorph.
Figure 14:
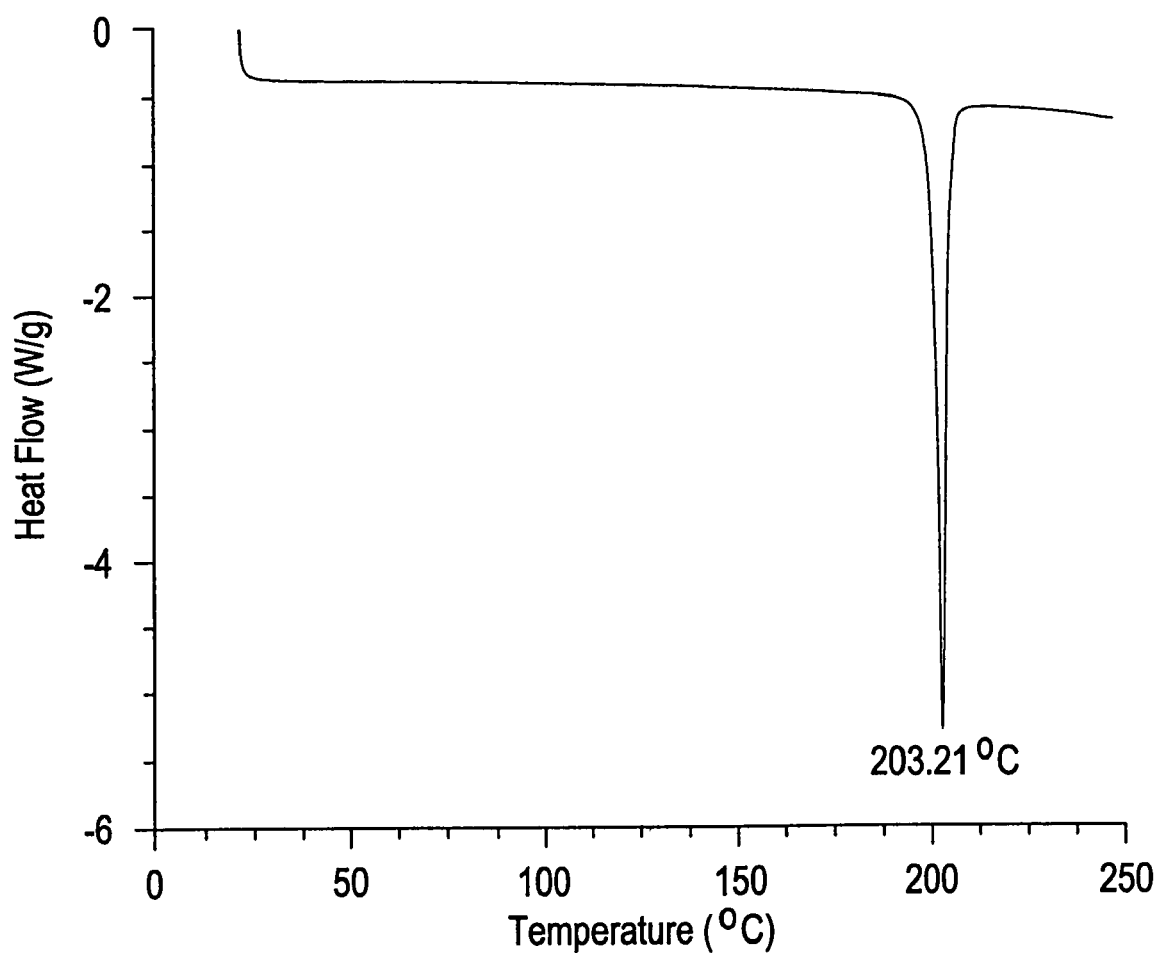
FIG. 14 illustrates a DSC thermogram obtained for Example Compound 14 Form II anhydrous polymorph, which shows a single thermal transition (an endothermic transition at around 203.21° C.).

Form II anhydrous (Form II product of previous procedure, dissolved in 7.8 vol of EtOH at 60° C. Added water as antisolvent, Seeded at 65% EtOH, Continued adding water until 50% EtOH at RT, Cooled, Filtered 104.7 g isolated—96%. Form II is anhydrous and non hygroscopic form. The form has a single thermal transition when analysed using Differential Scanning Calorimetry (DSC) with heating at 10° C. per minute (Figure #). The single thermal transition is an endothermic transition with a peak temperature around 203° C. Form II is crystalline by x-ray powder diffraction. The X-Ray Powder Diffraction Spectra, and DSC thermogram for Form II, are illustrated in FIGS. 8 and 14 respectively.

Forms I, III, IV, V and VI were prepared as follows

Figures 7A, 7B:
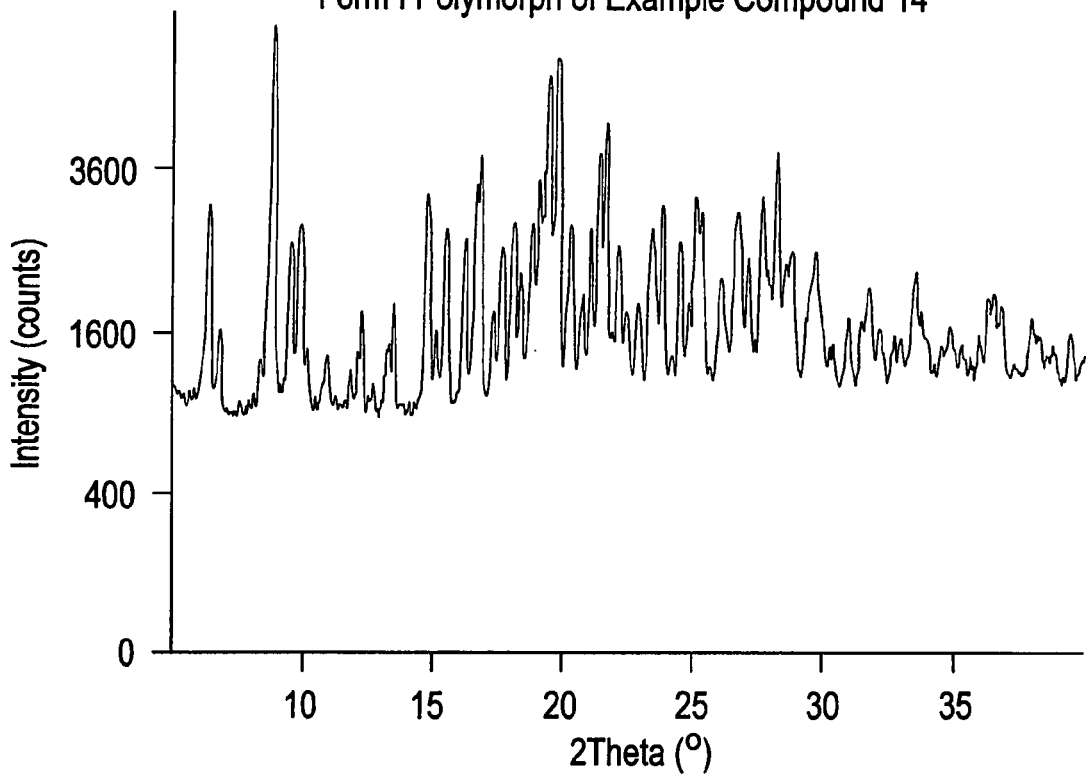
FIGS. 7A and 7B present X-Ray Powder Diffraction data obtained for Example Compound 14 Form I polymorph.

Form I anhydrous adding Heptane as anti-solvent to an IPA saturated solution of form II anhydrous. The X-Ray Powder Diffraction Spectra, and DSC thermogram for Form I, are illustrated in FIGS. 7 and 13 respectively.

Figures 9A, 9B:
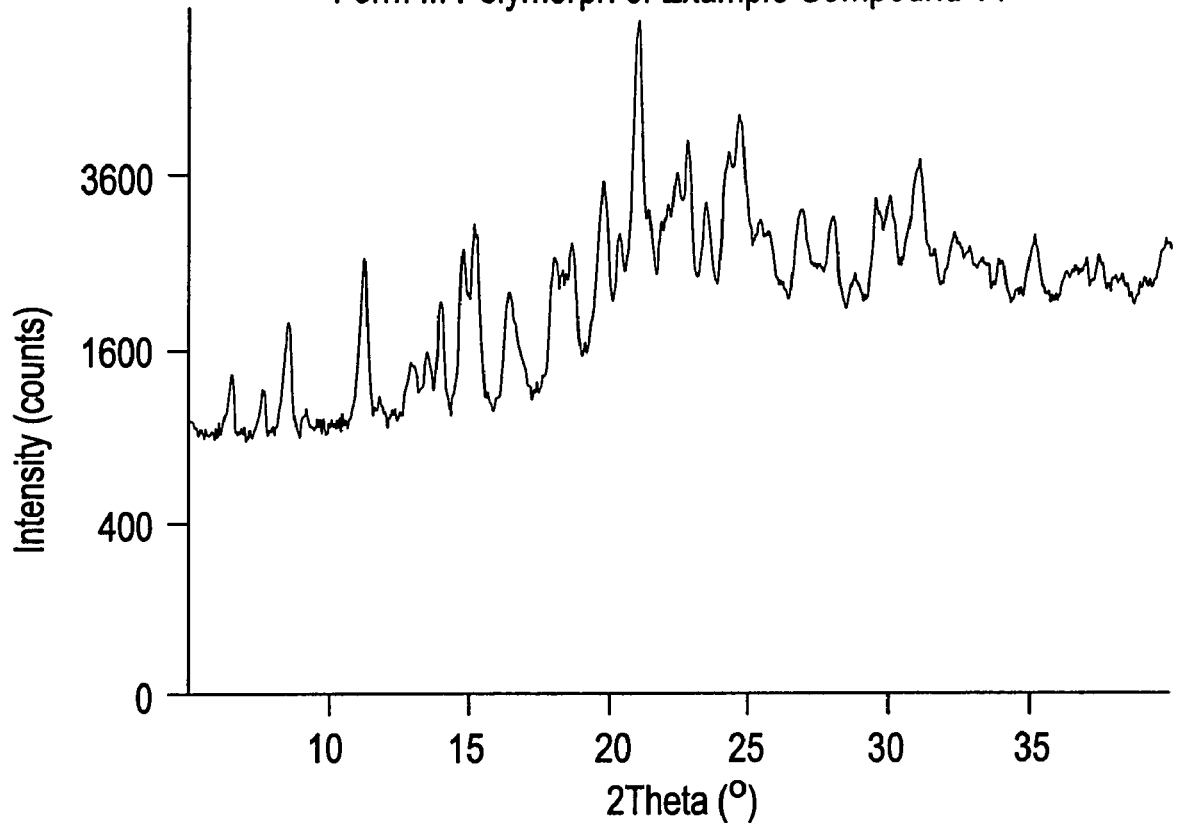
FIGS. 9A and 9B present X-Ray Powder Diffraction data obtained for Example Compound 14 Form III polymorph.
Figure 15:
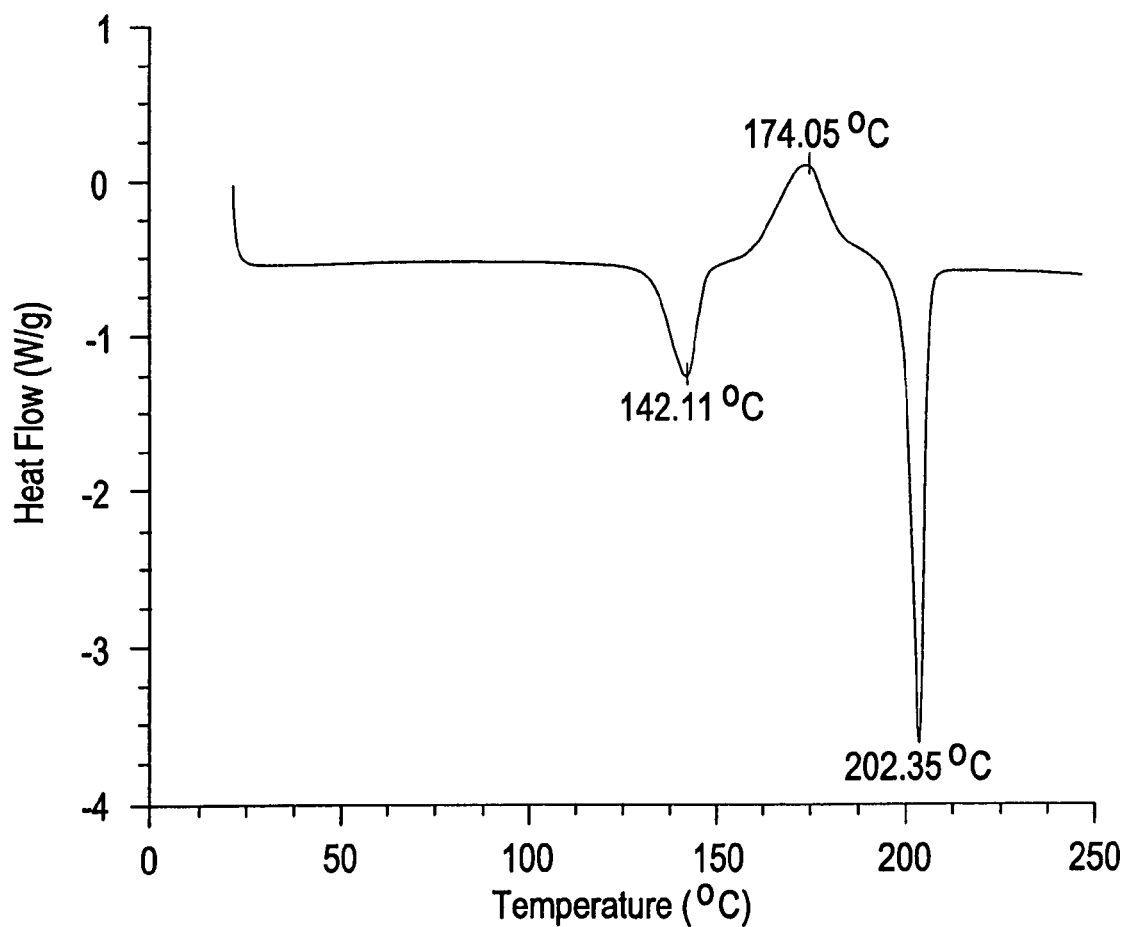
FIG. 15 illustrates a DSC thermogram obtained for Example Compound 14 Form III polymorph, which shows three thermal transitions (an endothermic transition at about 142.11° C., an exothermic transition at around 174.05° C. and an endothermic transition at around 202.35° C.).

Form III anhydrous: Form II anhydrous was generated via crash out by concentration of solvent after chromatography. The X-Ray Powder Diffraction Spectra, and DSC thermogram for Form III, are illustrated in FIGS. 9 and 15 respectively.

Figures 10A, 10B:
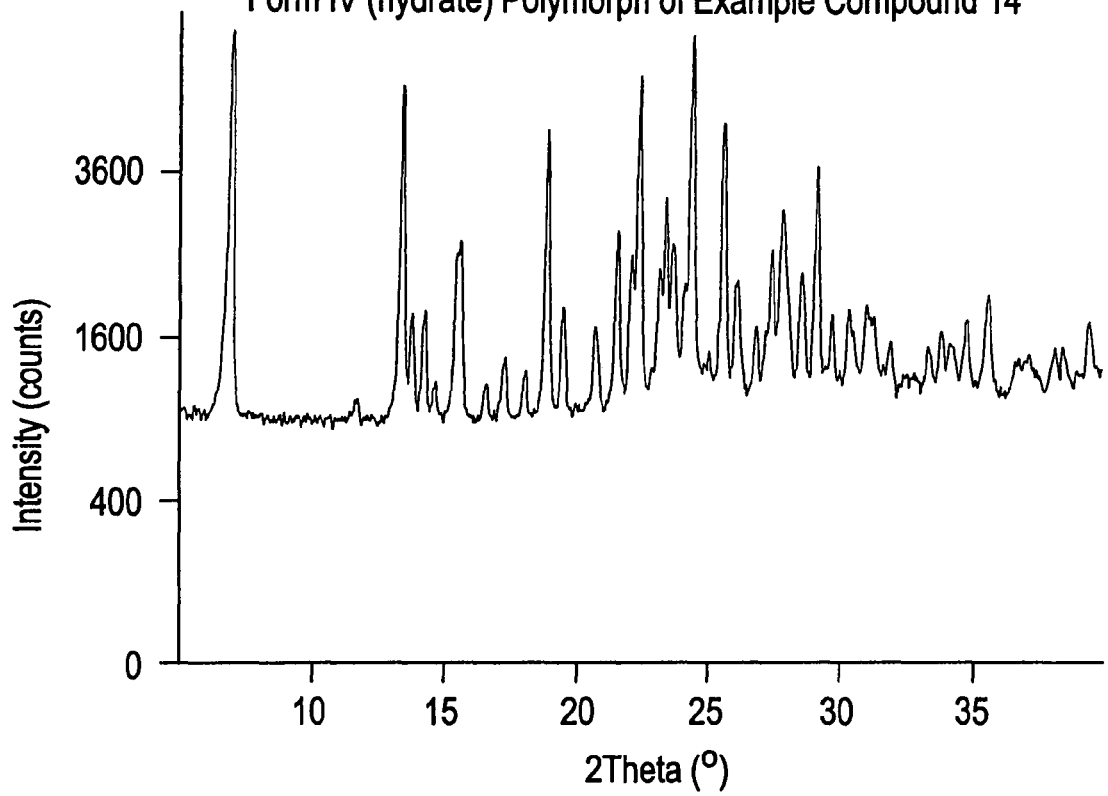
FIGS. 10A and 10B present X-Ray Powder Diffraction data obtained for Example Compound 14 Form IV polymorph.
Figure 16:
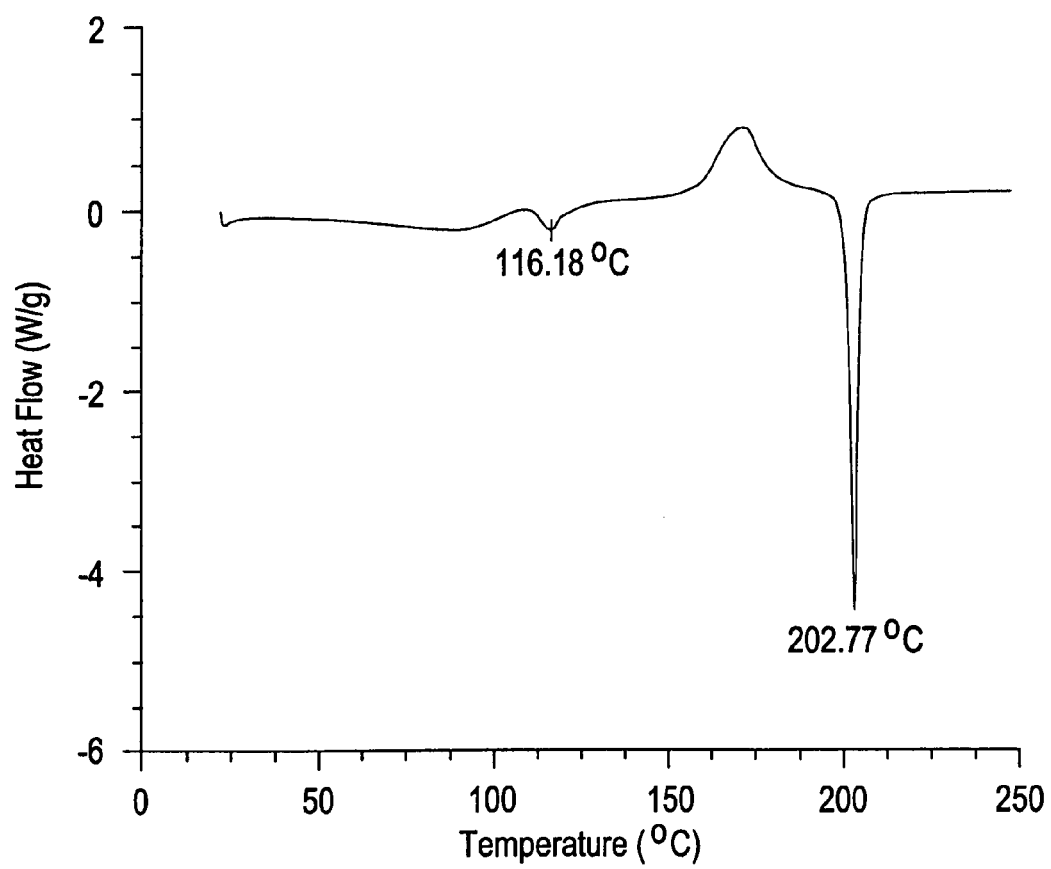
FIG. 16 illustrates a DSC thermogram obtained for Example Compound 14 Form IV polymorph, which shows two thermal transitions (an endothermic transition at about 116.18° C., and an endothermic transition at around 202.77° C.).

Form IV monohydrate (3.5 eq LiOH hydrate in 50 mL MeOH/20 mL water was added to methyl ester precursor of compound 14 and stirred at rt. Hydrolysis was complete in 1 h (HPLC). The solution was dropped in slowly to 20% (w/v) citric acid (28 mL) at 5° C. Solid precipitates were stirred for 1 h at 0-5° C., filtered, washed with water, and dried in vac. oven at 40° C., very high water conc on crystallization. The X-Ray Powder Diffraction Spectra, and DSC thermogram for Form VI, are illustrated in FIGS. 10 and 16 respectively.

Figures 11A, 11B:
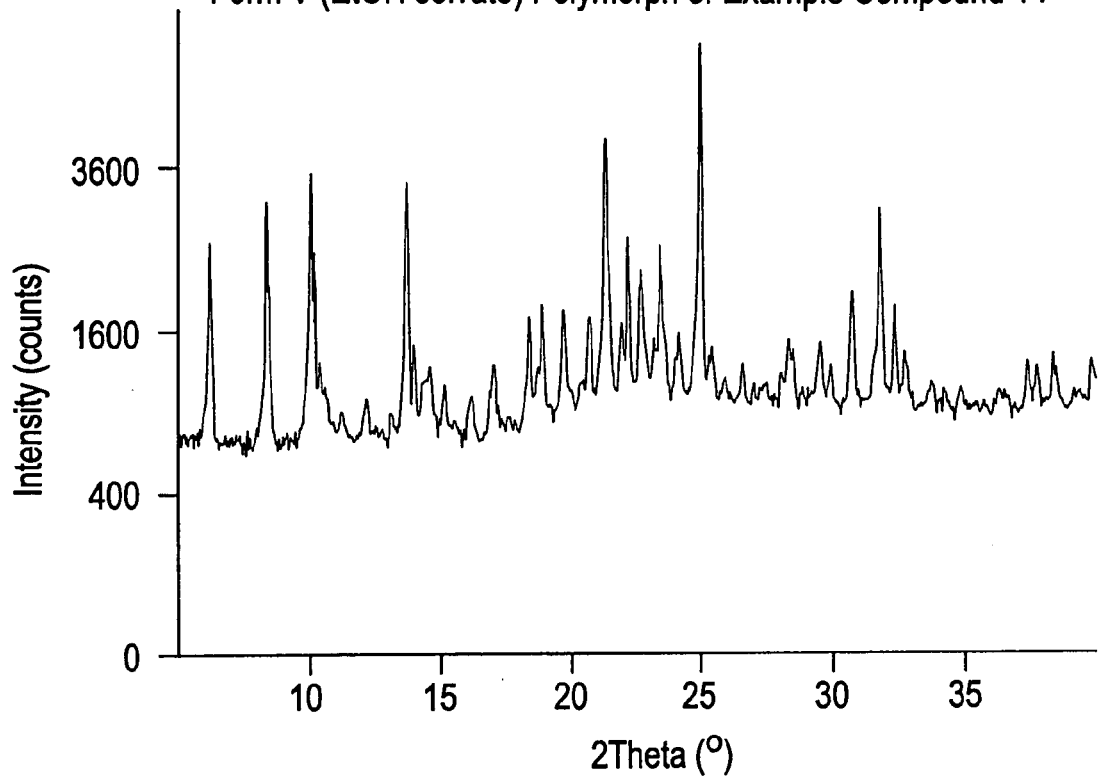
FIGS. 11A and 11B present X-Ray Powder Diffraction data obtained for Example Compound 14 Form V polymorph.
Figure 17:
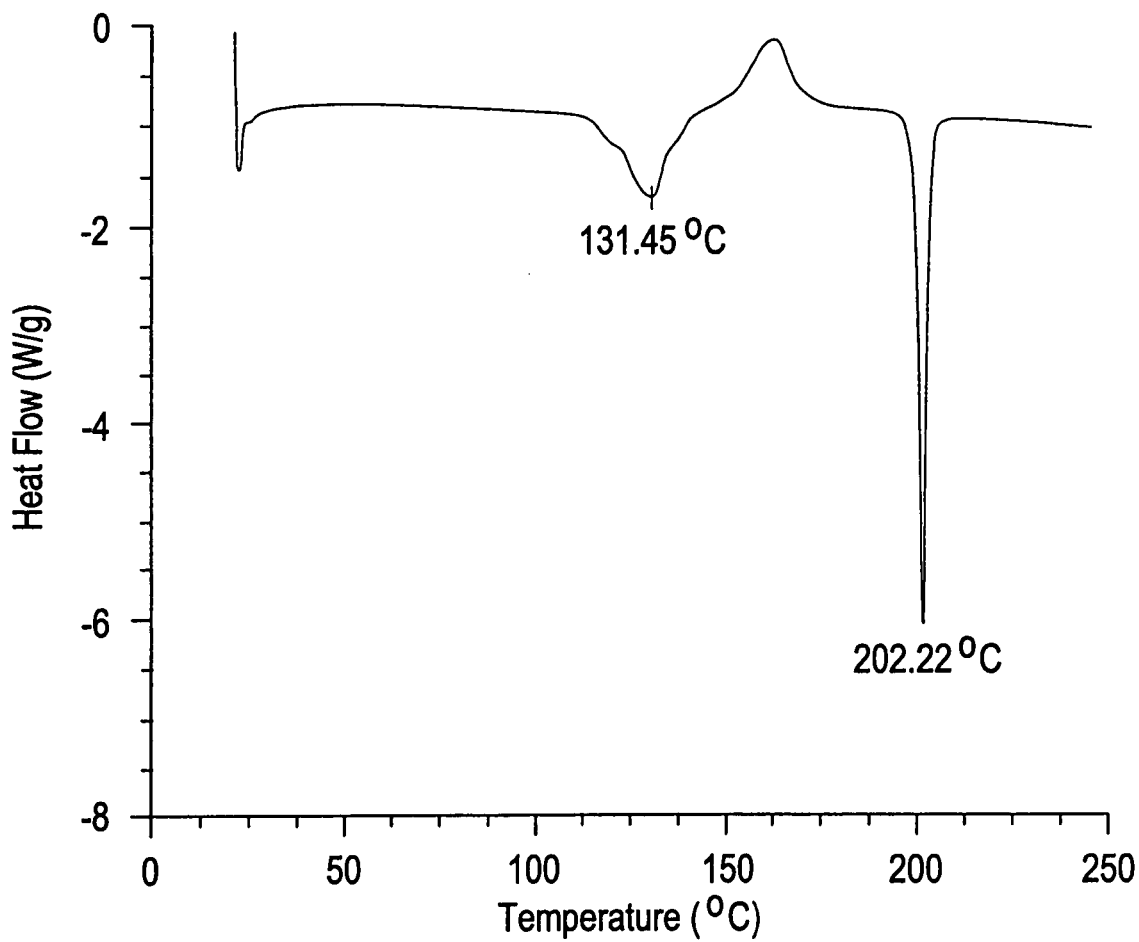
FIG. 17 illustrates a DSC thermogram obtained for Example Compound 14 Form V polymorph, which shows two thermal transitions (an endothermic transition at about 131.45° C., and an endothermic transition at around 202.22° C.).

Form V Ethanol solvate: cooling of the saturated solution of anhydrous Form II in EtOH:water (1:1) from 55 C to RT. The X-Ray Powder Diffraction Spectra, and DSC thermogram for Form V, are illustrated in FIGS. 11 and 17 respectively.

Figures 12A, 12B:
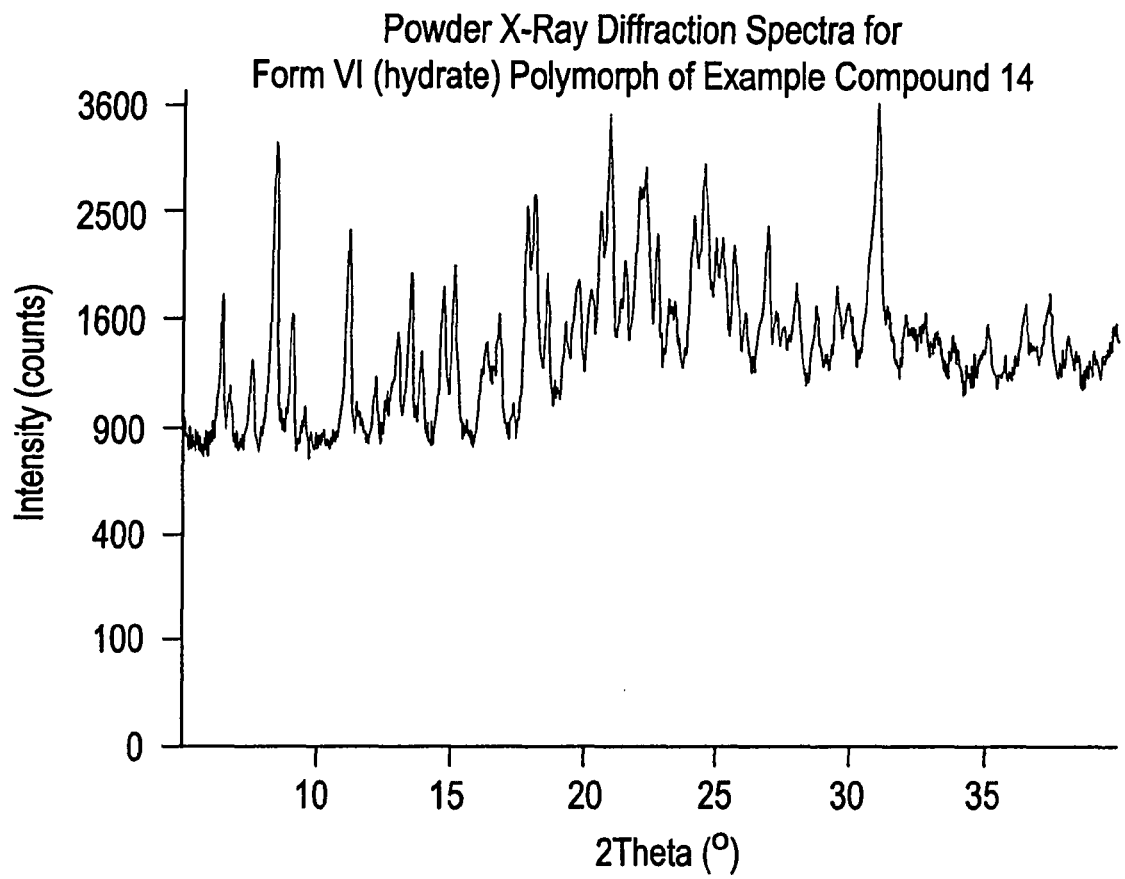
FIGS. 12A and 12B present X-Ray Powder Diffraction data obtained for Example Compound 14 Form VI polymorph.
Figure 18:
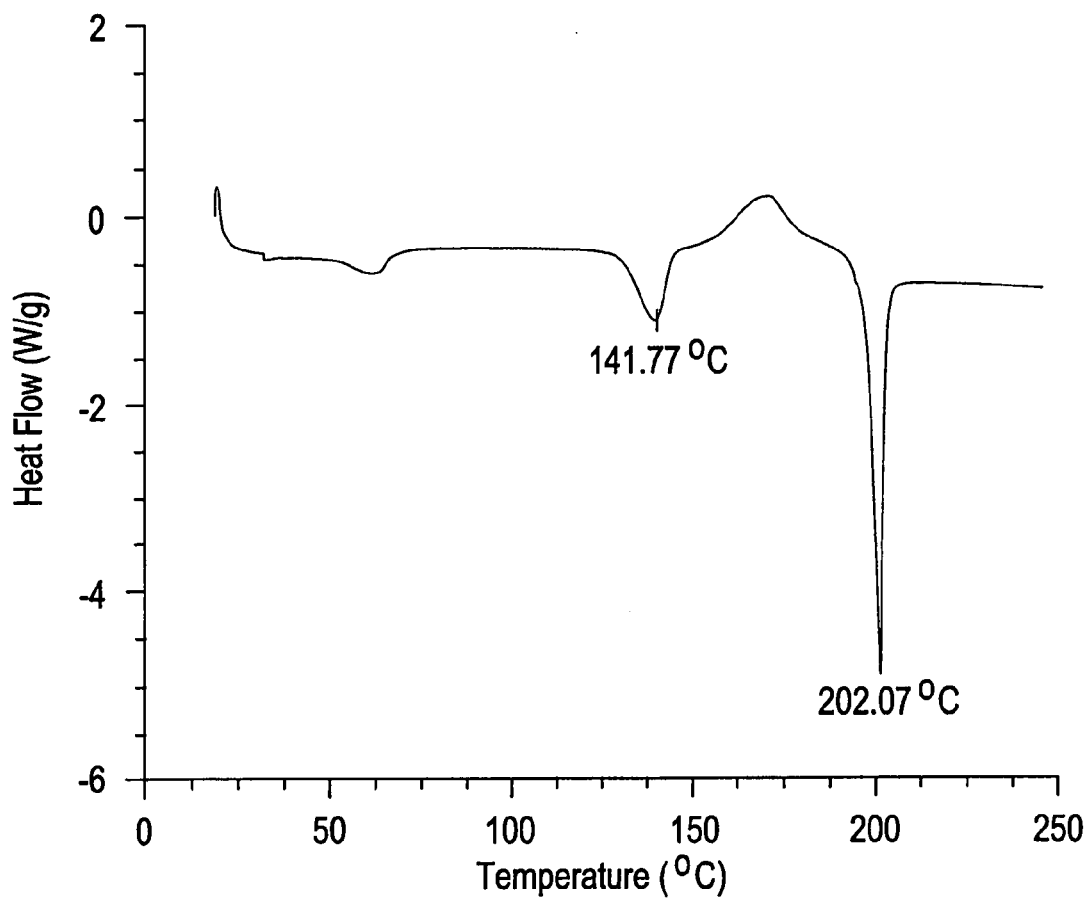
FIG. 18 illustrates a DSC thermogram obtained for Example Compound 14 Form VI polymorph, which shows two thermal transitions (an endothermic transition at about 141.77° C., and an endothermic transition at around 202.07° C.).

Form VI monohydrate: Dissolved form II anyhydrous in EtOH (10 vol) using heat. Cooled and added water in single portion, highly saturated. The X-Ray Powder Diffraction Spectra, and DSC thermogram for Form I, are illustrated in FIGS. 12 and 18 respectively.

Raman and Near IR data for polymorph Forms I through VI of Example Compound 14 are set forth in the tables provided below:

Characteristic Peaks of Compound 14 polymorphs by NIR (Resolution 4 $cm^{-1}$, diffusion reflectance mode, Antaris ™, Near-IR Analyzer, Nicolet)

| Polymorph | Region 1, $cm^{-1}$ | | | Region 2, $cm^{-1}$ | | | |
|---|---|---|---|---|---|---|---|
| Form 1 | 6760 s | 6413 m, b | | 4978 s | 4942 s | | |
| Form 2 | 6739 s | 6432 m, b | | 4969 s | 4935 m | | |
| Form 3 | 6691 s | 6466 m, b | | 4944 s | 4912 m, sh | | |
| Form 4 | 6996 m | 6720 m | 6493 w | 5220 s | 5111 w | 4971 m | 4935 m, sh |
| Form 5 | 7083 m, b | 6619 m, b | 6502 m | 5254 m | 4919 m | | |
| Form 6 | 7085 m | 6683 m, sh | 6627 m | 5249 s | 5075 w | 4919 s | |

Characteristic Peaks of Compound 14 polymorphs by Raman (Resolution 13 $cm^{-1}$, Millennia Ili Nd: YAG laser at 532 nm, Falcon II, ChemImage)

| Polymorph | N—H stretch ($cm^{-1}$) | C—H stretch ($cm^{-1}$) | C=O/C=C stetch ($cm^{-1}$) | C—N stretch/ others, $cm^{-1}$ |
|---|---|---|---|---|
| Form 1 | 3453 w | 3091 m | 1737 w | 1314 s |
| | 3263 w | 3075 m | 1623 m | 1258 m |
| | | 3035 m | 1604 m | 1218 m |
| | | 3017 m | 1591 s | |
| | | 3000 m | | |
| | | 2967 m | | |
| | | 2950 m | | |
| | | 2927 m | | |
| Form 2 | 3444 w | 3098 m | 1737 w | 1314 s |
| | 3275 w | 3088 m | 1641 m | 1258 m |
| | | 3077 m | 1618 m, sh | 1217 m |
| | | 3063 m | 1606 s | |
| | | 3011 m | 1589 s | |
| | | 2978 m | 1531 w | |
| | | 2965 m, sh | | |
| | | 2926 m | | |
| Form 3 | 3419 w | 3079 m | 1623 m | 1319 m |
| | | 3065 m, sh | 1607 m | 1258 m |
| | | 3005 m | 1589 s | 1225 m |
| | | 2977 m | 1533 w | |
| | | 2933 m | | |
| Form 4 | 3427 w | 3086 m | 1619 s | 1326 m |
| | | 3065 m | 1607 s | 1269 m |
| | | 3014 m | 1596 s | 1222 m |
| | | 2997 m | 1546 w | |
| | | 2925 m | | |
| | | 2888 w | | |
| Form 5 | 3379 w | 3079 m | 1719 w | 1322 s |
| | | 3009 m | 1616 s, sh | 1260 m |
| | | 2978 m | 1607 s | 1222 m |
| | | 2929 m | 1591 s | |
| | | | 1544 w | |
| Form 6 | 3379 w | 3079 m | 1719 w | 1322 s |
| | | 3008 m | 1617 s, sh | 1260 m |
| | | 2978 m | 1607 s | 1222 m |
| | | 2929 m | 1591 s | |
| | | | 1544 w | | s = strong,
m = medium,
w = weak,
sh = shoulder,
b = broad

Example 15

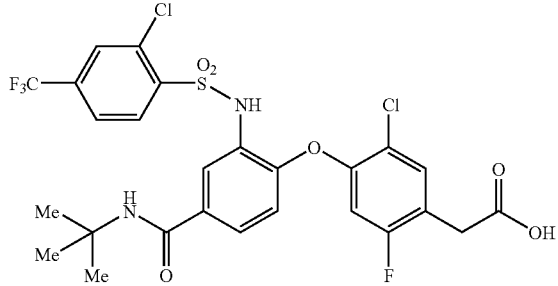

2-(4-(4-(tert-butylcarbamoyl)-2-(2-chloro-4-(trifluoromethyl)phenylsulfonamido)phenoxy)-5-chloro-2-fluorophenyl)acetic acid (F)

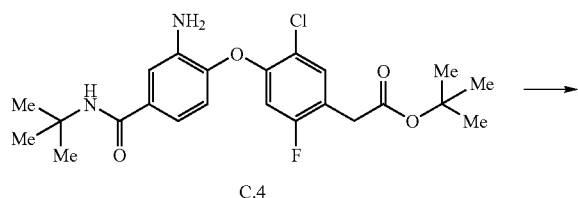

C.4

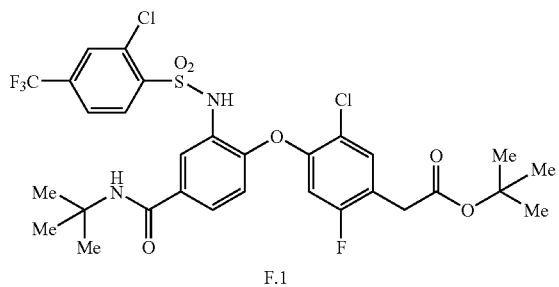

F.1 tert-butyl 2-(4-(4-(tert-butylcarbamoyl)-2-(2-chloro-4-(trifluoromethyl)phenylsulfonanido) phenoxy)-5-chloro-2-fluorophenyl)acetate (F.1). Sulfonylation of the aniline C.4 was carried out according to the method of Example C (Scheme C.5). Ester F.1 was obtained as a light yellow glassy solid. LC-MS ESI (pos.) m/e: 693.1 (M+H).

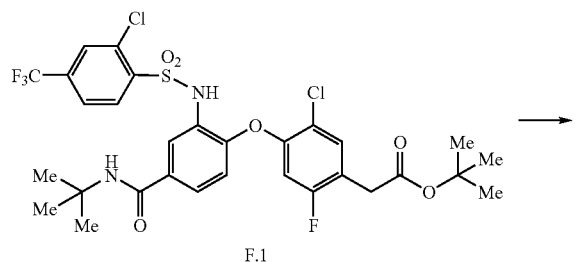

F.1

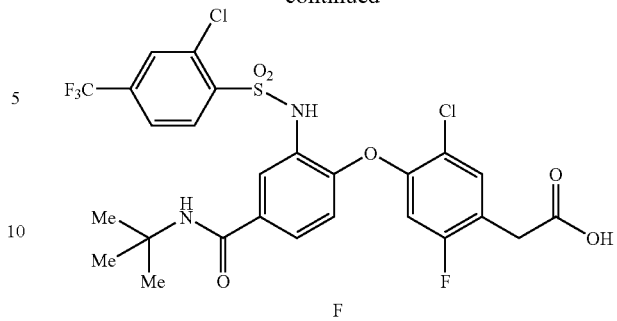

F 2-(4-(4-(tert-butylcarbamoyl)-2-(2-chloro-4-(trifluoromethyl)phenylsulfonamido)phenoxy)-5-chloro-2-fluorophenyl)acetic acid (F). Hydrolysis of the tert-butyl ester was carried out according to the method of Example C (Scheme C.6). Acid F was obtained as a colorless solid in 72% yield. LC-MS ESI (neg.) m/e: 651.0 (M−H). $^1$H NMR (500 MHz) (d$_6$-DMSO) □ 12.58 (br s, 1H); 10.60 (br s, 1H); 8.02 (d, J=8.0 Hz, 1H); 7.94 (d, J=1.2 Hz, 1H); 7.90 (d, J=2.2 Hz, 1H); 7.83 (s, 1H); 7.75 (dd, J=1.2, 8.3 Hz, 1H); 7.67 (dd, J=2.2, 8.6 Hz, 1H); 7.53 (d, J=10.2 Hz, 1H); 6.73 (d, J=7.6 Hz, 1H); 6.41 (d, J=10.2 Hz, 1H); 3.61 (s, 2H); 1.38 (s, 9H).

Biological Testing

Human CRTH2 Binding Assay

Full-length human CRTH2 cDNA was generated by polymerase chain reaction (PCR) using human genomic DNA as template and subsequently cloned into pCDNA3.1(+) (Invitrogen), generating a CRTH2 expression plasmid pHLT124. The plasmid was transfected into 293 cells, which normally express CRTH2, using LipofectAMINE™ reagents (Gibco/BRL). G418 (800 mg/mL) was added to the culture 48 h after transfection and cells were maintained under selection for 3 weeks to ensure that all surviving cells stably expressed CRTH2. These cells are labeled as 293(124) hereafter.

$^3$H-PGD$_2$ binding assay was performed using 293(124) cells. In brief, cells were washed and suspended in RPMI containing 0.5% BSA and 20 mM HEPES. Each assay contained 25,000 cells, appropriate amount of test compound when necessary and a mixture of 1 nM $^3$H-PGD$_2$ (Amersham Pharmacia Biotech) and 30 nM of unlabeled PGD$_2$ (Cayman Chemicals) in 200 mL final volume. The cell mixture was incubated at room temperature for 2.5 h with shaking and the cells were separated from free $^3$H-PGD$_2$ and transferred onto a filter plate using a cell harvester. Radioactivity bound to the cells was measured on a liquid scintillation counter. Nonspecific binding was determined in the presence of 10 mM of unlabeled PGD$_2$.

Modulation of CRTH2 and/or one or more other PGD$_2$ receptors by test compounds can be assessed by other in vitro and in vivo assays. Examples of such assays include measuring second messenger (e.g., cAMP, IP$_3$ or Ca$^{2+}$) levels, ion flux, phosphorylation levels, transcription levels, and the like. Recombinant or naturally occurring CRTH2 polypeptides and/or other PGD$_2$ receptor peptides can be used and the protein can be isolated, expressed in a cell, expressed in a membrane derived from a cell, expressed in tissue or in an animal. Signal transduction can also be examined in vitro with soluble or solid state reactions, using a chimeric molecule such as an extracellular domain of a receptor covalently linked to a heterologous signal transduction domain, or a heterologous extracellular domain covalently linked to the transmembrane and/or cytoplasmic domain of a receptor. Gene amplification can also be examined. Furthermore, ligand-binding domains of the protein of interest can be used in vitro in soluble or solid state reactions to assay for ligand binding.

CRTH2-G-protein or another $PGD_2$ receptor-G-protein interactions can also be examined, by, for example, analysis of binding of the G-protein to the receptor or its release from the receptor.

The compounds exemplified herein have been tested for both CRTH2 and DP activity, and the measured $IC_{50}$ values are provided below in TABLE 1. The corresponding activities of AMG 009, as well as the closest compounds exemplified in WO 04/058164 are also provided below in REFERENCE TABLE 2 for purposes of comparison. As can be readily seen, the compounds of the present invention are significantly more potent DP inhibitors (especially in plasma and/or whole blood) than AMG 009 and the other prior art compounds. At the same time the compounds of the present invention either maintain or improve upon the CRTH2 activity found in the prior art compounds—resulting in a significant improvement of the balance between CRTH2 activity and DP activity.

TABLE 1

| Example Compound | CRTH2 $IC_{50}$ (nM) | | | DP $IC_{50}$ (nM) | | |
|---|---|---|---|---|---|---|
| | Buffer | Plasma | whole blood | Buffer | Plasma | whole blood |
| (structure 1) | 4.6 | 10.9 | ND | 5.9 | 52.5 | ND |
| (structure 2) | 3.3 | 6.1 | ND | 5.6 | 17.2 | ND |
| (structure 3) | 3.5 | 8.1 | 1.1 | 12.6 | 43.0 | 26.6 |

TABLE 1-continued
| Example Compound | CRTH2 IC$_{50}$ (nM) | | | DP IC$_{50}$ (nM) | | |
|---|---|---|---|---|---|---|
| | Buffer | Plasma | whole blood | Buffer | Plasma | whole blood |
| 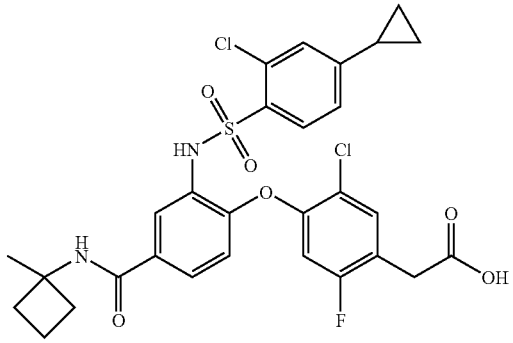 | 3.9 | 7.6 | ND | 4.4 | 25.7 | ND |
| 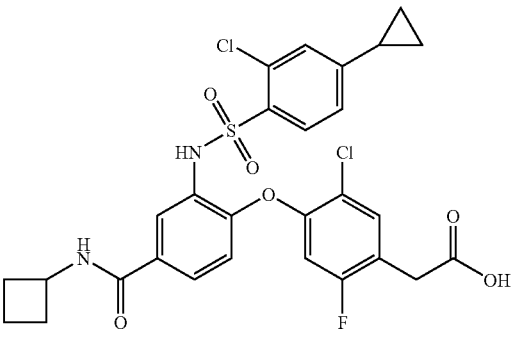 | 3.3 | 7.9 | 0.5 | 4.6 | 18.0 | 0.6 |
| 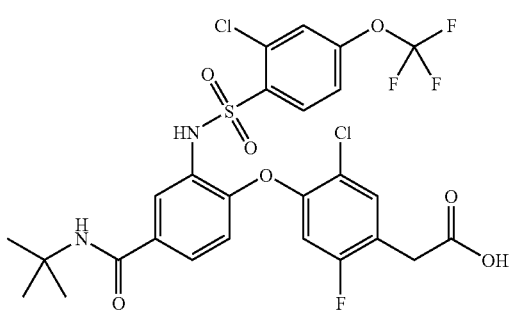 | 9.3 | 19.4 | 2.0 | 14.5 | 37.8 | 17.3 |
| 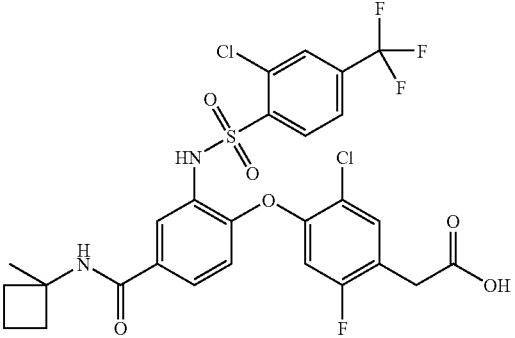 | 8.1 | 18.4 | ND | 15.1 | 41.9 | ND |

TABLE 1-continued

| Example Compound | CRTH2 IC$_{50}$ (nM) | | | DP IC$_{50}$ (nM) | | |
|---|---|---|---|---|---|---|
| | Buffer | Plasma | whole blood | Buffer | Plasma | whole blood |
| (structure) | 3 | 10 | ND | 5 | 39 | ND |
| (structure) | 3 | 8 | 0.2 | 3 | 26 | 1 |
| (structure) | 6.2 | 15.7 | ND | 10.7 | 31.9 | ND |
| (structure) | 3.2 | 12.1 | ND | 2.8 | 25.6 | ND |

TABLE 1-continued

| Example Compound | CRTH2 IC$_{50}$ (nM) | | | DP IC$_{50}$ (nM) | | |
|---|---|---|---|---|---|---|
| | Buffer | Plasma | whole blood | Buffer | Plasma | whole blood |
| (structure) | 10 | 35.8 | ND | 15.6 | 51.6 | ND |
| (structure) | 4.9 | 10.9 | ND | 3.9 | 21.8 | 18.3 |
| (structure) | 1.3 | 7.0 | ND | 2.2 | 22.9 | ND |
| (structure) | 5 | 13 | ND | 18 | 79 | ND |

REFERENCE TABLE 2
| Reference Compound | CRTH2 IC$_{50}$ (nM) | | | DP IC$_{50}$ (nM) | | |
|---|---|---|---|---|---|---|
| | Buffer | Plasma | whole blood | Buffer | Plasma | whole blood |
| 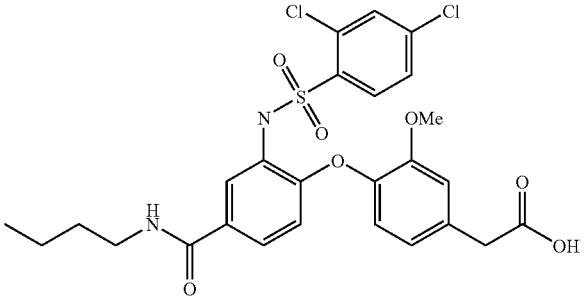 AMG 009 | 3 | 26 | 1 | 13 | 347 | 148 |
| 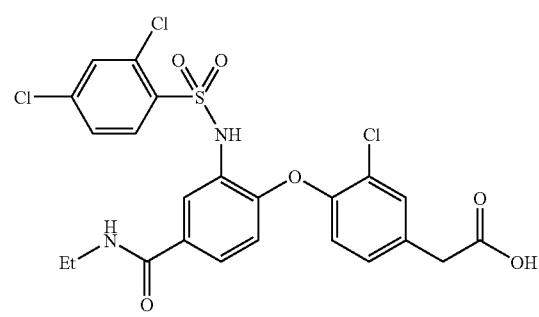 | 2.2 | 71 | ND | 12 | ND | ND |
| 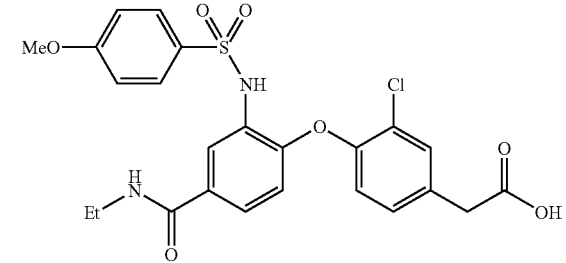 | 2.7 | 16.7 | ND | ND | ND | ND |
| 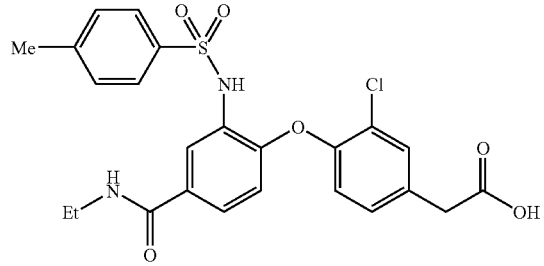 | 2.3 | 26 | ND | ND | ND | ND |

REFERENCE TABLE 2-continued

| Reference Compound | CRTH2 IC$_{50}$ (nM) | | | DP IC$_{50}$ (nM) | | |
|---|---|---|---|---|---|---|
| | Buffer | Plasma | whole blood | Buffer | Plasma | whole blood |
| (structure: 2,4-dichlorophenylsulfonamide-linked diaryl ether with ethylamide and acetic acid) | 4 | 92 | ND | 120 | 8,418 | ND |
| (structure: 2,4-dichlorophenylsulfonamide-linked diaryl ether with OMe, nBu-amide and acetic acid) | 3.7 | 21 | ND | 13 | 283 | ND |
| (structure: 4-chlorophenylsulfonamide-linked diaryl ether with Cl, nBu-amide and acetic acid) | 2.4 | 43 | ND | 9.1 | 100 | ND |
| (structure: 2,4-difluorophenylsulfonamide-linked diaryl ether with OMe, Br, ethylamide and acetic acid) | 1.6 | 25.7 | ND | >10$^6$ | ND | ND |

All publications and patent applications cited in this specification are herein incorporated by reference as if each individual publication or patent application were specifically and individually indicated to be incorporated by reference. Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

We claim:
1. A compound of the following Formula I

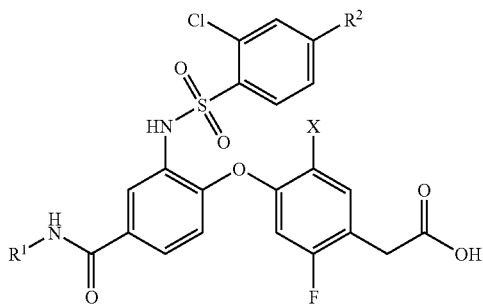

or a pharmaceutically acceptable salt thereof
wherein
R¹ is t-butyl;
R² is halo, alkyl, haloalkyl, alkoxy, haloalkoxy or cycloalkyl; and
X is chloro or fluoro.
2. The compound of claim 1 or the salt thereof, wherein X is chloro.
3. The compound of claim 1 or the salt thereof, wherein R² is cycloalkyl.
4. The compound of claim 3 or the salt thereof, wherein R² is cyclopropyl.
5. A compound having the formula

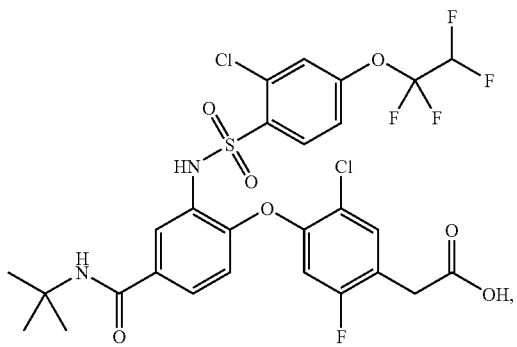

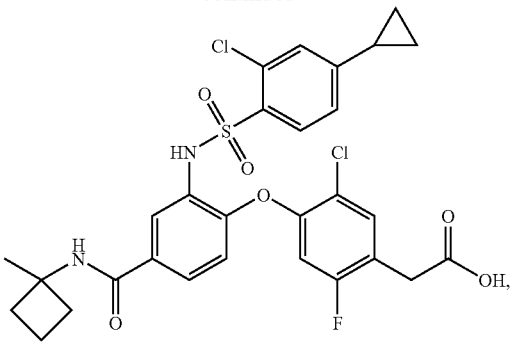

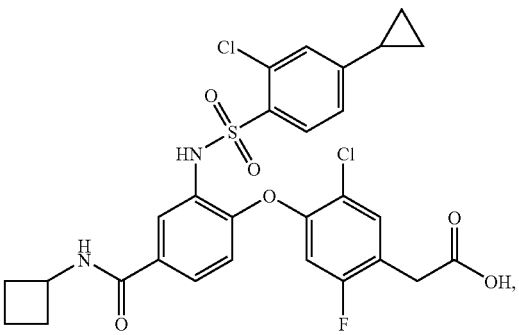

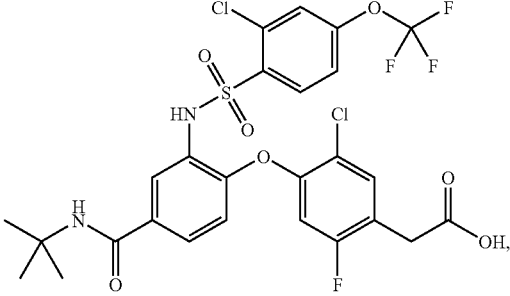

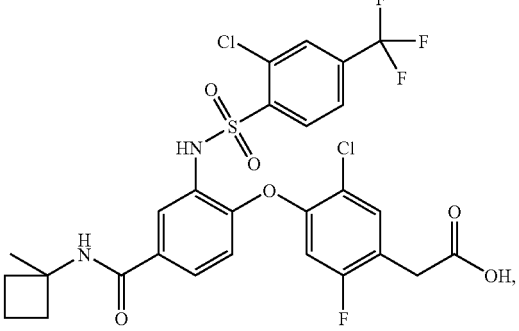

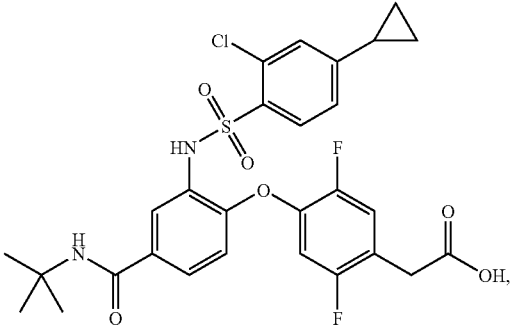

-continued

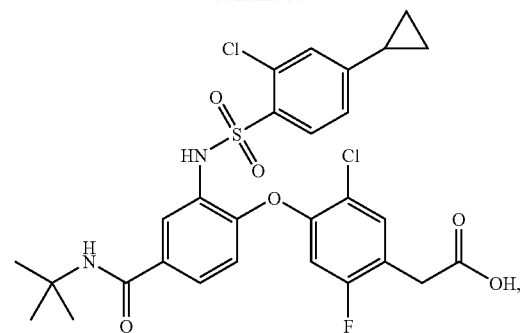

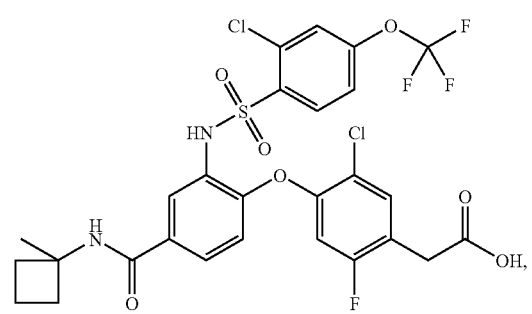

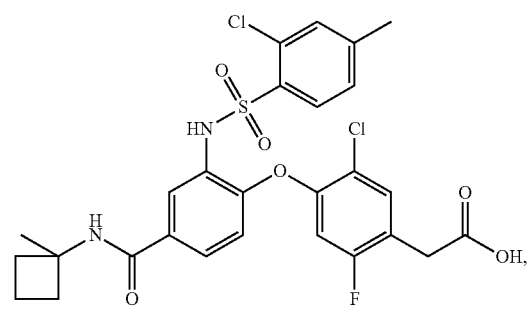

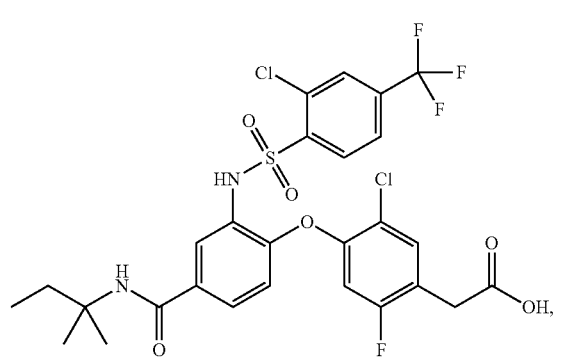

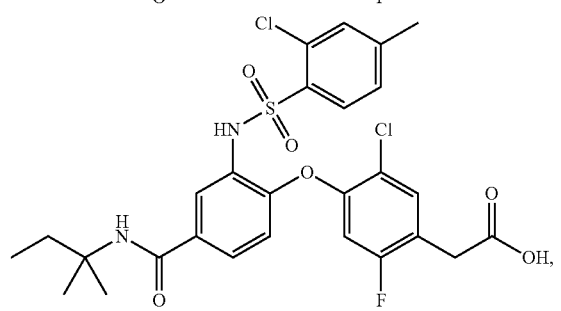

-continued

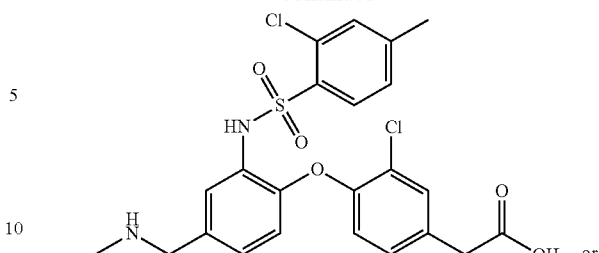

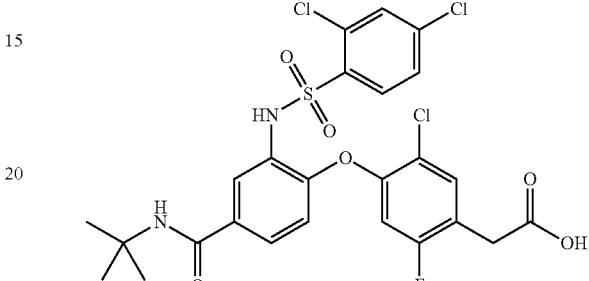

or a pharmaceutically acceptable salt thereof.

6. A compound having the formula

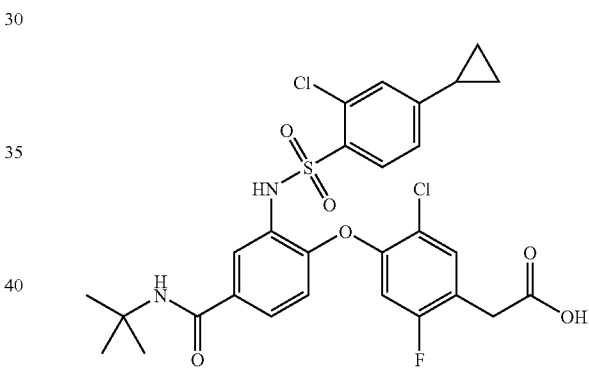

or a pharmaceutically acceptable salt thereof.

7. The compound of claim 6 or the salt thereof, wherein said compound is Form II anhydrous free acid having a single thermal transition when analyzed using DSC, said single thermal transition being an endothermic transition at about 203° C.

8. The compound of claim 7 or the salt thereof, wherein said single thermal transition is an endothermic transition at about 203.22° C.

9. The compound of claim 6 or the salt thereof, wherein said compound is Form II anhydrous free acid having a powder X-Ray diffraction pattern comprising a characteristic peak in terms of 2-theta at about 19.2.

10. The compound of claim 9 or the salt thereof having a powder X-Ray diffraction pattern further comprising a characteristic peak in terms of 2-theta at about 9.5.

11. The compound of claim 10 or the salt thereof having a powder X-Ray diffraction pattern further comprising a characteristic peaks in terms of 2-theta at about 22.0, 20.2, 17.2 and 16.6.

12. A pharmaceutical composition, comprising: the compound of claim 1 or the salt thereof; and a pharmaceutically acceptable carrier, excipient, or diluent.

13. A pharmaceutical composition, comprising: the compound of claim 6 or the salt thereof; and a pharmaceutically acceptable carrier, excipient, or diluent.

14. A compound having the formula

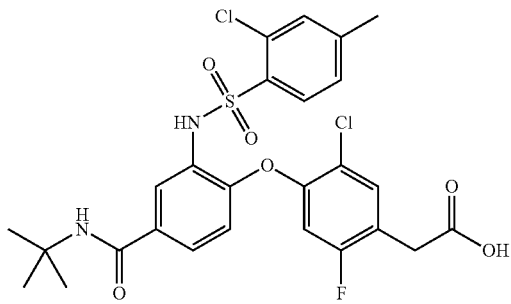

or a pharmaceutically acceptable salt thereof.

15. A pharmaceutical composition, comprising: the compound of claim 14 or the salt thereof; and a pharmaceutically acceptable carrier, excipient, or diluent.

16. A compound of the following Formula I

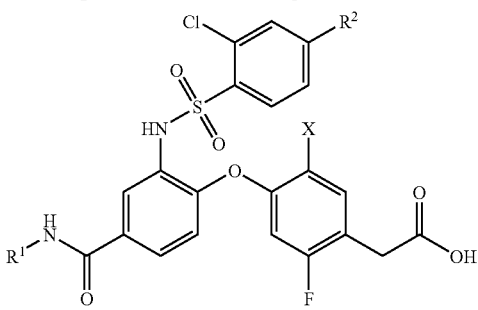

or a pharmaceutically acceptable salt thereof
wherein
$R^1$ is alkyl or cycloalkyl;
$R^2$ is cycloalkyl; and
X is chloro or fluoro.

17. The compound of claim 16 or the salt thereof, wherein X is chloro.

18. The compound of claim 16 or the salt thereof, wherein $R^1$ is alkyl.

19. The compound of claim 16 or the salt thereof, wherein $R^2$ is cyclopropyl.

20. A pharmaceutical composition, comprising: the compound of claim 16 or the salt thereof; and a pharmaceutically acceptable carrier, excipient, or diluent.

\* \* \* \* \*